US008461320B2

(12) United States Patent
De Graaff et al.

(10) Patent No.: US 8,461,320 B2
(45) Date of Patent: *Jun. 11, 2013

(54) METHOD TO ISOLATE MUTANTS AND TO CLONE THE COMPLEMENTING GENE

(75) Inventors: Leendert Hendrik De Graaff, Oosterbeek (NL); Henriëtta Catharina Van Den Broeck, Bennekom (NL); Jacob Visser, Wageningen (NL)

(73) Assignee: DuPont Nutrition Biosciences ApS, Copenhagen K (DK)

( * ) Notice: Subject to any disclaimer, the term of this patent is extended or adjusted under 35 U.S.C. 154(b) by 828 days.

This patent is subject to a terminal disclaimer.

(21) Appl. No.: 10/419,969

(22) Filed: Apr. 22, 2003

(65) Prior Publication Data

US 2003/0175893 A1    Sep. 18, 2003

Related U.S. Application Data

(62) Division of application No. 08/981,729, filed as application No. PCT/NL96/00259 on Jun. 24, 1996, now Pat. No. 6,177,261.

(30) Foreign Application Priority Data

Jun. 23, 1995 (EP) .................................... 95201707
Aug. 30, 1995 (EP) .................................... 95202346

(51) Int. Cl.
   C12N 1/15      (2006.01)
   C12N 15/11     (2006.01)
   C12N 15/80     (2006.01)
   C12P 21/06     (2006.01)

(52) U.S. Cl.
   USPC ..... 536/23.5; 536/23.74; 536/24.1; 536/24.3; 435/69.1; 435/254.11; 435/320.1

(58) Field of Classification Search
   None
   See application file for complete search history.

(56) References Cited

U.S. PATENT DOCUMENTS

| | | | |
|---|---|---|---|
| 5,028,530 | A | 7/1991 | Lai et al. |
| 5,036,002 | A | 7/1991 | Hastrup |
| 5,264,350 | A | 11/1993 | Amory et al. |
| 5,464,758 | A | 11/1995 | Gossen et al. |
| 6,177,261 | B1 | 1/2001 | De Graaff et al. |
| 6,599,745 | B1 | 7/2003 | De Graaff et al. |
| 2003/0175893 | A1 | 9/2003 | De Graaff et al. |

FOREIGN PATENT DOCUMENTS

| | | |
|---|---|---|
| EP | 06-35574 | 1/1995 |
| WO | WO 89/09823 | 10/1989 |
| WO | WO 94/29442 | 12/1994 |
| WO | WO97/00962 | 1/1997 |

OTHER PUBLICATIONS van Peij et al, Isolation and analysis of xlnR, encoding a transcriptional activator co-ordinating xylanolytic expression in *Aspergillus niger*, Molecular Microbiology 27(1): 131-142, 1998.* de Lorenzo et al, Engineering of alkyl- and haloaromatic-responsive gene expression with mini-transposons containing regulated promoters of biodegregadative pathways of *Pseudomonas*, Gene 130:41-46, 1994.*

Scorpione et al., "A New Promoter-Probe Vector for *Saccharomyces cerevisiae* using Fungal Glucoamylase cDNA as the Reporter Gene," *Yeast*, vol. 9, p. 599-605 (1993).

Inouye et al., "Nucleotide Sequence of the Regulatory Gene *xylR* of the TOL plasmid from *Pseudomonas putida*," *Gene*, vol. 66, No. 2, p. 301-306 (1988).

Kreuzer et al., "Identification and Sequence Analysis of the *Bacillus subtilis* W23 *xylR* Gene and *xyl* Operator," *Journal of Bacteriology*, vol. 171, No. 7, p. 3840-3845 (1989).

Rosenfeld et al., "Cloning and Characterization of the *xyl* genes from *Escherichia coli*," *Molecular and General Genetics*, vol. 194, p. 410-415 (1984).

Sizemore et al., "Organization, promoter analysis and transcription regulation of the *Staphylococcus xylosus* xylose utilization operon," *Molecular and General Genetics*, vol. 227, p. 377-384 (1991).

Lokman et al., "Organization and characterization of three genes involved in D-xylose catabolism in *Lactobacillus pentosus*," *Molecular and General Genetics*, vol. 230, p. 161-169 (1991).

Sambrook & Russe 11, Molecular Cloning, A Laboratory Manual, $3^{rd}$ edition, vol. 2, p. 10.47, formula (3) (2001).

Bos et al., "Adenine and pyrimidine genes of *Aspergillus niger* and evidence for a seventh linkage group," *Curr Genet.*, vol. 16, pp. 307-310 (1989).

Van Peij et al., "The Transcriptional activator XlnR regulates both xylanolytic and endoglucanase gene expression in *Aspergillus niger*," *Applied and Environmental Microbiology*, pp. 3615-3619 (Oct. 1998).

Kraulis et al., "Structure of the DNA-binding domain of zinc GAL4." *Nature*, vol. 356, No. 6368, pp. 448-450 (Apr. 1992).

Katz et al, *Mol. Cell. Biol.*, 9(12):5696-5701 (1989).
Fowler et al, *Current Genetics*, 18:537-545 (1990).
De Graaff et al, *Mol. Microbiol.*, 12(3):479-490 (1994).
Buxton et al, *Gene*, 84(2):329-334 (1989).
Wittington et al, *Current Genetics*, 18(6):531-536 (1990).
Flipphi et al, *Microbiology*, 140(10):2673-2682 (1994).
Hata et al, *Current Genetics*, 22:85-91 (1992).
Dowzer et al, *Mol. Cell. Biol.*, 11(11):5701-5709 (1991).
Felenbok et al, *Gene*, 73(2):385-396 (1988).
de Lorenzo et al, *Gene*, 130:41-46 (1993).

(Continued)

*Primary Examiner* — Nancy T Vogel
*Assistant Examiner* — Catherine Hibbert
(74) *Attorney, Agent, or Firm* — Steptoe & Johnson LLP

(57) ABSTRACT

The subject invention lies in the field of microorganism mutation and selection of the mutants. In particular, the invention is directed at obtaining metabolic mutants in a simple, direct and specific manner. In a preferred embodiment it is also possible to obtain desired mutants not comprising recombinant DNA, thereby facilitating incorporation thereof in products for human consumption or application, due to shorter legislative procedures. The method according to the invention involves random mutation and specific selection of the desired metabolic mutant. Knockout, mutants wherein a gene associated with metabolism is absent or inactivated and mutants with increased or decreased DNA binding capacity are also claimed.

11 Claims, 3 Drawing Sheets

OTHER PUBLICATIONS de Graaff et al, *Molecular Microbiology*. 12:479-490 (1994).
Fowler et al, *Curr. Genet.*, 18:537-545 (1990).
Senear et al., *Journal of Biological Chemistry*, vol. 266, No. 21, p. 13661-13671 (1991).
Garner et al., *Nucleic Acids Research*, vol. 9, No. 13, p. 3047-3060 (1981).
Kerr, *Methods of Enzymology*, vol. 254, p. 619-632 (1995).
Hendrickson et al., *Journal of Molecular Biology*, vol. 174, p. 611-628 (1984).
Fried, *Electrophoresis*, vol. 10, p. 366-376 (1989).
Revzin, *BioTechniques*, vol. 7, No. 4, p. 346-355 (1989).
Celgarek et al., *Electrophoresis*, vol. 10, p. 360-365 (1989).
Oxford Dictionary of Biology and Biochemistry 2000, *Oxford University Press* ISBN 0 19 850673 2 p. 360.
Oxford Dictionary of Biology and Biochemistry 2000, *Oxford University Press* ISBN 0 19 850673 2 pp. 259, 559, 695.
A Dictionary of Genetics 4th Edition eds King and Stansfield. *Oxford University Press* 1990.pp. 128, 269, 340.
Molecular Cloning A Laboratory Manual second edition. Sambrook and Maniatis 1989 *Cold Spring Harbour Laboratory Press*. ISBN 0-87969-309-6 pp. 9.47-9.58.
Parthun M. R. and Jaehning J. A., "Purification and Characterization of the Yeast Transcriptional Activator GAL4*", *Journal of Biological Chemistry*, 1990, vol. 265, No. 1, p. 209-213.
Thukral S. K. et al., "Two Monomers of Yeast Transcription Factor ADR1 Bind a Palindromic Sequence Symmetrically to Activate ADH2 Expression", *Molecular and Cellular Biology*, 1991, vol. 11, No. 3, p. 1566-1577.
Amory et al., Characterization of the sacQ Genes from *Bacillus licheniformis* and *Bacillus subtilis, Journal of Bacteriology*, 1987, vol. 169, No. 1, p. 324-333.
Stricker et al., "Xyr1 (Xylanase regulator 1) Regulates both the Hydrolytic Enzyme System and D-Xylose Metabolism in *Hypocrea jecorina*", *Eurkaryotic Cell*, 2006, vol. 5, No. 12, p. 2128-2137.
Benson et al., Nucleic Acids Research, 1994, vol. 22, No. 17, p. 3441-3444.
Benton, Nucleic Acids Research, 1990, vol. 18, No. 6, p. 1517-1520.
Brown, T A, Gene Cloning an introduction, 3rd edition, Chapman Hall, London,1995, p. 216-219.
Crea and Horn, Nucleic Acids Research, 1980, vol. 8, No. 10, p. 2331-2348.
Horn et al., Nucleic Acids Research, Symposium Series, 1980, vol. 7, p. 225-232.
Klug and Cummings, Concepts of Genetics, Macmillan Publishing Company, 3rd edition, 1991, p. 303-304, A7-A8.
Lewin, B, Genes V, Oxford University Press,1994 pp. 112-113, 643-645.
Matthes, et al., The EMBO Journal, 1984, vol. 3, No. 4, p. 801-805.

\* cited by examiner

METHOD TO ISOLATE MUTANTS AND TO CLONE THE COMPLEMENTING GENE

CROSS-REFERENCE TO RELATED APPLICATIONS

This application is a Divisional of U.S. application Ser. No. 08/981,729, filed Dec. 23, 1997 (now issued as U.S. Pat. No. 6,177,261), which is a 371 of PCT/NL96/00259, filed Jun. 24, 1996. The disclosures of both application are incorporated herein by reference.

BACKGROUND OF THE INVENTION

The subject invention lies in the field of microorganism mutation and selection of the mutants. In particular the invention is directed at obtaining metabolic mutants in a simple, direct and specific manner. In a preferred embodiment it is also possible to obtain desired mutants not comprising recombinant DNA, thereby facilitating incorporation thereof in products for human consumption or application, due to shorter legislative procedures. The method according to the invention involves random mutation and specific selection of the desired metabolic mutant. The method can suitably be carried out automatically. Such a mutant can exhibit either increased or decreased metabolic activity. The specificity of the method lies in the selection conditions applied. The mutants obtained are mutated in their regulatory function with regard to a predetermined part of metabolism. Dependent on the selection conditions derepressed mutants can be isolated that will thus exhibit overexpression or mutants can be found in which particular metabolic enzymic activity is eliminated. It thus becomes possible to eliminate undesirable metabolic enzymic activity or to increase desirable metabolic activity.

The methods according to the invention can suitably be carried out on well characterised sources that are already widely used in industry. The overexpressing mutants can for example be used as major sources of enzymes producing huge amounts at low cost. The initial strain to be mutated will depend on several factors known to a person skilled in the art such as: efficient secretion of proteins, the availability of large scale production processes, experience with downstream processing of fermentation broth, extensive genetic knowledge and the assurance of using safe organisms.

In another aspect of the invention it has now also become possible to ascertain and identify specific metabolic gene regulating functions.

To date a method for preparing mutants that was industrially applicable and could be automated was a method of mutating without selection and subsequent analysis of the mutants for the aspect which was to be amended. An alternative method with selection always required an enrichment step, followed by selection on the basis of growth or non growth. This meant a large number of undesired mutants had first to be weeded out. Also the existing method resulted in a high number of mutants with an incorrect phenotype and thus exhibits low selectivity.

Some years ago Gist-Brocades developed and introduced the pluGBug marker gene free technology for *Aspergillus niger*. In the GIST 94/60 p 5-7 by G. Selten a description is given of a vector for *Aspergillus niger* comprising glucoamylase regulatory regions to achieve high expression levels of the gene it regulates. This was selected as regulatory region on the basis of the naturally high expression of glucoamylase by native *Aspergillus niger*. Using recombinant DNA techniques the regulatory region was fused appropriately to the gene of interest as was the selection marker *Aspergillus* amdS, allowing selection of the desired transformants after transferring the expression cassette to the *A. niger* host. Multiple copies of the expression cassette then become randomly integrated into the *A. niger* genome. The enzyme produced as described in the article was phytase. Subsequently the generation of marker free transformants can be achieved. In the known system the generation of marker free recombinant strains is actually a two step process since the amdS gene can be used bidirectionally. First in a transformation round to select initial transformants possessing the offered expression cassette and subsequently in a second round by counterselecting for the final recombinant strain which has lost the amdS gene again. The amdS gene encodes an enzyme which is able to convert acetamide into ammonium and acetate. Acetamide is used as sole N-source in the transformation round. In the recombination round fluoro acetamide is used as selective N-source, with a second appropriate N source such as e.g. urea. As the product fluoroacetate is toxic for other cells the propagation will be limited to those cells which have lost the amdS gene by an internal recombination event over the DNA repeats within the expression cassette. The largest problem with the known method is the fact that the resulting strain is a recombinant strain. The desired characteristic has to be introduced by incorporation of "foreign" nucleic acid, which can lengthen the time required for and sometimes even prevent legislative approval. In addition the method is not suited for developing strains with amended metabolism. Due to the presence of enzyme cascades and multiple feedback loops the mere incorporation of a particular gene cannot always lead to the desired result. Overproduction of a particular product as encoded can be compensated for by concomitant overexpression of another product or down regulated thus annulling the effect of the incorporated gene. The incorporation of DNA will therefore often be a case of trial and error with the incorporation of the desired nucleic acid being selectable but the desired phenotype not necessarily concomitantly being achieved. Furthermore the loss of the marker gene is a spontaneous process which takes time and cannot be guaranteed to occur for all transformants comprising the nucleic acid cassette.

It is known that strain improvement in microorganisms can be achieved by modification of the organism at different levels. Improvement of gene expression at the level of transcription is mostly achieved by the use of a strong promoter, giving rise to a high level of mRNA encoding the product of interest, in combination with an increase of gene dosage of the expression cassette. Although this can lead to an increase of the product formed, this strategy can have a disadvantage in principle. Due to the presence of multiple copies of the promoter the amount of transcriptional regulator driving transcription can become limited, resulting in a reduced expression of the target gene or genes of the regulator. This has been observed in the case of *Aspergillus nidulans* strains carrying a large number of copies of the amdS gene (Kelly and Hynes, 1987; Andrianopoulos and Hynes. 1988) and in the case of *A. nidulans* strains carrying multiple copies of a heterologous gene under the atcA promoter (Gwynne et al. 1987). In the latter case an increase of the atcR gene, encoding the transcriptional regulator of the atcA-gene, resulted in the increase of expression of the expression cassette (Gwynne et al., 1987; Davies. 1991). In analogy to the effects found in *Aspergillus nidulans*, in *Aspergillus niger* similar limitations were observed in using the glucoamylase (glaa) promoter, due to limitation of the transcriptional regulator driving transcription (Verdoes et al. 1993; Verdoes et al 1995; Verdoes, 1994). Cloning of the glaA regulatory gene has thus far been hampered by lack of selection strategy.

In the case of the arabinase gene expression a clear competition for transcriptional regulator was found upon the increase of arabinase gene dosage (Flipphi et al. 1994), reflecting a limitation of a transcriptional regulator common to all three genes studied.

In addition to the abovementioned drawbacks of the state of the art isolation and determination of regulator genes has until now been extremely difficult due to the fact that most of the regulatory proteins exist in very low concentrations in the cell making it difficult to determine which substance is responsible for regulation. In addition generally the regulatory product is not an enzyme and can only be screened for by a DNA binding assay which makes it difficult to determine and isolate and is very time consuming. Thus far the strategies used to clone regulatory genes are e.g.:

- by complementation, which however requires a mutant to be available,
- by purification of the regulatory protein, which is extremely laborious, since the protein can only be characterised by, its DNA binding properties. Some of these purifications include affinity chromatography using a bound DNA fragment as a matrix. One of the drawbacks in this type of purification is that often more, than one protein binds both specifically as well as non-specifically to the fragment,
- based on gene clustering wherein the regulatory gene is genomically clustered with the structural genes which are regulated by its gene product, e.g. the prn cluster, the alc cluster.

DETAILED DESCRIPTION OF THE INVENTION

Figure 1:
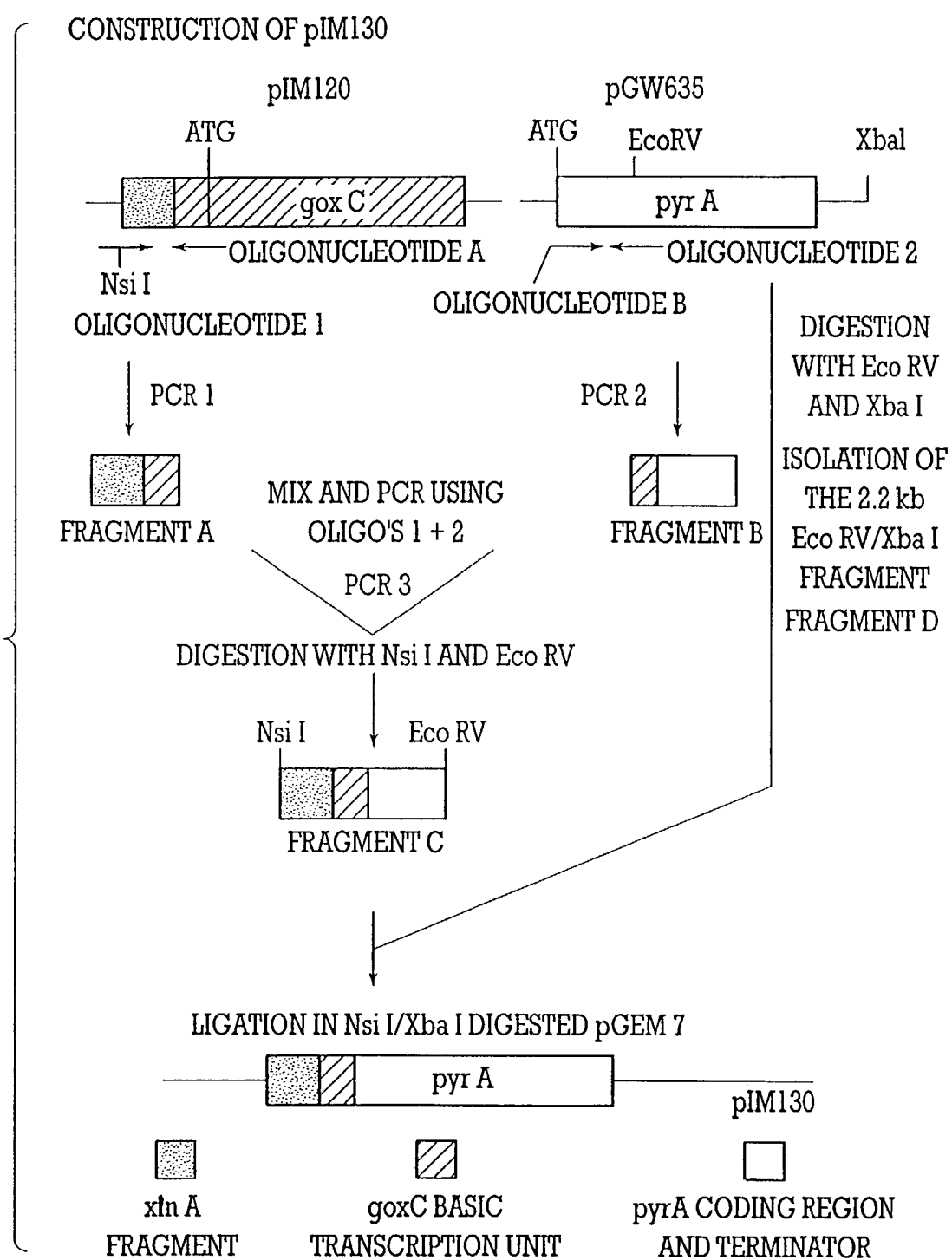
FIG. 1 depicts the construction of the selection plasmid pIM130.

We have now achieved a system that can be used for shortening the length of time required for registration of mutant microorganisms capable of overproduction of particular desirable enzymes. The system overcomes the problem of multiple random inserts of "foreign" nucleic acid and in particular of the selection marker gene. It does not even require foreign nucleic acid to achieve the desired characteristic. The resulting mutant strain will not comprise heterologous nucleic acid. In addition the system according to the invention enables specific mutation of metabolism and prevents a large deal of experimentation leading to undesired phenotypes.

The subject invention is directed at a nucleic acid cassette comprising a nucleic acid sequence encoding a bidirectional marker, said nucleic acid cassette further comprising a basic transcriptional unit operatively linked to the nucleic acid sequence encoding the bidirectional marker and said nucleic acid cassette further comprising an inducible enhancer or activator sequence linked to the basic transcription unit in such a manner that upon induction of the enhancer or activator sequence the bidirectional marker encoding nucleic acid sequence is expressed, said inducible enhancer or activator sequence being derived from a gene associated with activity of part of the metabolism, said inducible enhancer or activator sequence being derived from a gene associated with metabolism.

A basic transcription unit comprises any elements required for transcription of the gene to which the transcription is linked. It can comprise the promoter with or without enhancer sequences. The basic transcription unit must be operative in the host organism. The basic transcription unit must be located such that it is operatively linked, to the bidirectional marker gene for transcription thereof to be possible. Suitable examples are well known for a number of host cells such as e.g. *Aspergillus, Trichoderma, Penicillium, Fusarium, Saccharomyces, Kluyvromyce* and *Lactobacillus*. In the Examples the basic transcription unit tGOX derived from the *Aspergillus niger* goxC transcription unit (Whittington et al. 1990) is illustrated in an operable embodiment of the invention.

The inducible enhancer or activator sequence is preferably normally involved in regulation of an enzyme cascade or involved in a part of metabolism involved with one or more feed back loops. In a further embodiment a nucleic acid cassette according to the invention comprises an inducible enhancer or activator sequence that is normally involved in carbon metabolism. Suitable examples of inducible enhancer or activator sequence to be used in a nucleic acid cassette according to the invention are the Upstream Activating Sequence (UAS) as comprised on any of the following fragments of nucleic acid:

- a fragment originating from the promoters of the abfA, abfB and abna genes encoding respectively arabinofuranosidase A, arabinofuranosidase B and endoarabinase,
- a fragment originating from the glaa gene encoding glucoamylase.
- a fragment containing the atcR binding site such as on the alcR and alcA promoter.
- a fragment originating from the CUP1 gene.
- a fragment originating from the PH05 gene
- a fragment originating from the GAL1, GAL7 or GAL10 genes.
- a fragment originating from the xlnA gene
- a fragment originating from the pgaII gene.

By way of example these fragments can be derived from the following organisms as is described in the literature:

- a fragment originating from the promoters of the abfA, abfb and abn genes encoding respectively arabinofuranosidase A, arabinofuranosidase B and endoarabinase of *Aspergillus niger* (Flipphi M. J. A. et al. 1994)
- a fragment originating from the glaA gene encoding glucoamylese of *Aspergillus niger*, (Fowler T. et al 1990)
- a fragment containing the alcR binding site such as on the atcR promoter of *Aspergillus nidulans* (Felenbok B. et al. 1994),
- a fragment originating from the CUP1 gene of *Saccharomyces cerevisiae* (Hinnen A. et al. 1995)
- a fragment originating from the YHO5 gene of *Saccharomyces cerevisiae* (Hinnen A. et al. 1995)
- a fragment originating from the GAL1, GAL7 or GAL10 genes of *Saccharomyces cerevisiae* (Hinnen A. et al. 1995).
- a fragment originating from the xlnA, xlnB, xlnC or xlnD genes of *Aspergillus nidulans*, a fragment originating from the xlnB, xlnC or xlnD genes of *Aspergillus niger* (see elsewhere in this description),
a fragment originating from the xlnA or xlnD genes of *Aspergillus tubigensis* (de Graaff et al. 1994).
a fragment originating from the pgaII gene of *Aspergillus niger* (see elsewhere in this document).

In the Examples UAS of xlnA is illustrated in an operable embodiment of the invention.

A bidirectional marker is an art recognised term. It comprises a selection marker that can be used to indicate presence or absence of expression on the basis of the selection conditions used. A preferred bidirectional marker will confer selectability on the basis of lethality or extreme reduction of growth. Alternatively different colouring of colonies upon expression or lack of expression of the bidirectional marker gene is also a feasible embodiment. Suitable examples of known bidirectional markers are to be found in the group consisting of the facB, the NiaD, the AmdS, the Can1, the Ura3, the Vra4 and the PyrA genes. We hereby point out that PyrA homologues are also referred to in the literature as PyrG, Vra3, Vra4, Pyr4 and Pyr1. These genes can be found in i.a. the following organisms the facb gene in *Aspergillus nidulans*, the NiaD gene in *Aspergillus niger*, the NiaD gene in *Aspergillus oryzae*, the AmdS gene in *Aspergillus nidulans*, the Can1 gene in *Schizosaccharomyces pombe*, the Ura3 gene in *Saccharomyces cerevisiee*, the Ura4 gene in *Saccharomyces pombe* and the PyrA genes in *Aspergillus, Trichoderms, Penicillium, Fusarium, Saccharomyces* and *Kluyveromyces*.

Selection of facB mutants i.e. with a negative phenotype can occur on the basis of fluoro-acetate resistance. Selection for FAC B* i.e. a positive phenotype can occur on acetate as a carbon source (Katz, M. E. and Hynes M. J. 1989). Selection of niaD mutants i.e. with a negative phenotype can occur on the basis of chlorate resistance. Selection for NIA D* i.e. a positive phenotype can occur on nitrate as a nitrogen source (Unkles S. E. et al. 1989a and 1989b). Selection of amdS mutants i.e. with a negative phenotype can occur on the basis of fluor acetamide resistance. Selection for AMD S* i.e. a positive phenotype can occur on acetamide as a nitrogen source. As most fungi do not have a gene encoding an acetamidase function AMD S is a dominant marker for such fungi. It has been used as such in *Aspergillus niger, Aspergillus niger* var; *tubigensis, Aspergillus niger* var. *awamori, Aspergillus foetidus, Aspergillus oryzae, Aspergillus sydowii, Aspergillus japonicus Aspergillus aculeatus, Penicillium* species. *Trichoderma* species among others (Kelly and Hynes 1985 and Bailey et al. 1991). Selection of can1 mutants i.e. with a negative phenotype can occur on the basis of canavanine resistance, wherein canavanine is an arginine analogue. Selection for CAN 1* i.e. a positive phenotype can occur on arginine (Ekwall K. 1991). The gene encoding orothidine 5'-β-decarboxylase is known as pyrA, pyrG or ura3. It has been found for various organisms e.g. *Aspergillus, Trichoderma, Penicillium, Fusarium, Saccharomyces* and *Kluyveromyces*. Selection of pyrA mutants i.e. with a negative phenotype, also described as pyrG or ura3 can occur on the basis of fluoro orotic acid resistance. Selection for PYR A$^+$ and homologues thereof i.e. a positive phenotype can be done on the basis of uridine or uracil prototrophy. In the Examples pyrA from *Aspergillus niger* (Wilson et al. 1988) is illustrated in an operable embodiment of the invention. Other examples are known to a person skilled in the art and can be readily found in the literature. The selection marker to be used will depend on the host organism to be mutated and other secondary considerations such as ease of selectability, reliability and cost of substrates to be used amongst others.

The nucleic acid cassette incorporated in a transformation or (expression vector is also included in the scope of the invention. Also included is the application of such nucleic acid cassette or vector in transformation and selection methods. In particular in methods for producing mutants exhibiting overexpression of an enzyme involved in a predetermined part of metabolism, methods for producing mutants exhibiting reduced or inhibited expression of an enzyme involved in a predetermined part of metabolism and methods for determining and isolating regulatory genes involved in predetermined parts of metabolism.

Thus a method for preparing and selecting a mutant strain of microorganism, said mutation enhancing a predetermined part of metabolism in comparison to the non mutated strain, said method comprising introducing into a host a nucleic acid cassette according to any of the preceding claims.

said host not exhibiting the phenotype associated with expression of the bidirectional marker prior to introduction of the nucleic acid cassette, culturing a resulting microorganism under conditions wherein the enhancer or activator sequence comprised on the nucleic acid cassette is normally active and under conditions wherein the bidirectional marker is expressed and wherein preferably expression of said bidirectional marker will lead to growth and non expression to non growth.

selecting a transformant that exhibits the phenotype corresponding to the expression of the bidirectional marker gene under the aforementioned culturing conditions, subjecting the selected transformant to mutagenesis in a manner known per se, culturing the resulting strain under conditions acceptable for a strain with a phenotype corresponding to the expression of the bidirectional marker and under conditions that in the non mutated parent comprising the nucleic acid cassette result in non-expression of the bidirectional marker and in the presence of a metabolisable substrate for the predetermined part of metabolism, selecting a strain resulting from the cultivation step following mutagenesis that exhibits a phenotype corresponding to the expression of the bidirectional marker gene under selection conditions that for the non mutated parent comprising the nucleic acid cassette result in non-expression of the bidirectional marker falls within the scope of the invention.

In a suitable embodiment of this method the inducible enhancer or activator sequence is the Upstream Activating Sequence (UAS) derived from the gene xlnA, the predetermined part of the metabolism is the xylanolytic part of carbon metabolism, the culturing step wherein the resulting microorganisms are cultivated under conditions wherein the enhancer or activator sequence is normally active and wherein the bidirectional marker is expressed comprises cultivation in the presence of inducer of UAS and absence of repressor of UAS and a metabolisable source of carbon.

the selecting of a transformant that exhibits the phenotype corresponding to the expression of the bidirectional marker gene occurs under the aforementioned culturing conditions, the culturing step after mutagenesis of the selected transformant occurs under conditions acceptable for a strain with a phenotype corresponding to the expression of the bidirectional marker and under conditions that in the non mutated parent comprising the nucleic acid cassette result in non-expression of the bidirectional marker i.e. in the presence of repressor of UAS and in the presence of a metabolisable source of carbon and optionally also in the presence of inducer of UAS, the selection of a strain resulting from the cultivation step following mutagenesis of a strain that exhibits a phenotype corresponding to the expression of the bidirectional marker gene occurs under selection conditions that for the non mutated parent comprising the nucleic acid cassette result in non-expression of the bidirectional marker.

In a further embodiment of this method the nucleic acid cassette comprises a nucleic acid sequence encoding the bidirectional marker pyrA.

the host does not exhibit the pyrA+ phenotype associated with expression of the bidirectional marker prior to introduction of the nucleic acid cassette, the culturing step wherein the resulting microorganisms are cultivated under conditions wherein the enhancer or activator sequence is normally active and wherein the bidirectional marker is expressed comprises cultivation under conditions wherein the enhancer or activator is normally active i.e. in the presence of inducer of the enhancer or activator and in the absence of repressor of the enhancer or activator and under conditions wherein the bidirectional marker is expressed.

the selecting of a transformant that exhibits the phenotype corresponding to the expression of the bidirectional marker gene occurs under the aforementioned culturing conditions, the culturing step after mutagenesis of the selected transformant occurs under conditions acceptable for a strain with a phenotype corresponding to the expression of the bidirectional marker and under conditions that in the non mutated parent comprising the nucleic acid cassette result in non-expression of the bidirectional marker i.e. in the absence of inducer of the enhancer or activator or in the presence of repressor of the enhancer or activator and in the presence of a metabolisable substrate for the predetermined part of metabolism.

the selection of a strain resulting from the cultivation step following mutagenesis of a strain that exhibits a phenotype corresponding to the expression of the bidirectional marker gene occurs under selection conditions that for the non mutated parent comprising the nucleic acid cassette result in non-expression of the bidirectional marker i.e. in the absence of inducer of the enhancer or activator or the presence of repressor of the enhancer or activator.

Suitably the embodiments just mentioned can further be characterised by the nucleic acid cassette comprising a nucleic acid sequence encoding the bidirectional marker pyrA.

the host not exhibiting the pyrA+ phenotype associated with expression of the bidirectional marker prior to introduction of the nucleic acid cassette, the inducible enhancer or activator sequence being the UAS derived from the gene xlnA, the culturing step wherein the resulting microorganisms are cultivated under conditions wherein the enhancer or activator sequence is normally active and wherein the bidirectional marker is expressed comprises cultivation under conditions wherein UAS is normally active i.e. in the presence of inducer of UAS such as xylose or xylan and in the absence of repressor of UAS i.e. absence of glucose and under conditions wherein the bidirectional marker is expressed, the selecting of a transformant that exhibits the phenotype corresponding to the expression of the bidirectional marker gene occurs under the aforementioned culturing conditions, the culturing step after mutagenesis of the selected transformant occurring under conditions acceptable for a strain with a phenotype corresponding to the expression of the bidirectional marker and under conditions that in the non mutated parent comprising the nucleic acid cassette result in non-expression of the bidirectional marker i.e. in the absence of inducer of UAS such as xylose or xylan or in the presence of repressor of UAS i.e. in the presence of glucose and in the presence of a metabolisable source of carbon.

the selection of a strain resulting from the cultivation step following mutagenesis of a strain that exhibits a phenotype corresponding to the expression of the bidirectional marker gene occurring under selection conditions that for the non mutated parent comprising the nucleic acid cassette result in non-expression of the bidirectional marker i.e. in the absence of inducer of UAS such as, xylose or xylan or the presence of repressor of UAS i.e. in the presence of glucose.

In addition a method for preparing and selecting a non recombinant mutant strain of microorganism, said mutation enhancing a predetermined part of metabolism in comparison to the non mutated strain falls within the preferred scope of the invention. This method comprising carrying out the steps of the method according to the invention as described in the preceding paragraphs followed by crossing out in a manner known per se the nucleic acid of the introduced nucleic acid cassette.

As indicated previously a method for preparing and selecting a mutant strain of microorganism, said mutation inhibiting a predetermined part of the carbon metabolism in comparison to the non mutated strain, said method comprising introducing into a host a nucleic acid cassette according to the invention as described above said host not exhibiting the phenotype associated with expression of the bidirectional marker prior to introduction of the nucleic acid cassette and said host exhibiting activity of the type characterising the predetermined part of metabolism to be reduced or inhibited.

culturing a resulting microorganism under conditions wherein the enhancer or activator sequence of the nucleic acid cassette is normally active and wherein non expression of the bidirectional marker of the nucleic acid cassette will result in growth and detection of the resulting microorganism and wherein expression of said bidirectional marker will preferably be lethal or strongly inhibit growth, selecting a transformant that exhibits the phenotype corresponding to the expression of the bidirectional marker gene under the aforementioned culturing conditions subjecting the selected transformant to mutagenesis in a manner known per se, culturing the strain resulting from the mutagenesis under conditions acceptable for growth of a strain with a phenotype corresponding to the non expression of the bidirectional marker and in the presence of a metabolisable substrate and under conditions that illustrate the reduced or inhibited activity of the predetermined part of metabolism in comparison to the non mutated host either with or without the nucleic acid cassette, selecting a strain resulting from the cultivation step following mutagenesis that exhibits a phenotype corresponding to the reduced or inhibited activity of the predetermined part of the metabolism under selection conditions that illustrate the reduced or inhibited activity of the predetermined part of metabolism in comparison to the non mutated host with or without nucleic acid cassette such as a reduced zone of clearing upon growth on a substrate which serves as a substrate for the part of metabolism for which the activity is to be reduced or inhibited.

In a further embodiment of such a method
the inducible enhancer or activator sequence is the Upstream Activating Sequence (UAS) derived from the gene xlnA
the predetermined part of the metabolism is the xylanolytic part of carbon metabolism,
the culturing step wherein the resulting microorganisms are cultivated under conditions wherein the enhancer or activator sequence is normally active and wherein the bidirectional marker is expressed comprises cultivation in the absence of repressor of the UAS of the nucleic acid cassette, in the presence of a metabolisable source of carbon and preferably also in the presence of inducer of the UAS.
the selecting of a transformant that exhibits the phenotype corresponding to the expression of the bidirectional marker gene occurs under the aforementioned culturing conditions.
the culturing step after mutagenesis of the selected transformant occurs under conditions acceptable for growth and detection of a strain with a phenotype corresponding to the non expression of the bidirectional marker, under conditions that are unacceptable for growth and detection of a strain with a phenotype corresponding to the expression of the bidirectional marker i.e. in the presence of uridine and fluoro-orotic acid and under conditions that in the non mutated parent comprising the nucleic acid cassette result in activity of the predetermined part of the carbon metabolism i.e. in the presence of inducer of the UAS and a metabolisaole carbon source and the absence of repressor of the UAS for example the presence of sorbitol or an alternative non repressing source of carbon in combination with an inducer like xylan or D-xylose.
the selection of a strain resulting from the cultivation step following mutagenesis that exhibits a phenotype corresponding to the reduced or inhibited activity of the predetermined part of the carbon metabolism occurs under selection conditions that illustrate the reduced or inhibited activity of the predetermined part of carbon metabolism in comparison to the non mutated host either with or without the nucleic acid casette such as a reduced zone of clearing upon growth on xylan.

An example of the method according to the preceding paragraph is provided, wherein
the nucleic acid cassette comprises a nucleic acid sequence encoding the bidirectional marker pyrA.
the host does not exhibit the PYRA+ phenotype associated with expression of the bidirectional marker prior to introduction of the nucleic acid cassette.
the culturing step wherein the resulting microorganisms are cultivated under conditions wherein the enhancer or activator sequence is normally active and wherein the bidirectional marker pyrA is expressed i.e. comprises cultivation in the presence of inducer of the enhancer or activator and in the absence of repressor of the enhancer or activator and under conditions wherein the bidirectional marker pyrA is expressed,
the selecting of a transformant that exhibits the phenotype corresponding to the expression of the bidirectional marker gene pyrA occurs under the aforementioned culturing conditions,
the culturing step after mutagenesis of the selected transformant occurs under conditions acceptable for growth and detection of a strain with a phenotype corresponding to the non expression of the bidirectional marker i.e. PYRA-phenotype, under conditions that are unacceptable for growth and detection of a strain with a PYRA$^+$ phenotype, such a phenotype corresponding to the expression of the bidirectional marker i.e. such conditions comprising the presence of uridine and fluoro-orotic acid and under conditions that in the non mutated parent comprising the nucleic acid cassette result in activity of the predetermined part of the metabolism i.e. in the presence of inducer of the enhancer or activator and a metabolisoble substrate and the absence of repressor of the activator or enhancer or an alternative non repressing substrate in combination with an inducer.

In a preferred embodiment the method according to the preceding 2 paragraphs is a method, wherein furthermore
the nucleic acid cassette comprises a nucleic acid sequence encoding the bidirectional marker pyrA.
the host does not exhibit the PYRA+ phenotype associated with expression of the bidirectional marker prior to introduction of the nucleic acid cassette,
the inducible enhancer or activator sequence is the UAS derived from the gene xlnA
the culturing step wherein the resulting microorganisms are cultivated under conditions wherein the enhancer or activator sequence is normally active and wherein the bidirectional marker pyrA is expressed comprises cultivation under conditions wherein the UAS is normally active i.e. in the presence of inducer of the UAS such as xylose or xylan and in the absence of repressor of the UAS i.e. absence of glucose and under conditions wherein the bidirectional marker pyrA is expressed.
the selecting of a transformant that exhibits the phenotype corresponding to the expression of the bidirectional marker gene pyrA occurs under the aforementioned culturing conditions.
the culturing step after mutagenesis of the selected transformant occurs under conditions acceptable for growth and detection of a strain with a phenotype corresponding to the non expression of the bidirectional marker i.e. pyrA-phenotype, under conditions that are unacceptable for growth and detection of a strain with a PYRA* phenotype, such a phenotype corresponding to the expression of the bidirectional marker i.e. such conditions comprising the presence of uridine and fluoro-orotic acid and under conditions that in the non mutated parent comprising the nucleic acid cassette result in activity
of the predetermined part of the carbon metabolism i.e. in the presence of inducer of the UAS and a metabolisable carbon source and the absence of repressor of the UAS for example the presence of sorbitol or an alternative non repressing source of carbon in combination with an inducer like xylan, or D-xylose.
the selection of a strain resulting from the cultivation step following mutagenesis that exhibits a phenotype corresponding to the reduced or inhibited activity of the predetermined part of the carbon metabolism occurs under selection conditions that illustrate the reduced or inhibited activity of the predetermined part of carbon metabolism in comparison to the non mutated host either with or without the nucleic acid cassette such as a reduced zone of clearing upon growth on xylan.

The methods described above can advantageously be carried out with a host characterised in that prior to introduction of the nucleic acid cassette it comprises nucleic acid corresponding at least in part to the nucleic acid sequence encoding the bidirectional marker, said correspondence being to a degree sufficient to allow homologous recombination in the chromosome of the bidirectional marker encoding nucleic acid comprised on the nucleic acid cassette. This aspect ensures the integration of the nucleic acid cassette at a predefined location.

In a further preferred embodiment the nucleic acid cassette will be incorporated in multiple copies to ensure that the mutagenesis step does not inactivate the bidirectional marker as this would result in incorrect results when detecting marker negative phenotypes and a decrease in the number of marker positive phenotypes.

In preferred embodiments of the invention a nucleic acid cassette has been constructed which can be used in a method for producing mutants exhibiting overexpression of an enzyme involved in a predetermined part of metabolism, a method for producing mutants exhibiting reduced or inhibited expression of an enzyme involved in a predetermined part of metabolism and a method for determining and isolating regulatory genes involved in predetermined parts of metabolism. In particular we illustrate the system as used for mutants in carbon metabolism. In the examples mutants with altered xylanolytic characteristics are described as well as arabinase and polygalacturonase mutants leading to mutants in the arabinolytic and pectinolytic pathways. In the examples Aspergillus is used as the strain to be mutated, however any other industrially acceptable microorganism will suffice. Examples of such organisms are *Saccharomyces* e.g. *Saccharomyces cerevisiae*, *Saccharomyces pombe*, *Aspergillus* e.g. *Aspergillus nidulans*, *Trichoderma*, *Penicillium*, *Fusarium Kluyveromyces* and *Lactobacillus*. Other examples will be obvious to a person skilled in the art and a number are also mentioned elsewhere in the description. An overexpressing or nulexpressing strain for a predetermined part of the metabolism can now be produced. We can also determine the identity and nucleic acid sequence of the activating regulator of an inducible enhancer or activator sequence. In particular when such activating regulator is involved in metabolism, more specifically when such activating regulator is involved in a part of metabolism with an enzyme cascade or feed back loop or multiple feed back loops. The nucleic acid sequence of such a regulatory gene can subsequently be used to enhance expression of target genes. Said target gene being a gene that is regulated by the regulatory gene. In a preferred embodiment such a target gene will have a binding site for the expression product of the regulator gene. Combination of a promoter normally associated with a target gene of the regulator with the regulatory gene in an expression cassette said promoter being operably linked to a homologous or heterologous sequence encoding a homologous or heterologous protein or peptide to be expressed can lead to an expression cassette extremely useful for expression of homologous and even heterologous proteins or peptides. The regulator encoding gene can be under control of its native promoter or any other promoter that can be expressed in the host cell of choice. The promoter can be constitutive or inducible, whatever is most desirable for the particular production process. Such a combination expression cassette falls within the scope of the invention as does a vector or a plasmid comprising such a cassette. The degree of expression is no longer restricted by the presence of too small an amount of regulator and thus the degree of expression of the gene to be expressed is much higher than in a corresponding host cell where the gene is expressed under control of the same promoter but without the additional presence of the regulator gene. Such increased expression is preferably achieved in cells of organisms normally comprising components of the part of the metabolic pathway to be influenced. Suitable host cells are filamentous fungi cells. The incorporation of a combined expression cassette of the type just described above in a host cell comprising a target gene of the regulator can lead to increased expression of the target gene or to increased expression of the target genes if multiple target genes are present. Preferably the target gene will be endogenous to the host cell. A host cell comprising the combination expression cassette falls within the scope of the invention.

In the examples the nucleic acid sequence xlnR of the regulator of the xylanolytic pathway xylR is provided. The target genes for this regulator have been found to comprise the genes xlnA, xlnB, xlnC and xlnD as well as axeA. The increase in xylanase A expression is illustrated and can serve to indicate the general applicability of the xylR action on a target gene of the xylR regulator. A number of sequences are known in the state of the art comprising the xlnA, B, C and D genes mentioned and the axeA gene and such information is readily available to a person skilled in the art and is to be considered incorporated herein. The promoters of preferred interest to be used in combination with xlnR nucleic acid can be selected from xlnA, xlnB, xlnC and xlnD. The use of the axeA promoter also forms a suitable embodiment of the invention. The promoters are known in the state of the art to the person skilled in the art, and are considered to be incorporated herein. The xlnA promoter is described in de Graaff et al 1994. The xlnB promoter has been described by Kinoshita et al 1995). The xlnD promoter has been described in EP 952107.7 and is included in the Sequence Listing in the sequence of sequence id no 8 of this document. The promoter sequences can either be readily synthesized on the basis of known sequences or be derived from organisms or vectors comprising them in standard manners known per se. Where the term promoter, enhancer or regulator is used naturally a fragment comprising the promoter, enhancer or regulator can be employed as long as the operability of such is not impaired. It is not necessary in the constructs according to the invention to merely incorporate the relevant sequence, any flanking non interfering sequences can be present. Not only is the nucleic acid sequence xlnR encoding the expression product xylR covered by the subject invention but also sequences encoding equivalent expression products and mutant expression products as well as the expression products themselves of the nucleic acid sequences according to the invention. Any application of xylR or xylR encoding sequences (=xlnR) disclosed herein is also applicable to the mutants and the nucleic acid sequences encoding such mutants and is to be considered incorporated mutatis mutandi.

Examples of suitable fungal cells to be used for expression of nucleic acid sequences and cassettes according to the invention are *Aspergillus* such as *Aspergillus niger*, *Aspergillus tubigensis*, *Aspergillus aculeatus*, *Aspergillus awamori*, *Aspergillus oryzae*, *Aspergillus nidulans*, *Aspergillus carbonarius*, *Aspergillus foetidus*, *Aspergillus terreus*, *Aspergillus sydowii*, *Aspergillus kawachii*, *Aspergillus japonicus* and species of the genus *Trichoderma*, *Penicillium* and *Fusarium*. Other cells such as plant cells are also feasible host cells and elsewhere in the description alternative host cells are also described.

Genes of particular interest for expressing using the expression cassette according to the invention or in combination with a nucleic acid sequence according to the invention are those encoding enzymes. Suitable genes for expressing are genes encoding xylanases, glucanases, oxidoreductases such as hexose oxidase, α-glucuronidase, lipase, esterase, ferulic acid esterase and proteases. These are non limiting examples of desirable expression products. A number of sequences are known in the state of the art comprising the genes mentioned and such information is readily available to the person skilled in the art and is to be considered incorporated herein. The genes can either be readily, synthesized on the basis of known sequences in the literature or databases or be derived from organisms or vectors comprising them in a standard manner known per se and are considered to be knowledge readily available to the person skilled in the art not requiring further elucidation.

An expression product exhibiting 80%-100% identity with the amino acid sequence of xylR according to sequence id no. 9 or as encoded by the nucleic acid sequence of xlnR of sequence id. no. 9 (from nucleotide 948) is considered to be an equivalent expression product of the xylanase regulator (xylR) according to the invention and thus falls within the scope of the invention. The equivalent expression product should possess DNA binding activity. Preferably such DNA binding activity should be such that the expression product binds to the nucleic acid of the target gene to the same degree or better than the expression product binds with the amino acid sequence provided in sequence id no 9. The preferred target genes for determining binding activity are those encoding xylA, xylb, xylC and xylD i.e. the xlnA, xlnB, xlnC and xlnD genes.

Mutants of the xlnR gene expression product xylR and the encoding nucleic acid sequence xlnR according to sequence id no 9 at least maintaining the same degree of target binding activity are also claimed. Mutants considered to fall within the definition of equivalent expression products comprise in particular mutants with amino acid changes in comparison to the amino acid sequence of sequence id no 9. Such equivalents are considered suitable embodiments of the invention as are the nucleic acid sequences encoding them. Mutants with 1-15 amino acid substitutions are suitable and substitutions of for example 1-5 amino acids are also considered to form particularly suitable embodiments of the invention that form equivalent expression products. It is common knowledge to the person skilled in the art that substitutions of particular amino acids with other amino acids of the same type will not seriously influence the peptide activity. On the basis of hydrapathy profiles a person skilled in the art will realise which substitutions can be carried out. Replacement of hydrophobic amino acids by other hydrophobic amino acids and replacement of hydrophilic amino acids by other hydrophilic amino acids e.g. will result in an expression product that is a suitable embodiment of the invention. Such substitutions are considered to be covered by the scope of the invention under the term equivalents. Point mutations in the encoding nucleic acid sequence according to sequence id no 9 are considered to result in nucleic acid sequences that fall within the scope of the invention. Such point mutations can result in silent mutations at amino acid level or in substitution mutants as described above. Substitution mutants wherein the substitutions can be of any type are also covered by the invention. Preferably the identity of the mutant will be 85-100%, more preferably 90-100%, most preferably 95-100% in comparison to the amino acid sequence of sequence id no 9. As already claimed above amino acid sequences exhibiting 80-100% identity with the amino acid sequence of sequence id no 9 are covered by the term equivalent so that deletions and/or substitutions of up to 20% of the amino acid sequence, preferably of less than 15% and more preferably less than 10% most preferably of less than 5% of the amino acid sequence according to the invention are covered. Such a mutant may comprise the deletion and/or substitution in one or more parts of the amino acid sequence. Such a deletion and/or substitution mutant will however comprise an amino acid sequence corresponding to a Zn finger binding region and an amino acid sequence corresponding to the RRRLWW motif (SEQ ID NO: 12). Deletion mutants of 1-5 amino acids are considered to fall within the scope of the invention. Deletion mutants with larger deletions than 5 amino acids and/or with more than 5 substitutions and/or point mutations can also maintain the DNA binding activity. Such larger number of deletions and/or substitutions and/or point mutations will preferably occur in the N terminal half of the amino acid sequence and the corresponding part of the encoding nucleic acid sequence. The most important regions considered to be involved in regulation and activation are present in the C terminal half of the amino acid sequence from the zinc finger binding region and as such the deletion mutants will preferably comprise at least this portion of the amino acid sequence. Preferably no mutation will be present in the zinc finger binding region corresponding to that encoded in sequence id no 9 from nucleotides at position 1110 to 1260. If a mutation is present preferably it should not involve the sparing between the 6 cysteines coordinating the zinc and most preferably any mutation should not involve any of the 6 cysteines themselves. In addition preferably no mutation is present in the RRRLWW motif (SEQ ID NO: 12) present in the amino acid sequence of sequence id no 9. A deletion may occur in one or more fragments of the amino acid sequence. Such a deletion mutant will however comprise an amino acid sequence corresponding to a Zn finger binding region and an amino acid sequence corresponding to the RRRLWW motif (SEQ ID NO: 12). Deletions of 1-15 amino acids, preferably of 1-10 amino acids and most preferably 1-5 amino acids are suitable embodiments to ensure equivalence.

Embodiments of equivalent nucleic acid sequences are a nucleic acid sequence which encodes an expression product having the same amino acid sequence as xylR of sequence id no. 9 or as encoded by the nucleic acid sequence of xlnR of sequence id. no. 9. A nucleic acid sequence encoding an expression product exhibiting 80%-100% identity with the amino acid sequence of xylR according to sequence id no 9 or as encoded by the nucleic acid sequence encoding xylR of sequence id no 9 is also considered to be an equivalent nucleic acid sequence of xlnR and falls within the scope of the invention. Another embodiment of an equivalent nucleic acid sequence according to the invention is a nucleic acid sequence capable of hybridising under specific minimum stringency conditions as defined in the Examples to primers or probes derived from nucleic acid sequence id no 9, said primers or probes being derived from the non zinc finger binding region and said primers or probes being at least 20 nucleotides in length. Generally suitable lengths for probes and primers are between 20-60 nucleotides, preferably 25-60. Preferably a probe or primer will be derived from the C-terminal encoding half of the sequence of id no 9 from the zinc finger binding region. A preferred embodiment of a nucleic acid sequence according to the invention will be capable of hybridising under specific conditions of at least the stringency illustrated in the examples to the nucleic acid sequence of id no 9. An equivalent nucleic acid sequence will be derivable from other organisms by e.g. PCR using primers based on the nucleic acid sequence id no 9 as defined above. An expression product of an equivalent nucleic acid sequence as just defined is also considered to fall within the scope of the invention. Vice versa a nucleic acid sequence encoding an equivalent amino acid sequence according to the invention is also considered to fall within the scope of the term equivalent nucleic acid sequence. In particular equivalent nucleic acid sequences and the expression products of such sequences derivable from filamentous fungi and plants are preferred embodiments of the invention. Preferably an equivalent nucleic acid sequence will comprise a nucleic acid sequence encoding a zinc finger binding region corresponding to that encoded in sequence id no 9 from nucleotides from position 1110 to 1260. In a preferred embodiment the equivalent nucleic acid sequence should encode the 6 cysteines coordinating the zinc. In a further embodiment the spacing between the cysteines should correspond to that of sequence id no 9.

Embodiments comprising combinations of the characteristics of the various embodiments of the equivalent nucleic acid sequences and expression products, described above also fall within the scope of the invention. Mutants with mutation in the zinc finger binding domain are also claimed as these could exhibit increased DNA binding. Mutants exhibiting decreased DNA binding are also considered to fall within the scope of the invention. Such mutants may possess a mutation in the zinc finger binding domain. In particular mutants of the amino acid sequence provided in sequence id no 9 are claimed.

Fragments of the nucleic acid sequence according to sequence id no 9 of at least 15 nucleotides also fall within the scope of the subject invention. Such fragments can be used as probes or primers for detecting and isolating equivalent sequences. In particular a combination of two or more such fragments can be useful in a kit for detecting and/or isolating such equivalent sequences. Preferably a fragment will be derived from the C terminal half of the amino acid sequence of sequence id no 9. In a suitable embodiment of the kit one fragment will not comprise a part of the nucleic acid sequence forming the zinc finger domain. In the examples a suitable combination of fragments to be used as primers is illustrated. Any sequence obtainable through PCR as illustrated in the examples with these primers is considered to fall within the scope of the invention. The hybridisation conditions used in the examples provide the minimum stringency required for selectivity. More stringent conditions can be applied such as the stringent hybridisation conditions described by Sambrook et al for increased homology of the obtained sequences with the sequence id no 9. A lower salt concentration generally means more stringent conditions. Any fragment of the sequence according to sequence id no 9 being or encoding a polypeptide exhibiting the target gene binding activity of the complete sequence is also included within the scope of the invention as are equivalent nucleic acid sequences or amino acid sequences thereof, with equivalent being defined as defined above with regard to hybridisation and/or mutation and/or degeneracy of the genetic code for the complete sequence.

A vector or plasmid comprising the nucleic acid sequence encoding xylR or an equivalent sequence thereof as defined above also falls within the scope of the invention, as do a vector or plasmid comprising such a sequence and a host cell comprising such an additional sequence. A transformed host cell such as a microorganism or a plant cell carrying at least one additional copy of an encoding nucleic acid sequence according to sequence id no 9 or an equivalent thereof falls within the scope of the invention. Preferably the various embodiments are organised such that the sequence can be expressed in the vector, plasmid or host cell. The regulatory gene can comprise the complete sequence of id no 9 or merely the encoding sequence thereof in combination with an alternative promoter that is operable in the host cell. Suitable examples of host cells have been provided elsewhere in the description. Suitable operable promoters for the various host cells that can be incorporated with the encoding sequence of sequence id no 9 will be clear to a person skilled in the art. In particular for the host cells explicitly mentioned in the description constitutive promoters or inducible promoters are known and available to work the invention without undue burden.

A process for production of homologous or heterologous proteins or peptides is provided, said process comprising expression of a nucleic acid sequence encoding the homologous protein or peptide in a host cell, said host cell further comprising an additional copy of a nucleic acid sequence encoding a regulatory gene such as xlnR or an equivalent thereof which is also expressed. A process as just described is preferably carried out with a combination nucleic acid expression cassette comprising the regulatory gene operably linked to a first promoter and said cassette further comprising a second promoter, said second promoter normally being associated with a target gene of the regulator, said target gene promoter being operably linked to the nucleic acid sequence encoding the homologous or even heterologous protein or peptide to be expressed. The first promoter can be the promoter natively associated with the regulator gene but may also be a promoter of choice that is operable in the host cell. The degree of expression is no longer restricted by the presence of too small an amount of regulator and thus the degree of expression of the gene to be expressed is much higher than in a corresponding host cell where the gene is expressed without the additional presence of the regulator gene. Such increased expression is preferably achieved in cells of organisms normally comprising components of the part of the metabolic pathway to be influenced. Suitable host cells are a plant cell or a microorganism, suitably the microorganism can be a fungus in particular it can be a filamentous fungus. Examples of suitable host cells have been given elsewhere in the description and may be considered to be incorporated here. The incorporation of a combined expression cassette of the type just described above in a host cell comprising a target gene of the regulator can lead to increased expression of the target gene or to increased expression of the target genes if multiple target genes are present. Preferably the tar et gene will be native to the regulator. Preferably such a target gent will be endogenous to the host cell. In the examples the nucleic acid sequence of the regulator of the xylanolytic pathway xlnR is provided. The native target genes for this regulator have been found to comprise the genes xlnA, xlnB, xlnC and xlnD as well as axeA and as such these genes are preferred target genes. Other targets exist and are considered to be included in the term target gene. Various embodiments of the host cells according to the invention are covered in the claims. If both regulator sequence and target gene are natively present in the host cell the regulator sequence will be present in multiple copies. Such a microorganism will over express the gene regulated by the target gene promoter in comparison to the native microorganism.

Because now the sequence for the xylanase regulator is known it has become possible to knock out the xylanase regulator. The creation of a knockout host cell once the nucleic acid sequence of the gene to be knocked out is known is standard technology. This method can be carried out analogously to that described in Berka et al (1990) and example 11 of EP 95201707.7, which is a copending European patent application of which a copy has been included upon filing the subject document and the example itself has also been copied into this document in the examples. Such a knockout renders a host cell which can be free of xylanolytic activities. A host cell free of xylanolytic activity due to knocking out the xlnR gene can be used to produce homologous or heterologous expression products of choice free of xylanolytic activity. A host cell with a knocked out xlnR gene falls within the scope of the invention. Such a host cell is preferably a plant cell or a filamentous fungus. Such a filamentous fungus is preferably an *Aspergillus*. Examples have been provided elsewhere in the description of numerous suitable host cells.

A host cell with a mutation in the regulator gene which can be arrived at using the selection and mutation method of the invention can be subjected to complementation with a regular active copy of the regulator gene. Such a complemented strain will subsequently express the products of any target genes that are regulated by the regulator. These target gene products will be absent in the case of the non complemented regulator negative mutant. Upon comparison of protein bands obtained in a manner known per se from both of the strains it will become apparent what target products are regulated by the regulator and subsequently the corresponding novel target genes can be determined in a manner known per se once its expression product has been determined. In this manner other target genes than those already known can be found for the xylanase regulator xylR in the instant examples.

EXAMPLES

Example 1

Construction of the Plasmids

Example 1.1

Construction of the Selection Plasmid pIM130

The selection plasmid pIM130 was constructed as depicted in FIG. 1. In PCR1 a fragment was generated from the plasmid pIM120 (de Graaff et al. 1994) using oligonucleotide 1 (SEQ ID NO: 1)

5'-CACAATGCATCCCCTCTATCCGCCTGCCGT-3' (Formula 1)

and oligonucleotide A (SEQ ID NO: 2)

5'-CAAMTrGCGACITGGAGGACAT-
GATGGGCAGATGAGGG-3' (Formula 2)

Oligonucleotide 1 was derived from the *Aspergillus tubigensis* xlnA promoter (de Graaff et al. 1994) positions 600-619 (SEQ ID NO: 5) to which 10 nucleotides containing a NsiI site were added. The 3' end of oligonucleotide A was derived from the *Aspergillus niger* goxC transcription unit (Whittington et al., 1990) ending just before the translation initiation site (positions 708-723)(SEQ ID NO: 6), while the 5' end was derived from the coding region of the *A. niger* pyrA gene (Wilson et al., 1988) (starting at the translation initiation site (positions 341 to 359. SEQ ID NO: 7).

Fragment A was generated by a PCR containing 10 μl 10*reaction buffer (100 mM Tris-HCl, pH 8.3, 500 mM KCl. 15 mM MgCl$_2$, 0.01% gelatin). 16 μl 1.25 mM of each of the four deoxynucleotide triphosphates, 1 ng of the plasmid pIM120 DNA and 1 μg of each of the oligonucleotides 1 and A in a final volume of 100 μl. This reaction mixture was mixed and 1 μl TAQ polymerase (5 U/μl) (Life Technologies) was added. The DNA was denatured by incubation for 3 min at 92° C. followed by 25 cycli of 1 min 92° C. 1 min 48° C. and 1 min 72° C. After these 25 cycli the mixture was incubated for 5 min at 72° C. Analysis of the reaction products by agarose electrophoresis revealed a fragment of about 250 bp, which corresponds to the size expected based on the sequence of the genes.

In PCR2 a fragment was generated from the plasmid pGW635 (Goosen et al., 1987) using oligonucleotide 2 (SEQ ID NO: 3)

5'-AGAGAGGATATCGATGTGGG-3' (Formula 3)

and oligonucleotide B (SEQ ID NO: 4)

5'-CCCTCATCTGCCCATCATGTCCTC-
CAACTCGCAATM-3' (Formula 4)

The 5' end of oligonucleotide B was derived from the *A. niger* goxC basic transcription unit (positions 708-723, SEQ ID NO:6)(Whittington et al., 1990)$_3$ while the 3' end was derived from the coding region of the *A. niger* pyrA gene starting at the translation initiation site. Oligonucleotide 2 was derived from the pyrA coding region (positions 339-359. SEQ ID NO:7) and is spanning an EcoRV restriction site at position 602 (SEQ ID NO:7).

Fragment B was generated in an identical manner as fragment A except that in this case the reaction mixture contained 1 μg each of oligonucleotide 2 and B and 1 ng of plasmid pGW635 DNA. Analysis of the reaction products by agarose electrophoresis revealed a fragment of about 250 bp, which corresponds to the size expected based on the sequence of the pyrA gene.

Fragments A and B were isolated from agarose gel after electrophoresis. The fragments were cut from the agarose gel, after which they were recovered from the piece of agarose by electro-elution using ISCO cups. Both on the large and the small container of this cup a dialysis membrane was mounted, the cup was filled with 0.005×TAE (50×TAE buffer per 1000 ml: 242.0 g Trizma base (Sigma). 7.1 ml glacial acetic acid, 100 ml 0.5 M EDTA pH 8.0) and the piece of agarose was placed in the large container of the cup. Subsequently the cup was placed in the electro-elution apparatus, with the large container in the cathode chamber containing 1*TAE and the small container at the anode chamber containing 1*TAE/3 M NaAc. The fragments were electro-eluted at 100 V during 1 h. After this period the cup was taken from the electro-elution apparatus and the buffer was removed from the large container, while from the small container the buffer was only removed from the upper part. The remaining buffer (200 μl) containing the DNA fragment was dialyzed in the cup against distilled water during 30 min. Finally the DNA was precipitated by the addition of 0.1 vol. 3 M NaAc, pH 5.6 and 2 vol. cold (−20° C.) ethanol. The DNA was collected by centrifugation (Eppendorf centrifuge) for 30 min. at 14,000×g. at 4° C. After removal of the supernatant the DNA pellet was dried using a Savant Speedvac vacuum centrifuge. The DNA was dissolved in 10 μl TE buffer (TE: 10 mM Tris/HCl pH 7.2, 1 mM EDTA pH 8.0) and the concentration was determined by agarose gel electrophoresis, using lambda DNA with a known concentration as a reference and ethidiumbromide staining to detect the DNA.

Fragments A and B were fused in PCR3 which was identical to PCR1 except that in this case the reaction mixture contained 1 μg of each of the oligonucleotides 1 and 2 and approximately 50 ng of each of the fragments A and B. Analysis of the reaction products by agaoste gel electrophoresis revealed a fragment of about 500 bp, which corresponds to the size expected based on the sequences of the genes.

The resulting fragment C was isolated from agarose gel as described and subsequently digested using the restriction enzymes NsiI and EcoRV. The DNA was digested for 3 h. at 37° C. in a reaction mixture composed of the following solutions; 5 µl (≈0.5 µg) DNA solution; 2 µl of the appropriate 10× React buffer (Life Technologies); 10 U restriction enzyme (Life Technologies) and sterile distilled water to give a final volume of 20 µl. After digestion the DNA fragment was analysed by agarose gel electrophoresis and subsequently isolated from the gel as described.

For the final construction of pIM1305 µg of the plasmid pGW635 was digested as described using 50 U of the restriction enzymes EcoRV and XbaI in a final volume of 500 µl. After separation of the products a 2.2 kb EcoRV/XbaI fragment (fragment D) was isolated from the agarose gel by electro-election. Analogously 1 µg vector pGEM-7Zf(+) (Promega) was prepared by digestion with the restriction enzymes NsiI/XbaI, which was after digestion electrophoresed and isolated from the agarose gel by electro-elution.

The plasmid pIM 130 was constructed by the following ligation reaction: 100 ng pGEM-7Zf(+) NsiI/XbaI fragment was mixed with 50 ng fragment C and 50 ng fragment D and 4 µl 5*ligation buffer (composition; 500 mM Tris-HCl, pH 7.6; 100 mM $MgCl_2$; 10 mM ATP; 10 mM dithiotreitol; 25% PEG-6000) and 1 µl (1.2 U/µl) $T_4$ DNA ligase (Life Technologies) was added to this mixture in a final volume of 20 µl. After incubation for 16 h at 14° C. the mixture was diluted to 100 µl with sterile water. 10 µl of the diluted mixture was used to transform $E.\ coli$ DH5α competent cells, prepared as described by Sambrook et al. 1989.

Two of the resulting colonies were grown overnight in LB medium (LB medium per 1000 ml: 10 g trypticase peptone (BBL), 5 g yeast extract (BBL), 10 g NaCl, 0.5 mM Tris-HCl pH 7.5) containing 100 µg/ml ampicillin. From the cultures plasmid DNA was isolated by the alkaline lysis method as described by Maniatis et al. (1982), which was used in restriction analysis to select a clone harbouring the desired plasmid pIM130. Plasmid DNA was isolated on a large scale from 500 ml cultures $E.\ coli$ DH5α containing pIM130 grown in LB medium containing 100 µg/ml ampicillin (Maniatis et al., 1982) The plasmid was purified by CsCl centrifugation, phenolyzed, ethanol precipitated and dissolved in 400 µl TE. The yield was approximately 500 µg.

Example 1.2

Construction of the Plasmid pIM135

From the plasmid pIM120 a second plasmid was constructed which contains the goxC basic transcription unit fused to the pyrA coding region and termination region. In PCR4 a fragment was generated from the plasmid pIM120 using oligonucleotide 3, 5'-CACAATGCATCGTATAAG-TAACCTCGTTCG-3' (Formula 5) (SEQ ID NO:10) which was derived from the goxC basic transcriptional unit (positions 640-660, SEQ ID NO:6) to which 10 nucleotides containing a NsiI site were added, and oligonucleotide 2 (Formula 3). The fragment generated was isolated from gel, digested with NsiI and EcoRV and cloned together with the 2.2 kb EcoRV/XbaI fragment of pGW635 in the plasmid pGEM-7Zf(+), which was digested with XbaI/NsiI, as described in Example 1.1., resulting in the plasmid pIM135.

The plasmid pIM135 can be used as construction vehicle for preparing vectors according to the invention with any desirable inducible enhancer or activator sequence, a UAS of a gene involved in metabolism. pIM135 comprises a basic transcription unit (tGOX) operatively linked to a bidirectional marker gene (pyrA).

Example 2

Transformation of $A.\ niger$ Using the Plasmid pIM130

250 ml of culture medium, which consists of Aspergillus minimal medium (MM)(contains per liter: 6.0 g $PaNO_3$. 1.5 g $KH_2PO_4$, 0.5 g $MgSO_4.7H_2O$, 0.5 g KCl, Carbon source as indicated, pH 6.0 and 1 ml Vishniac solution (contains per liter 10 g EDTA. 4.4 g $ZnSO_4.7H_2O$, 1.0 g $MnCl_2.4H_2O$, 0.32 g $CoCl_2.O.6H_2O$, 0.32 g $CuSO_4.5H_2O$, 0.22 g $(NH_4)_6M_7O_{24}.4H_2O$. 1.47 g $CaCl_2.2H_2O$, 1.0 g $FeSO_4.7H_2O$, pH 4.0) supplemented with 2% glucose. 0.5% Yeast Extract, 0.2% Casamino acids (Vitamin free). 10 mM L-arginin. 10 µM nicotinamide, 10 mM uridine, was inoculated with $1*10^6$ spores per ml of strain NW205 (cspA1, pyrA6, nicA1, argB13) and mycelium was grown for 16-18 hours at 30° C. and 250 rpm in a orbital New Brunswick shaker. The toycelium was harvested on Myracloth (nylon gauze) using a Büchner funnel and mild suction and was washed several times with SP6 (SP6: 0.8% NaCle 10 mM Na-phosphate buffer pH 6.0). 150 mg Novozyme 234 was dissolved in 20 ml SMC (SMC: 1.33 M Sorbitol. 50 mM $CaCl_2$, 20 mM MES buffer, pH 5-8) to which 1 g (wet weight) mycelium was added and which was carefully resuspended. This suspension was incubated gently shaking for 1-2 hours at 30° C. every 30 minutes the mycelium was carefully resuspended and a sample was taken to monitor protoplast formation using a haemocytometer to count the protoplasts. When sufficient protoplasts were present (more then $1*10^8$) these were carefully resuspended and the mycelial debris was removed by filtration over a sterile glasswool plug. The protoplasts were collected by 10 minutes centrifugation at 3000 rpm and 4° C. in a bench centrifuge and were carefully resuspended in 5 ml STC (STC: 1.33 M Sorbitol, 50 mM $CaCl_2$, 10 mM Tris/HCl, pH 7.5). This wash step was repeated twice and the protoplasts were finally resuspended in STC at a density of $1*10^8$ per ml.

The transformation was performed by adding 1 µg of pIM130 DNA (dissolved in a 10-20 µl TE to 200 µl of protoplast suspension together with 50 µl of PEG buffer (PEG Buffer: 25% PEG-6000, 50 mM $CaCl_2$, 10 mM Tris/HCl pH 7.2), mixed gently by pipetting up and down a few times, and incubated at room temperature for 20 minutes. After this period 2 ml PEG buffer was added, the solution was mixed gently and incubated at room temperature for another 5 minutes and subsequently 4 ml of STC was added and mixed gently on a vortex mixer. This was also done using 5 µg pIM130 and 1 and 5 µg of plasmid pGW635 DNA. As a negative control 20 µl of TE was added to the protoplasts.

One ml portions of this suspension were then added to 4 ml of osmotically stabilised top agar and poured on plates (swirl gently to cover plate with top agar) containing MMS having either 100 mM D-glucose or 100 mM D-xylose as a carbon source. These media (MMS) were osmotically stabilised using 0.8 M KCL or by using 1.33 M Sorbitol.

To determine the percentage regeneration serial dilutions of the protoplasts were prepared before transformation (untreated protoplasts, kept on ice) and, after transformation (obtained from the negative control). 100 µl of the $10^{-3}$, $10^{-4}$, $10^{-5}$ and $10^{-6}$ dilutions were plated in duplicate on 10 mM uridine supplemented MMS plates.

For the positive control, in which the fungus was transformed using the plasmid pGW635, colonies were found on all plates. However, the transformation frequency was much lower (1-10 transformants per µg plasmid DNA) on KCl stabilised medium than on sorbitol stabilised medium (100-

1000 transformants per μg plasmid DNA). This was due to the much higher regeneration frequency on the latter medium, which was about 90Z in comparison to 2-5% on the KCl stabilised medium.

In case of the transformations using the plasmid pIM130 transformants were found on the medium containing D-xylose as a carbon source but not on medium containing D-glucose. The frequency on sorbitol stabilised medium was about 100 per μg of plasmid DNA while the frequency on the KCl stabilised medium was less than one per μg of DNA.

Example 3

Analysis of Transformants

The transformants from pIM130 obtained in Example 2 were analysed phenotypically by plating on MM containing 100 mM D-glucose, 100 mM D-glucose/1% Oat spelt xylan (Sigma #X0627) and 1% Oat spelt xylan. A selection of the transformants were replica plated to these media and incubated at 30° C. About 75% of the transformants were growing on xylan containing medium, while no growth was found on media containing D-glucose. The remaining 25% of the colonies grew on all three media tested.

A selection of five transformants having the expected phenotype (growth on xylan containing medium, non-growth on D-glucose containing media) was analysed by Southern analysis. Fungal DNA was isolated by a modified procedure used to isolate plant RNA essentially as described by de Graaff et al., 1988). Mycelium, which was grown overnight in culture medium, was harvested, washed with cold saline, frozen in liquid nitrogen and stored at −80° C. Nucleic acids were isolated by disrupting 0.5 g frozen mycelium using a microdismembrator (Braun). The mycelial powder obtained was extracted with freshly prepared extraction buffer. The extraction buffer was prepared as follows: 1 ml tri-isopropyl-naphtalene sulfonic acid (TNS) (20 mg/ml) was thoroughly mixed with 1 ml p-aminosalicylic acid (PAS) (120 mg/ml) and 0.5 ml 5×RNB buffer was added (5×RNB contains 121.10 g Tris, 73.04 g NaCl and 95.10 g E=TA in 1 μl, pH 8.5). After the addition of 1.5 ml phenol, the extraction buffer was equilibrated for 10 min. at 55° C. The warm buffer was then added to the mycelial powder, and the suspension was thoroughly mixed for 1 min. using a vortex mixer. After addition of 1 ml chloroform the suspension was remixed for 1 min. After centrifugation at $10^4$×g for 10 min. using a Sorvall high speed centrifuge, the aqueous phase was extracted once more with an equal volume of phenol/chloroform (1:1) and was then extracted twice with chloroform. DNA was isolated from the aqueous phase using the following procedure; the DNA was immediately precipitated from the aqueous phase with 2 vol. ethanol at room temperature and subsequently collected by centrifugation using a Sorvall high speed centrifuge at $10^4$×g for 10 min. and washed twice by redissolving the DNA in distilled, sterile water and precipitating it again with ethanol. RNA was removed by adding RNase A (20 g μg/ml) to the final solution.

High molecular weight DNA (1-2 μg) isolated from *A. niger* N402 (cspA1) as a wild-type and five pIM130 transformants as described wa digested with Rpal (Life Technologies) according to the manufactors instructions. The resulting fragments were separated by agarose gel electrophoresis, and transferred to High-bond N membrane as described by Maniatis et al. (1982). Hybridisation using a $^{32}$P-labelled 3.8 kb XbaI fragment, prepared as described by Sambrook et al., 1989, containing the *A. niger* pyrA gene as a probe was done according to the following procedure (Sambrook et al.; prehybridization in 6×SSC (20×SSC per 1000 ml: 175.3 g NaCl. 107.1 g sodium citrate. 5.5H$_2$O, pH 7.0), 0.1% SDS, 0.05% sodium pyrophosphate. 5*Denhardt's solution (100×Denhardts solution per 500 ml:10 g Ficoll-400, 10 g polyvinylpyrolidone. 10 g Bovine Serum Albumin (Pentax Fraction V) and 20 μg/ml denatured herring sperm DNA at 68° C. for 3-5 hrs and hybridization in an identical buffer which contained the denatured radiolabelled probe at 68° C. for 15-18 hrs. followed by two washes in 3×SSC. 0.1% SDS at 68° C. and two washes in 0.2×SSC, 0.1% SDS at 68° C. The membrane was covered with Saran wrap and autoradiographed overnight at −70° C. using Konica X-ray films and Kodak X-Omatic cassettes with regular intensifying screens.

As a result a 10 kb hybridising band is found in the N402 lane, while this band is missing in the transformants NW205:: 130#1. NW205::130#2 and NW205::130#3. In the transformants NW205::130#1 and NW205::130#3 a 15 kb hybridising fragment is found, while in NW205::130#2 a 20 kb band is found. These results correspond respectively to a single and a double copy integration at the homologous pyrA locus. In the transformants NW205::130#4 and NW205::130#5 the plasmid was integrated at a non-homologous locus. Transformant NW205::130#2 was selected for mutagenesis.

The UAS fragment of pIM130 comprises the binding site required for the positive regulator to exhibit the stimulatory activity of the UAS. Thus inhibition of xlnR in the host cell comprising pIM130 will result in negative expression of the bidirectional marker present on pIM130. Expression of xlnR is induced by xylan or xylose. Thus the presence of such substrates should result in expression of the bidirectional marker of pIM130 if the host possesses xlnR.

The UAS fragment of pIM130 does not comprise the site required for inhibitory activity of creA that is present on the native UAS of the *Aspergillus niger* xlnA gene. Thus the presence of glucose which renders *A. niger* CRE A$^+$ and subsequently inhibits the UAS of xlnA and the other xylanolytic enzyme encoding genes such as xlnD and axeA and also inhibits the xlnR gene encoding the activator of the UAS of the aforementioned xylanolytic enzyme encoding genes i.e. represses xylanolytic enzyme expression which results in negative expression of pIM130.

Example 4

Selection of Mutants

Example 4.1

Selection of Derepressed Mutants

Spores of NW205::130N2 were harvested in 5 ml ST (ST: 0.8% NaCle 0.05% Tween 20), shaken at high frequency and mycelial debris was removed by filtration over a sterile glasswool plug. The spores were collected by centrifugation for 10 minutes at 3000 rpm at room temperature in a bench centrifuge and were resuspended in 5 ml saline. This wash step was repeated twice and the spores were finally resuspended in saline at a density of 1*10$^7$ per ml. 10 ml of the spore suspension was dispensed in a glass petridish and was irradiated using UV at a dosage of 18 erg/mm$^2$/min for 2 min. After mutagenesis 105 and 106 spores were plated (10 plates each) on MM+10 mM L-arginine+10 μM nicotinamide containing 3% D-glucose and on plates containing 3% D-glucose/3% oat spelts xylan (Sigma #X0627).

After 4-7 days 5-10 mutant colonies per plate (106 spores inoculated) were found which on basis of their morphology could be divided into three classes; large, well sporulating colonies, intermediate sized, well sporulating colonies and small poorly sporulating colonies. A random selection of 20 of these mutants was made and the selected mutants were tested on media containing different carbon sources or substrates. The mutant colonies were found to be able to grow on media containing D-glucose. D-glucose/xylan and xylan, while the parental strain NW205::130#2 only was able to grow on medium containing xylan as a carbon source. In addition these mutants were tested on different chromogenic substrates; 4-methylumbelliferyl-β-D-xyloside (β-xylosidases, endoxylanases) (Sigma #M7008). 4-methylumbelliferyl acetate (acetyl-xylan esterases)(Sigma #M0883). 4-methylumbelliferyl-α-L-arabinofuranoside (arabinofuranosidases) (Sigma IM9519) and on Remazol Brilliant blue modified xylan (endo-xylanases)(Sigma #M5019). The methylumbelliferyl derivatives were added in a 1 mM final concentration to media containing D-glucose. D-glucose/xylan and xylan, while the RBB-xylan was added in a concentration of 1 mg/ml to media containing D-glucose/xylan and xylan, For all these substrates tested enzyme activity was found in the mutants after growth on D-glucose containing media, while no expression was found in the parental strain NW205::pIM130#2. On media containing Xylan an, increased expression of these enzymes was found in comparison to NW205::pIM130. Of the mutants tested mutant 5 B had the highest expression levels. In the instant case selection occurred on a substrate normally active as inhibitor of xylanolysis i.e. glucose. To be certain that expression could occur in the absence of repression an inducer of xylanolytic genes xylan was also included. Such a control test is preferably included in a method according to the invention. The mutant clearly exhibited derepression.

Figure 2:
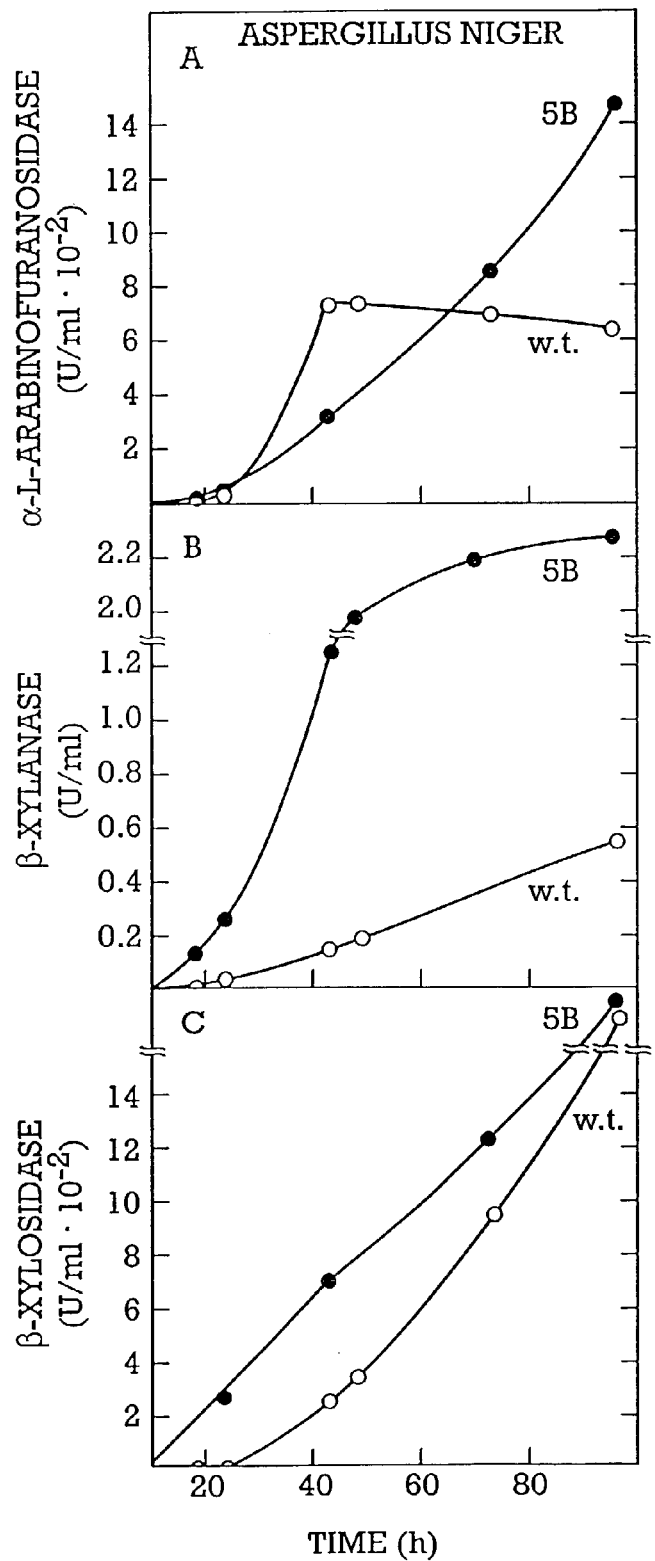
FIG. 2 depicts a comparison of the activity levels of α-L-arabinofuranosidase, β-xylanase and β-xylosidase in wild-type ("w.t.") *A. niger* N402 and mutant strain 5B ("5B") cultured on MM containing 1.5% crude wheat arabinoxylan as a carbon source.

For the comparison of the activity levels produced, both *A. niger* N402 and mutant 5B were cultured on MM containing 1.5% crude Wheat arabinoxylan as a carbon source. Samples were taken at 24, 42, 72 and 96 hrs and the activities of α-L-arabinofuranosidase, endo-xylanase and β-xylosidase were measured. The results (FIGS. 2A, B, C) indicated an increase in activity for the mutant strain for all three enzymes. α-L-arabinofuranosidase and endo-xylanase activity was most strongly increased.

Example 4.2

Selection of Non-Expressing Mutants

Spores of strain NW205::130#2 were harvested and mutated as described in Example 4.1 and subsequently plated on MM containing 100 mM D-xylose supplemented with 10 mM uridine, 10 mM L-arginin and 0.8 mg/ml 5-fluoroorotic acid (Sigma #F5013). These plates were incubated for 4-7 days at 30° C. 64 of the growing colonies, having a PYR⁻ phenotype, were analysed for xylanase expression by plating on MM containing 1% xylan+10 mM uridine+10 nM L-arginin+10 μM nicotinamide. Of these 64 mutants tested 10 gave a reduced zone of clearing on these xylan containing plates and had potential reduced xylanase levels. The phenotype of these mutants was verified on D-glucose, D-glucose/xylan and xylan containing media in the presence and absence of uridine. All 10 mutants did not grow on media without uridine.

For further analysis these mutants were precultured 18 hrs at 30° C. on MM containing 50 mM fructose+10 mM uridine+10 mM L-arginin+10 μM nicotinamide after which the mycelium was harvested and 1 g wet mycelium was transferred to MM containing 1% xylan and to MM containing 10 mM D-xylose+10 mM uridine+10 mM L-arginine+10 VM nicotinamide. After 5.5 hrs incubation at 30° C. both the mycelium and the culture filtrate were harvested. The culture filtrate was dialysed against 1 mM NaP$_i$ pH 5.6 after which the xylanese (Bailey et al. (1991)) was determined and β-xylosidase activities were determined (Table 1). Both the xylanase as well as the β-xylosidase expression levels were found to be strongly reduced in these selected mutants.

|  | endo-xylanase | | β-xylosidase | | α-L-arabinofuranosidase | |
|---|---|---|---|---|---|---|
| Activity Strain | xylan (nkat ml⁻¹) | xylose (nkat ml⁻¹) | xylan (nkat ml⁻¹) | xylose (nkat ml⁻¹) | xylan (nkat ml⁻¹) | xylose (nkat ml⁻¹) |
| NW205 | $5 * 10^2$ | $5 * 10^2$ | 0.35 | 0.40 | 0.33 | 0.37 |
| NW205::130 | $5 * 10^2$ | $1 * 10^2$ | 0.36 | 0.51 | 0.40 | 0.29 |
| NW205::130 2Ac2-15 | $5 * 10^2$ | $1 * 10^2$ | 0.26 | 0.30 | 0.30 | 0.23 |
| NW205::130 Ac1-4 | 2 | 1 | 0.01 | 0.01 | 0.36 | |
| NW205::130 Ac4-4 | 2 | 0.3 | 0.01 | 0.01 | 0.214 | |
| NW205::130 Ac4-6 | 2 | 0.3 | 0.01 | 0.01 | 0.31 | |
| NW205::130 Ac3-14 | 1 | 0.4 | 0.01 | 0.01 | 0.29 | |
| NW205::130 Ac4-8 | 2 | 0.4 | 0.01 | 0.01 | 0.38 | |
| NW205::130 Ac2-10 | 1 | 0.1 | 0.01 | 0.01 | 0.19 | |
| NW205::130 Ac2-8 | 1 | 0.3 | 0.01 | 0.01 | 0.29 | |
| NW205::130 Ac2-5 | 1 | 0.2 | 0.01 | 0.01 | 0.28 | |
| NW205::130 Ac1-15 | 2 | 0.2 | 0.01 | 0.01 | 0.23 | |
| NW205::130 Ac4-14 | 2 | 0.2 | 0.01 | 0.01 | 0.28 | |

Example 5

Complementation of Non-Expressing Mutants 5.1 Construction of an *A. niger* Genomic Plasmid Library For the construction of a plasmid library 10 μg of genomic DNA of *A. niger* NW128 (cspA1, nicA1, pyrA6, goxC17), isolated as described in Example 3, was partially digested for 30 min at 37° C. according to the manufactors instructions using 3.5 U Sau3A (Life-Technologies) in a final volume of 100 μl. After separation of the fragments by agarose electrophoresis, fragments ranging in size from 6.7 kb to 9.4 kb were cut from the low melting point agarose gel and were isolated as described in Sambrook et al., (1989). From totally 6 digestions 4 μg of fragments were isolated in a final concentration of 100 ng/μl. 600 ng of the resulting fragments were ligated in 100 ng BamHI digested pUC18 (Pharmacia #27526201) according to the manufacturers instructions. After ligation 4 μl of the resulting ligation mixture was used to transform 100 μl *E. coli* DH5α Max Efficiency competent cells (Life Technologies #18258-012) according to the manufactors instructions. Six subsequent transformation experiments resulted in about 5*104 colonies. After resuspension of these colonies and growth for 3 hrs at 37° C. in TY medium (medium per 100 ml: 16 g Select Peptone 140 (Life Technologies), 10 g NaCl and 10 g Yeast extract) containing 100 μg/ml Ampicillin, plasmid DNA was isolated and purified by CsCl centrifugation.

5.2 Complementation of Non-Expressing Mutants

For the complementation in non-expressing mutants a selection of three mutants, NW205::130 Ac1-4, NW205::130 Ac1-15 and NW205::130 Ac4-4, protoplasts were prepared of these strains and transformed as described in Example 2. In these transformation experiments 108 protoplasts were used and combined with; 20 μg DNA of the A. niger plasmid library as described in Example 5.1, and with 10 μg DNA of the plasmid library combined with 10 μg DNA of the autonomouly replicating plasmid pHEL1 (Gems and Clutterbuck, 1993) and with 20 μg DNA of the plasmid library combined with 10 μg DNA of the autonomously replicating plasmid pHE1. As a positive control 2 μg pGW635 was used. After the transformation procedure the mixtures were plated on MM stabilised with 1.33 M Sorbitol containing 50 mM D-xylose as a carbon source supplemented with 10 μM nicotinamide and 10 mM L-arginin. After about 4 days colonies appeared on the positive control plates and were counted, while after 6 days colonies could be picked from the complementation plates.

The resulting transformant colonies were analysed by plating on medium containing 1% Oat spelt xylan. 1 mM 4-methylumbellyferyl-β-D-xyloside, 10 μM nicotinamide and 10 mM L-arginin. After 6-7 hrs incubation at 30° C. xx fluorescent colonies were detected. After 2-3 days a clearing of the xylan around these colonies appeared.

Example 6

Cloning of the A. niger xlnR Gene

Example 6.1

Isolation of the A. niger xlnR Gene

The A. niger xlnR gene was isolated from transformants obtained and selected as described in Example 5.2. From 13 transformants obtained from NW205::130 Ac 1-4. NW205::130 Ac 1-15 and NW205::130 Ac 4-4 total DNA was isolated, as described by de Graaff et al., 1988. After mycelium was cultured under selective (i.e. inducing) conditions for pyrA and xylanolytic expression on 1.5% crude wheat arabinoxylan as C source from which free replicating plasmids were isolated using Nucleobond AX100 columns (Macherey & Nagel). 200 μg of total DNA dissolved in 400 μl of sterile water was mixed with 2 ml of S1 buffer (50 mM Tris-HCl pH 8.0, 10 mM EDTA, 100 μg RNase A), 2 ml of S2 (200 mM NaOH. 1% SDS), followed by an incubation at room temperature for 5 minutes, and 2 ml of S3 (2.60 M KAc, pH 5.2), followed by an incubation on ice for 5 minutes. After clearing of the suspension at 15.000 g for 30 minutes adsorption, washing, elution and precipitation of the plasmids was done all according to the manufacturers' instructions for "working procedure for the purification of plasmids and cosmids" (5.3 modified alkaline/SDS lysis). 20 μl of the resulting plasmid DNA, dissolved in 150 μl sterile water was used in E. coli DH5α transformation. (Sambrook et al., 1989). 12 E. coli colonies resulting from each of these plasmid preparations were grown for 9-12 hrs at 37° C. in 250 ml LB medium containing 50 μg/ml Ampicillin, after which a miniprep plasmid DNA isolation was performed on 1.5 ml of the culture as described for the boiling lysis protocol by Sambrook et al., 1989 and the cells were pelleted by centrifugation and stored at −20° C. Analysis of these DNA preparations, after HinDIII digestion, by agarose electrophoresis revealed three classes of plasmids; pHELP1 type plasmids, genomic library type plasmids and large complex type plasmids. From colonies containing the latter type of plasmids, a large scale plasmid isolation, using Nucleobond AX100 columns according to the manufacturers' instructions for the modified alkaline/SDS lysis (Macherey-Nagel) was performed on the frozen pellet of the 250 ml culture. This resulted in the isolation of two plasmid types. A and B, complementant A and B respectively. Both these plasmids were digested, using SalI, PstI, $EcoR_{19}$ HinDIII, and after agarose electrophoresis, the fragments were analysed in triplicate by Southern analysis using denatured radiolabelled pHELP1, plasmid A and plasmid B. This showed that both plasmids A and B, besides the pHELP part shared the same genomic region. Based upon the differences between the hybridisation signals found using the pHELP plasmid, showing the vector and AMA1 sequences, and the plasmid A and B signals, fragments hybridising with both plasmid A and B, but not with pHELP1, were identified and subcloned. A 4 kb EcoRI fragment and a 6.5 kb HinDIII fragment of plasmid B, and a 3 kb PstI fragment of plasmid A were found to hybridise with both plasmids A and B and were subcloned in pGEM7/EcoRI, pGE97/HinDIII and pBluescript/PstI, resulting in plasmid pNP1, 2 and 3 respectively. After propagation and purification these plasmids were used in complementation experiments using the mutant NW205::130 Ac 4-4 as described in Example 5.2. In these experiments the mutant was directly transformed without using pHELP1. In these experiments the plasmid pNP2, containing the 6.5 kb HinDIII fragment gave rise to complementation of the mutation. Further subcloning and transformation of pNP2-derived plasmids revealed a 5 kb BamHI-XbaI fragment, subcloned in pBluescript and resulting in plasmid pNP8, giving rise to complementation of strain NW205::130 Ac 4-4

Example 6.2

Subcloning of the A. niger xlnR Gene

For the subcloning of the xlnR gene, the A. niger genomic library, constructed as described by Harmsen et al., 1990, was screened for phages containing the xlnR region by using the 4 kb EcoRI fragment of pNP1 as probe. $3 \times 10^3$ pfu per plate were plated in NZYCM top-agarose containing 0.7% agarose on five 85-mm-diameter NZYCM (1.5% agar) plates as described (Maniatis et al., 1982) using E. coli LE392 as plating bacteria. After overnight incubation of the plates at 37° C. two replicas of each plate were made on HybondN* filters (Amersham) as described in Maniatis et al. (1982). After wetting the filters in 3×SSC the filters were washed for 60 min. at room temperature in 3×SSC, Hybridisation using the $^{32}$P-labelled 4 kb EcoRI fragment, prepared as described by Sambrook et al., 1989, was done according the following procedure (Sambrook et al., 1989); prehybridisation in 6×SSC (20×SSC per 1000 ml: 175.3 g NaCl. 107.1 g sodium citrate. $5.5H_2O$, pH 7.0). 0.1% SDS. 0.05% sodium pyrophosphate, 5* Denhardt's solution (100×Denhardts solution per 500 ml 10 g Ficoll-400, 10 g polyvinylpyrrolidone. 10 g Bovine Serum Albumin (Pentax Fraction V) and 20 μg/ml denatured herring sperm DNA at 68° C., for 3-5 hrs and hybridisation in an identical buffer which contained the denatured radiolabelled probe at 68° C. for 15-18 hrs. followed by two washes in 2×SSC, 0.1% SDS at 68° C. and two washes in 0.2×SSC, 0.1% SDS at 68° C. The membrane was covered with Saran wrap and autoradiographed overnight at −70° C. using Konica X-ray films and Kodak X-Omatic cassettes with regular intensifying screens.

This screening resulted in about 12 positive phages, of which eight were purified. Each positive plaque was picked from the plate using a Pasteur pipette and the phages were eluted from the agar plug in 1 ml of SM buffer containing 20 μl chloroform, as described in Maniatis et al. (1982). The phages obtained were purified by repeating the procedure described above using filter replicas from plates containing 50-100 plaques of the isolated phages.

After purification the phages were propagated by plating 5×10 phages on NZYCM medium. After overnight incubation at 37° C. confluent plates were obtained, from which the phages were eluted by adding 5 ml SM buffer and storing the plate for 2 h. at 4° C. with intermittent shaking. After collection of the supernatant using a pipette, the bacteria were removed from the solution by centrifugation at 4,000×g for 10 min. at 4° C. To the supernatant 0.3% chloroform was added and the number of pfu is determined. These phage stocks (A-R/H-R) contain approximately 109 pfu/ml.

DNA of five selected phages, A-R, B-R, C-R, E-R, F-R, isolated as described in Sambrook et al. (1989), was analysed by Southern analysis. The DNA was digested for 5 h. at 37° C. in a reaction mixture composed of the following solutions; 5 μl (≅1 μg) DNA solution; 2 μl of the appropriate 10× React buffer (Life Technologies); 10 U Restriction enzyme (Life Technologies) and sterile distilled water to give a final volume of 20 μl. The samples were incubated for 10 min. at 65° C. and rapidly cooled on ice, before loading on a 0.6% agarose gel in 1*TAE buffer. The DNA fragments were separated by electrophoresis at 25 V for 15-18 h.

After electrophoresis the DNA was transferred and denatured by alkaline vacuum blotting (VacuGene XL. Pharmacia LIB) to nylon membrane (Hybond N. Amersham) as described in the VacuGene XL instruction manual (pp. 25-26) and subsequently prehybridised and hybridised using the denatured radiolabelled 5 kb BamHI-XbaI fragment of plasmid pNP8 with hybridisation conditions as described. The hybridisation pattern was obtained by exposure of Kodak XAR-5 X-ray film for 18 h. at −70° C. using a regular intensifying screen. In all 5 clones, fragments originating from the same genomic region were found, for which a restriction pattern was constructed.

Based on the restriction map a 5 kb BamHI-XbaI fragment was selected for subcloning. 100 ng pbluescript BamHI-XbaI digested vector was mixed with 250 ng 5 kb BamHI-XbaI DNA of phage B-R and 4 μl 5* ligation buffer (composition; 500 mM Tris-HCl, pH 7.6; 100 mM $MgCl_2$; 10 mM ATP; 10 mM dithiotreitol; 25% PEG-6000), and 1 μl (1.2 U/μl) $T_4$ DNA ligase (Life Technologies) was added to this mixture in a final volume of 20 μl. After incubation for 16 h at 14° C. the mixture was diluted to 100 μl with sterile water. 10 μl of the diluted mixture was used to transform E. coli DH5α competent cells, prepared as described by Sambrook et al. (1989). Six of the resulting colonies were grown overnight in LB medium (LB medium per 1000 ml: 10 g trypticase peptone (BBL)$_9$ 5 g yeast extract (BBL), 10 g NaCl. 0.5 mM Tris-HCl pH 7.5) containing 100 μg/ml ampicillin. From the cultures plasmid DNA was isolated by the boiling lysis method as described by Maniatis et al. (1982), which was used in restriction analysis to select a clone harbouring the desired plasmid pIM230. Plasmid DNA was isolated on a large scale from 500 ml cultures EN coli DH5α containing pIM230 grown in LB medium containing 100 μg/ml ampicillin (Maniatis et al., 1982) The plasmid was purified by CsCl centrifugation, ethanol precipitated and dissolved in 400 μl TE. The yield was approximately 500 μg. E. coli containing pIR230 was deposited at the CBS under the conditions of the Treaty of Budapest on June 1996 under the accession number CBS 678.96

Example 6.3

Subcloning of the A. niger xlnR cDNA

To obtain a cDNA clone of part of the zinc finger regio of the xlnR gene, a reverse transcriptase and second strand synthesis reaction were carried out on 1 μg of polyA$^+$ RNA from an A. niger N402 wild-type strain grown on xylan for 30 hrs with an oligonucleotide starting at position 1476-1496 (Seq id no 9), in analogy to the method as described in the ZAP™-cDNA synthesis kit (Stratagene). An aliquot (1/50) of the second strand reaction was used as template in PCR with primer R026 and R025 (derived from positions 946-970 of Seq id no 9) in 35 cycles of 60 seconds of subsequent 95° C., 58° C. and 72° C. followed by an incubation of 5 minutes at 72° C. The resulting fragment of 500 bp was subcloned in the PGEM-T vector (Promega) and sequenced.

Example 7

The Primary Structure of the xlnR Gene

Example 7.1

Sequence Analysis of the xlnR Gene

The sequence of the A. niger xlnR gene, its promoter/regulation region, the structural part of the gene and the termination region, was determined by subcloning fragments from both pNP8 as pIM230, in combination with the use of specific oligonucleotides as primers in the sequencing reactions.

For nucleotide sequence analysis restriction fragments were isolated and were then cloned in pEMBL, pUC, pBluescript, pGEM DNA vectors, digested with the appropriate restriction enzymes. The nucleotide sequences were determined by the dideoxynucleotide chain-termination procedure (Sanger et al. 1977) using the Pharmacia ALF express automated sequencer and the Thermosequenase sequencing kit (Amersham). In the case of gene specific oligonucleotides the Pharmacia Cy5 internal labelling kit was used in combination with the T7 DNA polymerase sequencing kit (Pharmacia). The reactions and the electrophoresis was performed according to the manufacturers' instructions. Computer analysis was done using the PC/GENE programme (Intelligenetics). The sequence determined is given in SEQ ID NO:9.

Example 7.2

Description of the xlnR Gene

The sequence as given in SEQ ID NO:9, comprising the xlnR structural gene, is preceded by a 947 nucleotide long upstream region. In the upstream non-coding region CT-enriched sequences are found but no TATAA box. The structural part of the xlnR gene ranges from position 948 till position 3690, interrupted by two introns. The intron at position 1174 till 1237 was certified by sequencing the genomic fragment in pIM230, described in example 6.2 and part of the cDNA, as described in example 6.3. A second intron is indicated from position 3496 till position 3549. The second intron sequences follow the conserved intron sequences, normally found in fungi, for splice junctions and lariat sequence.

The xlnR gene encodes a protein of 875 amino acids in length. The derived polypeptide contains a typical N-terminal zinc binuclear cluster domain encoded by nucleotides from position 1110 till position 1260, with typical six cysteines coordinating the zinc. In this region furthermore a number of similarities with other fungal regulatory proteins are shown as listed in e.g. FIG. 1 of Kraulis et al. (1992) which is herein incorporated by reference.

A typical RRRLWW motif (SEQ ID NO: 12) is found from position 2623 till position 2649, this motif is found, with slight variations, in a number of binuclear zinc cluster regulatory proteins as noted by Suarez et al. (1995).

Example 7.3

Sequence Analysis of xlnR in *A. niger* Mutants

To determine whether the mutation, in the case of the *A. niger* mutants which do not express the xylanolytic system, as described in example 4.2, is located in xlnR, the sequence of the xlnR gene of these mutants was determined. For this a library enriched for 5.5 kb BamHI xlnR containing fragments was made for each of the NW205::130 Ac mutants. For the construction of this xlnR enriched library. 5.5 kb fragments of BamHI, HinDIII, XhoI, SstI and KpnI digested genomic DNAs were isolated for each strain. These fragments were mixed with BamHI digested, dephosphorylated pUC18 vector (Ready-To-Got pUC18 BamHI/BAP+Ligase. Pharmacia) and ligated. The ligation mixture was used to transform *E. coli* DH5α (MAX Efficiency DH5α™ Competent Cells, Gibco-BRL) for Amp resistance according to the manufacturers' protocol, which resulted in a primary library of $5*10^2$-$10^3$ colonies. These *A. niger* xlnR enriched libraries, after replating the primary library on master plates, were screened by colony filter hybridisation according to standard protocol (Sambrook et al. 1989), with the use of the denatured radiolabelled BamHI-XbaI insert of pIM230 as a probe.

For each mutant strain, positive colonies were picked from the master plate with a toothpick and were grown for 15-18 hrs at 37° C. in 5 ml LB medium containing 100 µg/ml Ampicillin, after which a miniprep plasmid DNA isolation was performed as described for boiling lysis by Sambrook et al. (1989). Analysis of these DNA preparations by agarose electrophoresis and comparing digestion patterns with xlnR specific patterns revealed colonies containing the correct 5.5 kb BamHI xlnR fragment.

The sequence of the *A. niger* mutants was determined with the use of specific xlnR oligonucleotides as primers in the sequencing reactions as described in example 7.2. For mutant NW205::130 Ac 1-15 a single basepair substitution was determined at position 3479, resulting in the change of the Leucine at position 823 of SEQ ID NO:9 into a Serine. For mutant NW205::130 Ac 2-5 a single basepair substitution was determined at position 3655, resulting in the change of the Tyrosine at position 864 of SEQ ID NO:9 into an Aspartic acid. These mutations identify both mutants as xlnR mutants.

Example 8

Expression of xlnR in *A. niger*

Example 8.1

Complementation of *A. niger* Mutants Non-Expressing the Xylanolytic System

For the complementation in all non-expressing mutants all ten NW205::130 Ac mutants, as described in Example 4, were transformed as described in example 2 of this document by combining protoplasts and pGW635 as a control for transformation frequency and pIM230 DNA for testing the complementation ability of pIR230.

The resulting transformant colonies were analysed for xylanolytic activity and compared with their parental mutant strain, by plating them on appropriate medium containing 1% oat spelts xylan as C source, and after 2-3 days a clearing of the xylan around the transformant colonies, but not the parental mutant strain, appeared for all ten, thereby showing the restoration of xylanolytic activity.

Example 9

Effect of xlnR Gene Dosage on the Expression of the *A. niger* Xylanolytic System To study the potential use of the xlnR gene for strain improvement for an increased xylanolytic expression, the strain N902::200-18, harbouring multiple copies (about 6) of the *A. niger* xlnD gene encoding β-xylosidase, was transformed to arginine prototrophy in a co-transformation experiment, as described in Example 2 of this document using 19 µg of the xlnR harbouring plasmid pIM230 and 2 µg of the plasmid pIM650 harbouring the *A. nidulans* argB gene (Johnstone et al. 1985). The transformants obtained were screened for increased endo-xylanase expression, on MM plates containing 1% Oat spelts xylan. Four colonies, having the fastest and largest halo formation, were selected to determine xlnR copy numbers. For this DNA of these transformants and the recipient strain, was isolated and serial dilutions were spotted onto Hybond N membrane. The copy number was estimated from the signals found after hybridisation, using a radiolabelled 4.5 kb SmaI/XbaI fragment spanning the coding sequence of the xlnR gene. Based on comparison to the recipient strain the xlnR copy number was determined to be 8 in N902::200-18-R14 and 32 in N902::200-18-R16. For both these transformants the effect of the increased gene dosage of xlnR was analysed by Northern analysis after strains were grown in liquid culture. This was done in a transfer experiment into 2% oat spelts xylan as a carbon source, after a preculture in 1% fructose for 18 h. Mycelial samples were taken 8 and 24 hrs after transfer, from which total RNA was isolated using TriZol (Life technologies) according to the manufacturers instructions and analysed by Northern blot analysis (Sambrook et al. 1989). Xylanase B expression levels were strongly increased in these transformants in comparison to the recipient strain, as detected after hybridisation using the radiolabelled 1 kb EcoRI/XhoI fragment of *A. niger* xlnB (Kinoshita et al., 1995).

To further study the potential use of the xlnR gene for strain improvement for an increased endo-xylanase expression. *A. niger* was transformed, as described in Example 2 of this document according to the following scheme; 1. pGW635 (pyrA) (positive control). 2. pDB-K(XA). 3 pDB-K(XA)+ pIR230) and 4 pGW6354 pIM230. The plasmid pDB-K(XA) contains both the *A. niger* pyrA gene and the *A. niger* xylanase A gene from *A. tubigensis* in the vector pEMBL18. Transformants were obtained for all conditions used, strains overexpressing endo-xylanases were selected by halo size in a plate screening on Oat spelts xylan (20 transformants from each group were tested).

From each group one transformant was selected and grown for activity assays. The strains were pregrown for 18 hrs on medium containing fructose, after which the mycelium (2.5 g wet weight in 50 ml) was transferred to medium containing 1.4% crude arabino xylan. All cultures were performed in shake flasks. Incubations were done for 40 hrs at 30° C. and the xylanase A levels were determined by HPLC analysis, while F-xylosidase and endo-xylanase activities were determined for both.

Figure 3:
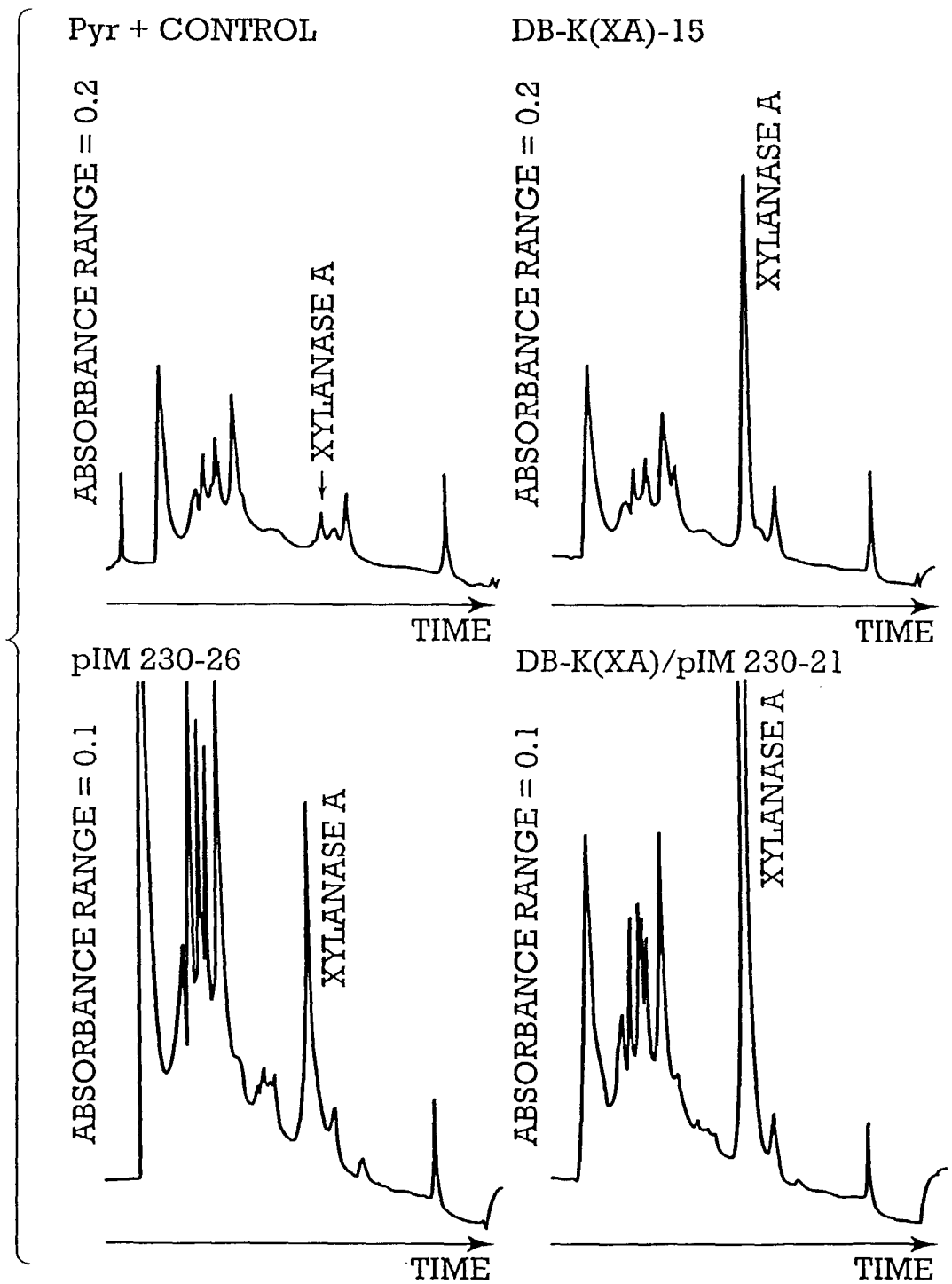
FIG. 3 depicts the results from experiments designed to increase endo-xylanase expression. *A. niger* strains transformed with pGX635 ("Pyr+control"), pDB-K(XA) ("DB-K(XA)-15"), pGW635+pIM230 ("pIM 230-26") and pDB-K(XA)+pIM230 ("DB-K(XA)/pIM 230-21"), and over-expressing endo-xylanase, were assayed for activity in the presence of 1.4% crude arabino xylan. The xylanase A activity is shown for each transformant.

Chromatography was carried out on standard Pharmacia-LKB HPLC equipment (Uppsala. Sweden) running a SOURCE 15 Q. HR 5/5-column at 1.5 ml/min. Buffer A=20 mM TRIS-buffer, pH 7.5 and buffer B 20 mM TRIS-buffer, pH 7.5 with 1M NaCl. Gradient from 0-50% buffer B over 30 min. Detection at 280 nm, Pharmacia-LKB UV-MII, absorbance range at 0.1-0.2, see FIG. 3. 100 µl culture media was diluted with 1000 µl 20 mM TRIS-buffer, pH 7.5 and 1000 µl diluted sample was applied to the column. The xylanase A activity is then seen as a peak eluting at approx. 30% B-buffer. From each group of transformants the one showing the highest xylanase A activity/peak in the HPLC analysis is shown in FIG. 3.

The endo-xylanase activity was determined by measuring the release of dyed fragments from azurine-dyed cross-linked wheat arabinoxylan (Xylazyme tablets) from Megazyme, Warriewood, Australia. The xylanase activity was calculated by comparing with an internal standard enzyme of 100 XU/gram (Xylanase-Unit) at 40° C. in 0.1M acetate buffer, pH 3.4. The same four transformants were assayed on water insoluble arabinoxylan at a pH were only xylanase A contributes to the endoxylanase activity, the results of this analysis is given in table 2.

TABLE 2

| Transformant | XU/gram |
| --- | --- |
| pyr+ (control) | 4 |
| DB-K (XA) -15 | 52 |
| DB-K (XA) /pIM230–21 | 111 |
| pIM23O-26 | 24 |

From the results shown in FIG. 3 and table 2 it is clear that transformation with the xylanase A encoding gene as expected gives a large increase in the xylanase A enzyme activity. More surprisingly, also after transformation using the activator gene xlnR, also a large increase in the level of xylanase A is found. This indicates a limitation in the level of activator XYL R (=xlnR gene product) in the untransformed parent. Therefore, it is expected that in a pDB-K(XA) multi-copy transformant the amount of transacting regulatory factor will be even more limiting. This is confirmed by the result for the pDB-K(XA)/pIM230 transformant, which has a xylanase A level twice as high as the pDB-K(XA) multicopy transformant.

Example 10

Screening Filamentous Fungi for the xlnR Gene

To analyse whether it is possible to isolate the xlnR counterpart from other fungi by heterologous hybridisation, using the 4.5 kb SmaI/XbaI fragment of the xlnR gene as a probe. DNA was isolated from the following strains; *A. niger* N902 (argB15, cspA1, fwnA1, metB10, pyrA5), *A. tubigensis* NW184 (cspA1, fwnA1, pyrA22), *A. nidulans* WG096 (pabaA1, yA2) of FGSC 187, *A. aculeatus* NW240 (pyrA3) of CBS 101.43, *A. aculeatus* NW217 (fwnA1, cspA1, pyrA4, lysA1) of CBS 115.80, *A. foetidus* (awamori) NW183 (cspA1, fwnA1, pyrA13, lysA1) of CBS 115.52, *A. japonicus* CBS 114.51 and *Trichoderma reesei* QM9414. 1-2 µg DNA was digested with BamHI or with XhoI and subsequently analysed by Southern analysis as described in Example 3. The hybridisation conditions used were: hybridisation in 6×SSC (20×SSC per 1000 ml:175.3 g NaCl, 107.1 g sodium citrate.5.5H$_2$O, pH 7.0), 0.1% SDS, 0.05% sodium pyrophosphate, 5* Denhardt's solution (100×Denhardt's solution per 500 ml:10 g Ficoll-400, 10 g polyvinylpyrrolidone, 10 g Bovine Serum Albumin (Pentax Fraction V) and 20 µg/ml denatured herring sperm DNA at 56° C. for 18-24 hrs followed by two 30 min. washes in 5×SSC, 0.1% SDS at 68° C. and two 30 min. washes in 2×SSC, 0.1% SDS at 56° C. After hybridisation the membrane was covered with Saran wrap and autoradiographed overnight at −70° C. using Konica X-ray films and Kodak X-Omatic cassettes with regular intensifying screens.

As a result hybridising fragments were found for all fungi analysed, very strong hybridisation signals were found in *A. niger, A. tubigensis, A. foetidus*, while in the other strains investigated clear hybridisation signals were found.

Example 11

Application of the Selection System Using Other Promoter Fragments

Plasmids were constructed containing promoter fragments from the *A. niger* abfA gene (Flipphi et al. 1994) and the *A. niger* abfB gene (Flipphi et al., 1993). For the construction containing the abfA promoter fragment, a 1.4 kb XhoI/PstI fragment from pIM900 (Flipphi et al. 1994) was ligated in SalI/PstI digested pAlter (Promega), as described in Example 1. Using the Altered Sites II in vitro mutagenesis system (Promega) a XhoI restriction site was created at positions −83 till −88 relative to the translation initiation site (Flipphi et al. 1994). From the resulting plasmid a 953 bp SstI/XhoI fragment was isolated. This fragment and a 1.5 kb XhoI fragment from pIM130 were ligated into pBluescript (Stratagene) digested with SstI/XhoI. Plasmids containing the correct orientation of the 1.5 XhoI fragment were identified by a digestion using BglII. The resulting plasmid is pAP8.

Analogously a 910 bp PstI fragment from the abAB promoter was isolated from pIM991 (Flipphi et al., 1993) and ligated in PstI digested pEMBL19. The resulting plasmid was digested using SalI and was ligated with the 1.5 kb XhoI fragment from plasmid pIM130. Plasmids obtaining both fragments in the correct orientation were identified by a digestion using BamHI. The resulting plasmid is pIM132.

A third plasmid containing a fragment from the *A. niger* pgaII was constructed by cloning a 1450 bp XbaI/XhoI fragment into the vector pAlter. Using the Altered Sites II in vitro mutagenesis system (Promega) a XhoI restriction site was created at positions −107 till −112 relative to the translation initiation site (Bussink et al. 1991). From the resulting plasmid a 1.2 kb XbaI/XhoI fragment was isolated. This fragment and a 1.5 kb XhoI fragment from pIM130 were ligated into pBluescript (Stratagene) digested with XbaI/XhoI. Plasmids containing the correct orientation of the 1.5 XhoI fragment were identified by a digestion using HinDIII. The resulting plasmid is pIIP7. From the same pgaII gene a 223 bp HinDIII/PstI fragment (Bussink et al., 1992) was isolated and ligated in HinDIII/PstI digested pEMBL19. The resulting plasmid was digested using SalII and was ligated with the 1.5 kb XhoI fragment from plasmid pIM130. Plasmids containing both fragments in the correct orientation were identified by a digestion using HinDIII. The resulting plasmid is PHPII.

All four plasmids were introduced in *A. niger* NW219 by transformation as described in Example 2, using 10 mM L-arabitol as an inducer in transfomation experiments using the constructs having the abf promoter fragments (plasmids AP8 and pIM132) and 1% polygalacturonic acid (USB chemicals) in the case of the plasmids harbouring the pgaII fragments. While for the plasmids AP8 and pIM132 transformants were found at high frequency, for the transformation experiment using the pgaII promoter fragment containing plasmids pIIP7 and pHPII only 5 and 7 transformants were found respectively.

The transformants resulting from the transformation experiment using the plasmids pAP8 and pIM132 (abf promoter fragments were analysed phenotypically as described in Example 3 using MM containing 10 mM L-arabitol/50 mM sorbitol, 10 mM L-arabitol/50 mM D-glucose and 50 mM D-glucose. The expected phenotype; growth on 10 mM L-arabitol/50 mM sorbitol, non-growth on 10 mM L-arabitol/50 mM D-glucose and 50 mM D-glucose, was found for 10 out of 29 transformants resulting from plasmid pAP8 and 13 out of 30 transformants resulting from plasmid pIM132. The transformants resulting the plasmids pIIP7 and PHPII were tested on MM containing 1% polygalacturonic acid, 1% polygalacturonic acid/50 mM D-glucose and 50 mM D-glucose. Both classes of transformants however, did not show the expected phenotype, all transformants were able to grow on all three media. This suggests that these transformants result from a double cross-over at the pyrA locus.

Based on the results for the pgaII promoter fragment containing plasmids, we have tested whether we could improve transformation frequency by improving induction. We assumed that transformation more or less failed due to lack of inducer, since no monomeric inducer for polygalacturonases was available and thus the polymer needs to be degraded to release inducer to give expression. We tested whether supplementation of the medium using a small amount of uridin could overcome this problem. For this the NW219 and a transformant NW219::pIM132#30 were tested on media containing 1% Oat spelts xylan, giving induction of abfB, in combination with an increasing amount of uridin; respectively 0, 0.001, 0.005, 0.01, 0.1, 1, 5 and 10 mM. In this experiment the recipient strain NW219 did not grow on media containing less then 0.01 mM uridin, while the NW219::pIM132#30 transformant strain grew under all conditions used. However, the degree of sporulation and colony morphology varied, the lowest uridin concentration giving wild-type-like sporulation being around 0.01 mM uridin.

Based on these results *A. niger* NW219 transformation using the plasmids pIIP7 and pHPII was repeated using MMS as described in Example 2 containing 1% lemon pectin (degree of esterification 45%)(Copenhagen Pectin factory) and two conditions for uridin supplementation 0.01 mM and 0.005 mM respectively. This resulted in an increased number of transformants found. These transformants were tested on media containing 1% lemon pectin as described above. 1% lemon pectin/50 mM D-glucose and 50 mM D-glucose, for which the expected phenotype is respectively growth, non-growth and non-growth. For the pIIP7 resulting transformants 10 out of 30 transformants and for the pHPII 9 out 30 transformants the expected phenotype was found.

A selection of the transformants showing the expected phenotype were analysed by Southern analysis. DNA was isolated and analysed as described in Example 3. For the transformants resulting from the abfA promoter fragment containing plasmid pAP8 the DNA was digested using ClaI, for pIM132 (abfb) resulting transformants using ClaI and for the transformants resulting from pgaII plasmids pIIP7 and pHPII using ClaI. Based on the autoradiograph obtained after hybridisation using the following radiolabelled fragments; the 3.8 kb XbaI and the 1:2 kb CloA fragment of the pyrA gene, transformants were selected based on estimated copy number. The following transformants were selected; AP8/16 (abfA), NW219::132#8 (2 copies) and NW219::132#30 (3-4 copies)(abfB). NW219::pIIP7#3 (2 copies) and NW219::pHPIIP#9 (2 copies)(pgaII)

The selected transformants were subjected to mutagenesis as described in Example 4. Arabinofuranosidase derepressed mutants were selected on MM+50 mM D-glucose and on MM+10 mM L-arabitol/50 mM D-glucose, while polygalacturonase derepressed mutants were selected on MM+50 mM D-glucose and on MM+1% lemon pectin/50 mM D-glucose. After 4-7 days 5-10 mutant colonies per plate were found, which on basis of their morphology could be divided into three classes; large, well sporulating colonies, intermediate sized, well sporulating colonies and small poorly sporulating colonies. A random selection of 20 of these mutants was made and the selected mutants were tested on media containing different carbon sources or substrates. The arabinofuranosidase mutant colonies were found to be able to grow on media containing D-glucose, D-glucose/L-arabitol and L-arabitol, while the parental strains only were able to grow on medium containing L-arabitol as a carbon source. Analogously the polygalacturonase mutants also were able to grow on MM+50 mM D-glucose and on MM 41% lemon pectin/50 mM D-glucose and MM+1% lemon pectin. The parental strains could only grow on MM+1% lemon pectin. In addition the arabinofuranosidase mutants (20 of each) were tested on the chromogenic substrate methylumbelliferyl-α-L-arabinofuranoside as described in Example 4. While the parental strains did not show any arabinofuranosidase expression of D-glucose/L-arabitol containing media, as detected by fluorescence of the substrate, the mutants showed variable levels of expression, the highest levels were found in mutants selected on the D-glucose medium.

The polygalacturonase mutants were tested on MM+0.1% lemon pectin/50 mM glucose, two and three days after inoculation of the plates polygalacturonase activity was visualized by staining as described by Ried and Collmer (1985). In this case for the parental strain a small halo was found, while in the mutants various degrees on increased halo formation was detected.

According to Example 4 also non-expressing mutants were selected on media containing FOA. For this strains NW219::132#30(abfB) were mutated and plated on MM+10 mM L-arabitol+1 mg/ml FOA+10 mM uridin. After 7-10 days mutants were selected and plated to MM containing 10 mM L-arabitol/50 mM sorbitol, 10 mM uridin and having a top agar containing 0.5% AZCL-arabinan (Megazyme, Sydney, Australia) for the detection of endo-arabinan expression. Two of the 30 transfodrants tested, 132/30 F12 and F26, were not able to release the dye from the substrate, an indication for the absence of endo-arabinan activity. Upon cultivation of these transformants in liquid MM containing 10 mM L-arabitol and 10 mM uridin and subsequent measurement of arabinofuranosidase activity in the culture filtrates, an at least 4-fold decrease in activity was found.

The strain NW219::pIIP7#3 was mutated and plated on MM containing 1% lemon pectin/50 mM sorbitol. 10 mM uridin and 1 mg/ml FOA. After incubation of the plates for 6-10 days mutants were picked and screened for polygalacturonase activity as described above. Of 65 mutants selected three mutants were found to have a decreased haloformation after polygalacturonase activity staining, indicating a decrease in polygalacturonase expression.

Examples 7, 8 and 11 of EP 95201707.7, which is a copending European patent application of which a copy has been included upon filing the subject document and which examples have also been copied into this document.

Example 7 of EP 95201707.7: Transformation of *A. niger* Using the Plasmid pIM200

250 ml of culture medium, which consists of MM supplemented with 2% glucose, 0.5% Yeast Extract, 0.2% Casamino acids (Vitamin free), 2 mM leucine, 10 µM nicotinamide, 10 mM uridine, was inoculated with $1*10^6$ spores per ml of strain NW155 (CspA1, argB13, pyrA6, nicA1, LeuA1, prtF28) (derived from NW228, Van den Hombergh et al, 1995) and mycelium was grown for 16-18 hours at 30° C. and 250 rpm in a orbital New Brunswick shaker. The mycelium was harvested on Myracloth (nylon gauze) using a Bachner funnel and mild suction and was washed several times with SP6 (SP6: 0.8% NaCl, 10 mM Na-phosphate buffer pH 6.0). 150 mg Novozyme 234 was dissolved in 20 ml SMC (SMC: 1.33 M sorbitol, 50 mM CaCl$_2$, 20 mM MES buffer, pH 5.8) to which 1 g (wet weight) mycelium was added and which was carefully resuspended. This suspension was incubated gently shaking for 1-2 hours at 30° C., every 30 minutes the mycelium was carefully resuspended and a sample was taken to monitor protoplast formation using a haemocytometer to count the protoplasts. When sufficient protoplasts were present (more then $1*10^8$) these were carefully resuspended and the mycelial debris was removed by filtration over a sterile glasswool plug. The protoplasts were collected by 10 minutes centrifugation at 3000 rpm and 4° C. in a bench centrifuge, the supernatant was removed and the pellet was carefully resuspended in 5 ml STC (STC: 1.33 M Sorbitol, 50 mM CaCl$_{24}$ 10 mM Tris/HCl, pH 7.5). This wash step was repeated twice and the protoplasts were finally resuspended in STC at a density of $1*10^8$ per ml.

The transformation was performed by adding 20 µg of pIM200 DNA and 5 µg pGW635, containing the *A. niger* pyrA gene (dissolved in a 10-20 µl TE), to 200 µl of protoplast suspension together with 50 PI of PEG buffer (PFG Buffer: 25% PEG-6000, 50 mm CaCl$_2$, 10 mM Tris/HCl pH 7.2), mixed gently by pipetting up and down a few times, and incubated at room temperature for 20 minutes. After this period 2 ml PEG buffer was added, the solution was mixed gently and incubated at room temperature for another 5 minutes and subsequently 4 ml of STC was added and mixed gently on a vortex mixer. One ml portions of this suspension were then added to 4 ml of 0.95 M sucrose osmotically stabilised top agar and poured on osmotically stabilised plates. As a control *A. niger* was also transformed using pGW635.

Example 8 of EP 95201707.7

Analysis of Transformants

The transformants from pIM200 obtained in Example 7 were analysed phenotypically by plating on MM containing 1% Oat spelt xylan and 1 mM 4-methylumbelliferyl-β-D-xyloside. Of the 26 transformants tested, five had an increased fluorescence. These transformants, together with a PYR$^+$ transformant as a reference, were grown on MM containing 1% Oat spelt xylan for 20, 27 and 42 hrs, after which the β-xylosidase activity towards PNP-X was measured. The results are summarised in Table C.

An increased level of β-xylosidase activity was found in all five transformants selected, the highest level being more then 30 times the wild-type activity. These results were confirmed by Western blot analysis, using the anti β-xylosidase antibody, prepared as described in Example 3 of the EP 95201707.7, and the Bio-Rad Immun-blot GAR-AP assay kit following the suppliers instructions.

TABLE C

| | β-xylosidase activities in *A. niger* transformants activity (mU/ml culture filtrate) after: | | |
|---|---|---|---|
| | 20 hr | 27 hr | 42 hr |
| pGW 635 | 15 | 16 | 17 |
| XlsA1 | 82 | 86 | 51 |
| XlsA4 | 90 | 112 | 78 |
| XlsA8 | 211 | 239 | 384 |
| XlsA9 | 63 | 110 | 74 |
| XlsA12 | 96 | 295 | 527 |

Example 11 of EP 95201707.7

Disruption of the *A. niger* xlnD Gene

Example 11.1

Construction of the Disruption Plasmids pIM203 and pIM204

The gene disruption plasmids pIM203 and pIM204 were constructed by generating an internal fragment of the xlnD gene by PCR. The fragment was generated using the oligonucleotides derived from the xlnD sequence (SEA ID NO: 8). Xylos001 was derived from positions 1157 till 1176 and xylos004 was derived from positions 3147 till 3164. The fragment was generated by PCR containing 10 µl 10*reaction buffer (100 mM Tris-HCl, pH 8.3, 500 mM KCl. 15 mM MgCl$_2$, 0.01% gelatine). 16 µl 1.25 mm of each of the four deoxynucleotide triphosphates, 1 ng of the plasmid pIM200 DNA and 1 µg of each of the oligonucleotides in a final volume of 100 µl. This reaction mixture was mixed and 1 µl TAQ polymerase (5 U/µl) (Life Technologies) was added. The DNA was denatured by incubation for 3 min at 92° C. followed by 25 cycli of 1 min 92° C. 1.5 min 52° C. and 1.5 min 72° C. After these 25 cycli the mixture was incubated for 5 min at 72° C. Analysis of the reaction products by agarose electrophoresis revealed a fragment of about 2000 bp. which corresponds to the size expected, based on the sequence of the gene. The resulting fragment was subcloned in the vector pGEM-T (Promega) resulting in the plasmid pIM202. Plasmid pIM203 was constructed by ligation of a SmaI/PstI fragment of pILJ16 (Johnstone et al., 1985), containing the *A. nidulans* argB gene (Upshall et al., 1986), in the EcoRV/Pst1 digested pIM202 vector. Plasmid pIM204 was constructed by ligation of the NsfI/XbaI fragment of pIM130 (this document. EP 95202346.3), containing the pyrA gene under the control of the UAS of the xlnA promoter of *A. tubigensis*, in the SpeI/NsiI digested pIM202 vector.

Example 11.2

Disruption of the xlnD Gene in *A. niger*

The plasmids containing the xlnD internal fragment as well as the argB gene (pIM203) or the pyrA gene (pIM204), as described in Example 11.1 of the copending EP application, as a selection marker in transformation, were used to disrupt the *A. niger* xlnD gene. For this *A. niger* N902 (argB15, cspA1, fwnA1, metB10, pyrA5) was transformed, as described in Example 2 of this document, using the plasmids pIM203 and pIM204 selecting for arginine or uridine prototrophy respectively. The resulting transformants were screened for activity on methylumbelliferyl-β-D-xyloside on a 1% xylan plate as described in Example 8 of the copending EP application. For both groups of transformants twenty were screened. Of these transformants one of each group had a severe decreased level of MUX activity after 24 h of growth. Southern analysis of the selected transformants, as described in Example 3 of the copending application, demonstrated for the pIM203 transformant a multicopy integration at the homologous xlnD locus. In case of the pIM204 transformant a single homologous integration at the xlnD locus had occurred. Analysis for PNP-X activity, as described in Example 8 of the copending EP application, of these transformants revealed an at least 100-fold decrease in D-xylosidase activity.

Example 11.3

Effect of Overexpression and Inactivation of xlnD Gene on the Expression of Xylanolytic System of *A. niger*

To determine the effect of xlnD expression on the expression of the xylanolytic spectrum. *A. niger* N902 two xlnD multicopy transformants in N902 and the xlnD gene disruption strains were grown in liquid culture. This was done in a transfer experiment into 2% oat spelts xylan or 3% D-xylose as a carbon source, after a preculture in 1% fructose for 18 h. Beta-xylosidase activity was determined as PNP-X activity in the culture filtrate. With both C sources a clear overexpression could be seen for the pIM200 transformants against an almost absence of PNP-X activity for both (pIM203 and pIM204) inactivation transformants. The xlnD gene disruption transformants showed an initial decreased level of endo-xylanase expression, which however increased in time finally after 16 hrs resulting in increased activity levels in comparison to the *A. niger* wild-type. Thus resulting in xylanase preparations free of β-xylosidase.

The culture filtrates were subsequently analysed by HPLC analysis, using a Dionex system and Pulsed Amperometric Detection. For this 1 ml of culture filtrate was boiled immediately after harvesting, to inactivate the xylanolytic enzymes, after which the sample was centrifuged for 10 min. (14.000 rpm at 4° C. Eppendorf centrifuge). The resulting supernatant was diluted 5-fold in bidest and 20 µl was analysed by HPLC using a Dionex CarboPac 100 column. The analysis indicated that, while in the wild-type and in the over-expression transformants only in the initial stage xylose oligomers could be detected in the culture filtrate, in the disruption mutant xylobiose and to a lesser extent xylotriose accumulated in the culture filtrate, thus resulting in a source for xylooligomers, in particular xylobiose and xylotriose.

REFERENCES

Andrianopoulos, A. and Hynes. M. J. (1988). Mol. Cell. Biol. 8:3532-3541.
Aviv, H. and Leder, P. (1972) *Proc. Natl. Acad. Sci. USA* 11: 1408-1412. Balance D. J. and Turner G. C. (1985) *Gene* 36: 321-331.
Bailey, A. M., et al. (1991) Nucl. Acids Res. 19: 5273-4278.
Bailey, A. M., Biely, P. and Poutanen, K. (1992) J. Biotechnol. 23: 257-270.
Berka, R. M., Ward. M., Wilson, L. J., Hayenga, K. J., Kodama, K. H., Carlomagno, L. P. and Thompson, S. A. (1990). Gene: 86: 153-162.
Bussink, H. J. D., van den Hombergh. J. P. T. W., van den IJssel, P. R. L. A. and Visser J. (1992). Appl. Microbiol. and Biotechnol.: 37, 324-329.
Davies. R. W. (1991). Molecular biology of a high-level recombinant protein production system in *Aspergillus*. In Leong, S. A. and Berka, R. M. (Eds), Molecular industrial Mycology: systems and applications for filamentous fungi, Marcel Dekker, Inc., pp 45-82.
Ekwall, K. and Ruusla. T. (1991). Nucl. Acids Res. 19: 1150.
Felenbok, B. and Sealy-Lewis H. M. 91994). In: *Aspergillus*: 50 years on. Martinelli. S. D. and Kinghorn. J. R. (Eds): 141-179).
Flipphi. M. J. A., van den Heuvel, M., van der Veen, P., Visser, J., and de Graaff. L. H. (1993) *Curr. Genet.* 24:525-532.
Flipphi, M. J. A., Visser. J., van der Veen, P. and de Graaff. L. H. (1994) *Microbiology* 140:2673-2682.
Fowler, T., et al. (1990). Curr. Genet. 18:537-545.
Gems, D. H. and Clutterbuck A. J. (1993) Curr. Genet. 24: 520-524.
Goosen T. Bloemheuvel G. Gysler C, Bie DA de, Broek HWJ van den, Swart K (1987) Curr Genet 11:499-503
Graaff L H de (1988) The structure and expression of the pyruvate kinase gene of *Aspergillus nidulans* and *Aspergillus niger*. PhD Thesis Landbouw Universiteit, Wageningen, The Netherlands
Graaff L. H. de, van den Broeck, H. C. van Ooijen A. J. J. and Visser. J. (1994). Mol Microbiol. 12: 479-490.
Gwynne, D. I., Buxton. F. P., Gleeson, M. A. and Davies R. W. (1987) Genetically engineered secretion of foreign proteins from Aspergillus species. In: Burgess, R. (eds.), Protein purification: *Micro to macro*, Alan R. Liss, N Y., pp 355-365.
Harmsen, J. A. M., Kusters-van Someren, M. A., Visser. J. (1990) *Curr. Genet.* 18: 161-166.
c.f. Hinnen. A. et al., (1995). In: Gene expression in recombinant microorganisms. Smith, A. (ED) Marcel Dekker Inc. New York: 121-193).
c.f. Hinnen, A., et al., (1995). In: Gene expression in recombinant microorganisms. Smith, A. (ED) Marcel Dekker Inc. New York: 121-193).
c.f. Hinnen. A., et al. (1995). In: Gene expression in recombinant microorganisms. Smith, A. (ED) Marcel Dekker Inc. New-York: 121-193).
Hombergh van den, J. P. T. W., van de Vondervoort, P. J. I. van der Heijden. N. C. B. A., and Visser. J. (1995) *Curr. Genet.* 28:299-308.
Johnstone, I. L., Hughes. J. and Clutterbuck, A. J. (1985) *EMBO J.* 4: 1307-1331.
Katz, M. E. and Hynes, M. J. (1989). Mol. Cell. Biol. 9:5696-5701.
Kelly J. M. and Hynes M. J. (1985). EMBO J. 4:475-479
Kelly, J. M. and Hynes, M. J. (1987). Curr. Genet. 12:21-31.
Kinoshita K., Takano. M., Koseki. T. Ito, and Iwano, K. (1995). J. of Ferment. and Bioeng.:79. no 5, 422-428.
Kraulis, P. J., Raine, A. R. Gadhavi, P. L. and Laue E. D. (1992) Nature 356: 448-455.
Maniatis, T. Fritsch, E. F. and Sambrook. J., (1982). Molecular Cloning: A Laboratory Manual. Cold Spring Habor, N.Y.: Cold Spring Labor Laboratory Press.
Sambrook, J., Fritsch, E. F. and Maniatis T. (1989). Molecular Cloning: A Laboratory Manual. 2nd edn. Cold Spring Habor, N.Y.: Cold Spring Habor Laboratory Press.
Sanger, F., Nickelsen, S. and Coulson A. R. (1977) *Proc. Natl. Acad. Sci. USA* 74: 5463-5467.
Schutte, J. B. (1991), Nutritional value and physiological effects of D-xylose and L-arabinose in poultry and pigs. *Datapress & Datavisions*, Wageningen, 173 pp.

Suárez, T. Vieira de Queiroz, M., Oestreicher, N. and Scazzocchio, C. (1995). EMBO J. 14, no 7:1453-1467.
a) Unkles, S. E. et al. (1989). Gene 78: 157-166 and
b) Unkles. S. E., et al. (1989). Mol. Gen. Genet. 218:99-104.

Verdoes, J. C., Punt, P. J., Schrinckx, J. M., van Verseveld, H. W. Stouthamer A. H. and van den Hondel, C. A. M. J. J. (1993). Transgeneic res.: 2, 84-92.

Verdoes. J. C., Punt. P. J. and van den Hondel C. A. M. J. J. (1995) Appl. Microbiol. Biotechnol. 43: 195-205

Verdoes. J. C. (1994) Molecular genetic studies of the overproduction of glucoamylase in *Aspergillus niger*. Thesis Vrije Universiteit Amsterdam, The Netherlands.

Vishniac, W. and Santer, M. (1957) *Bacteriol. Rev.* 21: 195-213.

Wilson, L. J., Carmona. C. L. and Ward, M. (1988). *Nucl. Acids Res.* 16:

Whittington. H. Kerry-Williams, S., Bidgood, K., Dodsworth. K., Peberdy. J., Dobson, M. Hinchcliffe, E., and Ballance. D. J. (1990). Curr. Genet. 18: 531-536.

---

The invention claimed is:

1. An isolated nucleic acid molecule comprising nucleotides 1 to 4173 of SEQ ID NO:9.

2. An isolated nucleic acid molecule encoding amino acid residues 1 to 875 of SEQ ID NO: 11.

3. An isolated nucleic acid molecule having at least 96% identity to nucleotides 1 to 4173 of SEQ ID NO:9, wherein said nucleic acid molecule encodes a xylanolytic regulator comprising a zinc finger binding domain, wherein said xylanolytic regulator is capable of binding to one or more of target genes selected from the group consisting of xlnA, xlnB, xlnC, xlnD and axeA.

4. The isolated nucleic acid molecule of claim 3, wherein said nucleic acid molecule has at least 97% identity to nucleotides 1 to 4173 of SEQ ID NO:9, wherein said nucleic acid molecule encodes a xylanolytic regulator comprising a zinc finger binding domain, wherein said xylanolytic regulator is capable of binding to one or more of target genes selected from the group consisting of xlnA, xlnB, xlnC, xlnD and axeA.

5. The isolated nucleic acid molecule of claim 3, wherein said nucleic acid molecule has at least 98% identity to nucleotides 1 to 4173 of SEQ ID NO:9, wherein said nucleic acid molecule encodes a xylanolytic regulator comprising a zinc finger binding domain, wherein said xylanolytic regulator is capable of binding to one or more of target genes selected from the group consisting of xlnA, xlnB, xlnC, xlnD and axeA.

6. The isolated nucleic acid molecule of claim 3, wherein said nucleic acid molecule has at least 99% identity to nucleotides 1 to 4173 of SEQ ID NO:9, wherein said nucleic acid molecule encodes a xylanolytic regulator comprising a zinc finger binding domain, wherein said xylanolytic regulator is capable of binding to one or more of target genes selected from the group consisting of xlnA, xlnB, xlnC, xlnD and axeA.

7. An isolated nucleic acid molecule having at least 96% identity with a nucleic acid molecule encoding amino acid residues 1 to 875 of SEQ ID NO: 11, wherein said isolated nucleic acid molecule encodes a xylanolytic regulator comprising a zinc finger binding domain, wherein said xylanolytic regulator is capable of binding to one or more of target genes selected from the group consisting of xlnA, xlnB, xlnC, xlnD and axeA.

8. The isolated nucleic acid molecule of claim 7, wherein said isolated nucleic acid molecule has at least 97% identity to a nucleic acid molecule encoding amino acid residues 1 to 875 of SEQ ID NO: 11, wherein said nucleic acid molecule encodes a xylanolytic regulator comprising a zinc finger binding domain, wherein said xylanolytic regulator is capable of binding to one or more of target genes selected from the group consisting of xlnA, xlnB, xlnC, xlnD and axeA.

9. The isolated nucleic acid molecule of claim 7, wherein said isolated nucleic acid molecule has at least 98% identity to a nucleic acid molecule encoding amino acid residues 1 to 875 of SEQ ID NO: 11, wherein said nucleic acid molecule encodes a xylanolytic regulator comprising a zinc finger binding domain, wherein said xylanolytic regulator is capable of binding to one or more of target genes selected from the group consisting of xlnA, xlnB, xlnC, xlnD and axeA.

10. The isolated nucleic acid molecule of claim 7, wherein said isolated nucleic acid molecule has at least 99% identity to a nucleic acid molecule encoding amino acid residues 1 to 875 of SEQ ID NO: 11, wherein said nucleic acid molecule encodes a xylanolytic regulator comprising a zinc finger binding domain, wherein said xylanolytic regulator is capable of binding to one or more of target genes selected from the group consisting of xlnA, xlnB, xlnC, xlnD and axeA.

11. A kit for detecting and/or isolating nucleic acid sequences wherein said kit comprises two or more nucleic acid molecules identical to a portion of SEQ ID NO: 9, wherein in each of the two or more nucleic acid molecules the portion identical to SEQ ID NO: 9 is at least 60 nucleotides in length, and wherein each of the two or more nucleic acid molecules do not encode a zinc finger binding domain.

* * * * *

SEQUENCE LISTING

```
<160> NUMBER OF SEQ ID NOS: 16

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cacaatgcat cccctttatc cgcctgccgt                                          30

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
caattgcgac ttggaggaca tgatgggcag atgaggg                                  37

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agagaggata tcgatgtggg                                                     20

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ccctcatctg cccatcatgt cctccaagtc gcaattg                                  37

<210> SEQ ID NO 5
<211> LENGTH: 2054
<212> TYPE: DNA
<213> ORGANISM: Aspergillus tubingensis
<220> FEATURE:
<221> NAME/KEY: CDS
<222> LOCATION: (950)..(1179)
<220> FEATURE:
<221> NAME/KEY: sig_peptide
<222> LOCATION: (950)..(1031)
```

<220> FEATURE:
<221> NAME/KEY: mat_peptide
<222> LOCATION: (1031)..(1631)
<220> FEATURE:
<221> NAME/KEY: CDS
<222> LOCATION: (1229)..(1631)

<400> SEQUENCE: 5

```
aacgtctgca gtcccgtact gtttaccaaa atgccaggcc actggtggat atacaacttt      60
gtaatacgtt gccggagtca gccccctactc cctgatgggt tcccactccc tagttacttc    120
ctactgggta gtaggctcct agagtggggt aaagtttgcc aagggtttag ccccagtctt    180
gtttatgctt ggctaggcag gacctgggta agttgatggc tcctgcattc ctacctgagt    240
atttccagct ataagcgaga tttgccatac tcttcagcga gtccggatgg tccgcgccga    300 ggttgacccct gccttcatca cctacacaaa gaactcctcg gccaactccc ggtggccttc    360
gagctccaaa gtaccttcgc gacctttggc cagtgtttct cgcagcgttt actgagccta    420
aggcttgcta caataaataa agagacataa ccttgcagta catacgtctt gtatgagcga    480
ggaactgtgt tcagtagtag atcagtgggt acataatcat gaacatgact tctgagccag    540
aaaaccttct gcagggaacc ggtgaagaaa ccccacttcc ccgcctccac taactgcagc    600 cccctttatcc gcctgccgtc catttagcca aatgtagtcc atttagccaa gtgcggtcca    660
tttagccaag tccagtgctt aggttggtgg ctacacagga acggccatg aatgtagaca     720 caactataga actgtcccta gaaataggct cgaggttgtt agagcgttta aggtgatgcg     780
gcaaaatgca tatgactgag ttgcttcaac gtgcagggga aagggataaa tagtctttt     840 cgcagaatat aaatagaggt agagcgggct cgcagcaata ttgaccagga cagggcttct     900
```

```
tttccagttg catacatcca ttcacagcat tcagctttct tcaatcatc atg aag gtc     958
                                                        Met Lys Val
                                                               -25
```

```
act gcg gct ttt gca ggt ctt ttg gtc acg gca ttc gcc gct cct gcc      1006
Thr Ala Ala Phe Ala Gly Leu Leu Val Thr Ala Phe Ala Ala Pro Ala
        -20                 -15                 -10
```

```
cca gaa cct gat ctg gtg tcg cga agt gcc ggt atc aac tac gtg caa      1054
Pro Glu Pro Asp Leu Val Ser Arg Ser Ala Gly Ile Asn Tyr Val Gln
    -5                   -1   1                    5
```

```
aac tac aac ggc aac ctt ggt gat ttc acc tac gac gag agt gcc gga      1102
Asn Tyr Asn Gly Asn Leu Gly Asp Phe Thr Tyr Asp Glu Ser Ala Gly
         10                  15                  20
```

```
aca ttt tcc atg tac tgg gaa gat gga gtg agc tcc gac ttt gtc gtt      1150
Thr Phe Ser Met Tyr Trp Glu Asp Gly Val Ser Ser Asp Phe Val Val
25                   30                  35                  40
```

```
ggt ctg ggc tgg acc act ggt tct tct aa gtgagtgact gtattcttta         1199
Gly Leu Gly Trp Thr Thr Gly Ser Ser Asn
                45                  50
```

```
accaaggtct aggatctaac gtctttcag c gct atc acc tac tct gcc gaa tac   1253
                                  Ala Ile Thr Tyr Ser Ala Glu Tyr
                                                           55
```

```
agc gct tct ggc tcc gct tcc tac ctc gct gtg tac ggc tgg gtc aac      1301
Ser Ala Ser Gly Ser Ala Ser Tyr Leu Ala Val Tyr Gly Trp Val Asn
     60                  65                  70
```

```
tat cct caa gct gag tac tac atc gtc gag gat tac ggt gat tat aac      1349
Tyr Pro Gln Ala Glu Tyr Tyr Ile Val Glu Asp Tyr Gly Asp Tyr Asn
75                   80                  85                  90
```

```
cct tgc agt tcg gcc aca agc ctt ggt acc gtg tac tct gat gga agc      1397
Pro Cys Ser Ser Ala Thr Ser Leu Gly Thr Val Tyr Ser Asp Gly Ser
                 95                 100                 105
```

```
acc tac caa gtc tgc acc gac act cga aca aac gaa ccg tcc atc acg      1445
```

```
                Thr Tyr Gln Val Cys Thr Asp Thr Arg Thr Asn Glu Pro Ser Ile Thr
                            110                 115                 120 gga aca agc acg ttc acg cag tac ttc tcc gtt cga gag agc acg cgc              1493
Gly Thr Ser Thr Phe Thr Gln Tyr Phe Ser Val Arg Glu Ser Thr Arg
            125                 130                 135 aca tct gga acg gtg act gtt gcc aac cat ttc aac ttc tgg gcg cac              1541
Thr Ser Gly Thr Val Thr Val Ala Asn His Phe Asn Phe Trp Ala His
        140                 145                 150 cat ggg ttc ggc aat agc gac ttc aat tat cag gtc gtg gcg gtg gaa              1589
His Gly Phe Gly Asn Ser Asp Phe Asn Tyr Gln Val Val Ala Val Glu
155                 160                 165                 170 gca tgg agc ggt gct ggc agc gct agt gtc aca atc tct tct                      1631
Ala Trp Ser Gly Ala Gly Ser Ala Ser Val Thr Ile Ser Ser
                175                 180 tgagagatta gtgccctagt agtcggaaga tatcaacgcg gcagtttgct ctcaggtggt            1691
gtgatgatcg gatccggtct ctggggttac attgaggctg tataagttgt tgtggggccg            1751
agctgtcagc ggctgcgttt tcagcttgca cagataatca actctcgttt tctatctctt            1811
gcgtttcctc gctgcttatc ctatccatag ataattattt tgcccactac cacaacttgt            1871
tcggtcgcag tagtcactcc gagcaaggca ttgggaaatg ggggatgcgg ggtgctgcgt            1931
accctctaac ctagggcatt ttaaaggata tttaccctcc agatattcta tagatacaga            1991
cttcttagga ctgcgggtaa tatagagagc gaaatttcta cagttcgatg cagttcaatg            2051
cga                                                                         2054

<210> SEQ ID NO 6
<211> LENGTH: 3026
<212> TYPE: DNA
<213> ORGANISM: Aspergillus niger
<220> FEATURE:
<221> NAME/KEY: CDS
<222> LOCATION: (724)..(2538)
<220> FEATURE:
<221> NAME/KEY: mat_peptide
<222> LOCATION: (790)..(2538)
<220> FEATURE:
<221> NAME/KEY: sig_peptide
<222> LOCATION: (724)..(790)

<400> SEQUENCE: 6
ctgcaggtac ctgaagcctg cctagtttga tcaccctgaa accagcactg cctgtcttga             60
ccttggtggt gagtttgcac gtgggctggc tgttcaaata aactctccaa ttgaccctct            120
ccccgtggag aacacagcaa acactatagg ctttccattg agggcatgac gaggacccta            180
tggtttgtgc acttggcgag ggctgaccgg agcacgaatc gggaagggca gaactcagaa            240
ttcggtgttc tcggcatgcc gaaagtcggt atcccttggc gccacgatga tttgcgtcca           300
ggattcgtat agttcctcgt ccacgaggct gcctaccgtc agcgtgaggc agtgagctaa           360
tatgggccca ataagccact acgaggatga catggcctct acagaacgag agacgcagag            420
gatcaggacg ccaatcctgc gctccacctg tctaaggatt cgcttttgga ctatccaggg           480
attatggctt cggattattg tattcgggat accgacggct gagcacacgg aggatgaggt           540
tcagctcacg gcccctatca gtatgcatta tgaggatggc ttcttggaaa gcagaggaat            600
tggattatcg aacaagttgg ttctggacca ttgactcgag cgtataagta acctcgttcg            660
gtcctcctgt caccttctga tcagcaacca gcctttcctc tctcattccc tcatctgccc            720 atc atg cag act ctc ctt gtg agc tcg ctt gtg gtc tcc ctc gct gcg             768
    Met Gln Thr Leu Leu Val Ser Ser Leu Val Val Ser Leu Ala Ala
        -20             -15                 -10
```

```
                                                                         -continued gcc ctg cca cac tac atc agg agc aat ggc att gaa gcc agc ctc ctg         816
Ala Leu Pro His Tyr Ile Arg Ser Asn Gly Ile Glu Ala Ser Leu Leu
        -5              -1  1               5 act gat ccc aag gat gtc tcc ggc cgc acg gtc gac tac atc atc gct         864
Thr Asp Pro Lys Asp Val Ser Gly Arg Thr Val Asp Tyr Ile Ile Ala
 10              15              20              25 ggt gga ggt ctg act gga ctc acc acc gct gct cgt ctg acg gag aac         912
Gly Gly Gly Leu Thr Gly Leu Thr Thr Ala Ala Arg Leu Thr Glu Asn
            30              35              40 ccc aac atc agt gtg ctc gtc atc gaa agt ggc tcc tac gag tcg gac         960
Pro Asn Ile Ser Val Leu Val Ile Glu Ser Gly Ser Tyr Glu Ser Asp
                45              50              55 aga ggt cct atc att gag gac ctg aac gcc tac ggc gac atc ttt ggc        1008
Arg Gly Pro Ile Ile Glu Asp Leu Asn Ala Tyr Gly Asp Ile Phe Gly
            60              65              70 agc agt gta gac cac gcc tac gag acc gtg gag ctc gct acc aac aat        1056
Ser Ser Val Asp His Ala Tyr Glu Thr Val Glu Leu Ala Thr Asn Asn
 75              80              85 caa acc gcg ctg atc cgc tcc gga aat ggt ctc ggt ggc tct act cta        1104
Gln Thr Ala Leu Ile Arg Ser Gly Asn Gly Leu Gly Gly Ser Thr Leu
 90              95             100             105 gtg aat ggt ggc acc tgg act cgc ccc cac aag gca cag gtt gac tct        1152
Val Asn Gly Gly Thr Trp Thr Arg Pro His Lys Ala Gln Val Asp Ser
            110             115             120 tgg gag act gtc ttt gga aat gag ggc tgg aac tgg gac aat gtg gcc        1200
Trp Glu Thr Val Phe Gly Asn Glu Gly Trp Asn Trp Asp Asn Val Ala
            125             130             135 gcc tac tcc ctc cag gct gag cgt gct cgc gca cca aat gcc aaa cag        1248
Ala Tyr Ser Leu Gln Ala Glu Arg Ala Arg Ala Pro Asn Ala Lys Gln
            140             145             150 atc gct gct ggc cac tac ttc aac gca tcc tgc cat ggt gtt aat ggt        1296
Ile Ala Ala Gly His Tyr Phe Asn Ala Ser Cys His Gly Val Asn Gly
155             160             165 act gtc cat gcc gga ccc cgc gac acc ggc gat gac tat tct ccc atc        1344
Thr Val His Ala Gly Pro Arg Asp Thr Gly Asp Asp Tyr Ser Pro Ile
170             175             180             185 gtc aag gct ctc atg agc gct gtc gaa gac cgg ggc gtt ccc acc aag        1392
Val Lys Ala Leu Met Ser Ala Val Glu Asp Arg Gly Val Pro Thr Lys
            190             195             200 aaa gac ttc gga tgc ggt gac ccc cat ggt gtg tcc atg ttc ccc aac        1440
Lys Asp Phe Gly Cys Gly Asp Pro His Gly Val Ser Met Phe Pro Asn
            205             210             215 acc ttg cac gaa gac caa gtg cgc tcc gat gcc gct cgc gaa tgg cta        1488
Thr Leu His Glu Asp Gln Val Arg Ser Asp Ala Ala Arg Glu Trp Leu
            220             225             230 ctt ccc aac tac caa cgt ccc aac ctg caa gtc ctg acc gga cag tat        1536
Leu Pro Asn Tyr Gln Arg Pro Asn Leu Gln Val Leu Thr Gly Gln Tyr
            235             240             245 gtt ggt aag gtg ctc ctt agc cag aac ggc acc acc cct cgt gcc gtt        1584
Val Gly Lys Val Leu Leu Ser Gln Asn Gly Thr Thr Pro Arg Ala Val
250             255             260             265 ggc gtg gaa ttc ggc acc cac aag ggc aac acc cac aac gtt tac gct        1632
Gly Val Glu Phe Gly Thr His Lys Gly Asn Thr His Asn Val Tyr Ala
            270             275             280 aag cac gag gtc ctc ctg gcc gcg ggc tcc gct gtc tct ccc aca atc        1680
Lys His Glu Val Leu Leu Ala Ala Gly Ser Ala Val Ser Pro Thr Ile
            285             290             295 ctc gaa tat tcc ggt atc gga atg aag tcc atc ctg gag ccc ctt ggt        1728
Leu Glu Tyr Ser Gly Ile Gly Met Lys Ser Ile Leu Glu Pro Leu Gly
 300             305             310
```

```
atc gac acc gtc gtt gac ctg ccc gtc ggc ttg aac ctg cag gac cag      1776
Ile Asp Thr Val Val Asp Leu Pro Val Gly Leu Asn Leu Gln Asp Gln
    315                 320                 325 acc acc gct acc gtc cgc tcc cgc atc acc tct gct ggt gca gga cag      1824
Thr Thr Ala Thr Val Arg Ser Arg Ile Thr Ser Ala Gly Ala Gly Gln
330                 335                 340                 345 gga cag gcc gct tgg ttc gcc acc ttc aac gag acc ttt ggt gac tat      1872
Gly Gln Ala Ala Trp Phe Ala Thr Phe Asn Glu Thr Phe Gly Asp Tyr
                350                 355                 360 tcc gaa aag gca cac gag ctg ctc aac acc aag ctg gag cag tgg gcc      1920
Ser Glu Lys Ala His Glu Leu Leu Asn Thr Lys Leu Glu Gln Trp Ala
    365                 370                 375 gaa gag gcc gtc gcc cgt ggc gga ttc cac aac acc acc gcc ttg ctc      1968
Glu Glu Ala Val Ala Arg Gly Gly Phe His Asn Thr Thr Ala Leu Leu
380                 385                 390 atc cag tac gag aac tac cgc gac tgg att gtc aac cac aac gtc gcg      2016
Ile Gln Tyr Glu Asn Tyr Arg Asp Trp Ile Val Asn His Asn Val Ala
    395                 400                 405 tac tcg gaa ctc ttc ctc gac act gcc gga gta gcc agc ttc gat gtg      2064
Tyr Ser Glu Leu Phe Leu Asp Thr Ala Gly Val Ala Ser Phe Asp Val
410                 415                 420                 425 tgg gac ctt ctg ccc ttc acc cga gga tac gtt cac atc ctc gac aag      2112
Trp Asp Leu Leu Pro Phe Thr Arg Gly Tyr Val His Ile Leu Asp Lys
                430                 435                 440 gac ccc tac ctt cac cac ttc gcc tac gac cct cag tac ttc ctc aac      2160
Asp Pro Tyr Leu His His Phe Ala Tyr Asp Pro Gln Tyr Phe Leu Asn
    445                 450                 455 gag ctg gac ctg ctc ggt cag gct gcc gct act caa ctg gcc cgc aac      2208
Glu Leu Asp Leu Leu Gly Gln Ala Ala Ala Thr Gln Leu Ala Arg Asn
460                 465                 470 atc tcc aac tcc ggt gcc atg cag acc tac ttc gct ggg gag act atc      2256
Ile Ser Asn Ser Gly Ala Met Gln Thr Tyr Phe Ala Gly Glu Thr Ile
    475                 480                 485 ccc ggt gat aac ctc gcg tat gat gcc gat ttg agc gcc tgg act gag      2304
Pro Gly Asp Asn Leu Ala Tyr Asp Ala Asp Leu Ser Ala Trp Thr Glu
490                 495                 500                 505 tac atc ccg tac cac ttc cgt cct aac tac cat ggc gtg ggt act tgc      2352
Tyr Ile Pro Tyr His Phe Arg Pro Asn Tyr His Gly Val Gly Thr Cys
                510                 515                 520 tcc atg atg ccg aag gag atg ggc ggt gtt gtt gat aat gct gcc cgt      2400
Ser Met Met Pro Lys Glu Met Gly Gly Val Val Asp Asn Ala Ala Arg
    525                 530                 535 gtg tat ggt gtg cag gga ctg cgt gtc att gat ggt tct att cct cct      2448
Val Tyr Gly Val Gln Gly Leu Arg Val Ile Asp Gly Ser Ile Pro Pro
540                 545                 550 acg caa atg tcg tcc cat gtc atg acg gtg ttc tat gcc atg gcg cta      2496
Thr Gln Met Ser Ser His Val Met Thr Val Phe Tyr Ala Met Ala Leu
    555                 560                 565 aaa att tcg gat gct atc ttg gaa gat tat gct tcc atg cag              2538
Lys Ile Ser Asp Ala Ile Leu Glu Asp Tyr Ala Ser Met Gln
570                 575                 580 tgagtggtat gatggggata tgagtgagga tattagggga tggtacttag atgctgggga   2598
ggtataatca tagattggat agaattggta ggttacatag acaggttaca tgaatagacg   2658
ttcgttatat gtgagcagac attactacca acaagggca ttgttcagtt agtcgaacga    2718
tagtcatatg ttttgtacgg gaagaaagtt tcactaatta ttaagcaaac ggatcagggg   2778
ttgccagcta aaatacaatc atccgatgtt ctatttttctt caaattgatc gaccagtcag  2838
ttaatgaatg catgagagca actctgcgca tcctctagct atctagtcaa taataagcat   2898
```

-continued

```
gttgtttaag atgaaacacc gccatagaca tattctgttg ctggtgaagc aagccctcgc    2958
taaatatgct gataacttcc tatgccagta gaatattttc ccactctgct gcgcgctctc    3018
aaaagctt                                                             3026
```

<210> SEQ ID NO 7
<211> LENGTH: 1517
<212> TYPE: DNA
<213> ORGANISM: Aspergillus niger
<220> FEATURE:
<221> NAME/KEY: CDS
<222> LOCATION: (339)..(495)
<220> FEATURE:
<221> NAME/KEY: CDS
<222> LOCATION: (564)..(1237)

<400> SEQUENCE: 7

```
gcagggaaaa atacgagctc caatgaacct gggtgtggca acttcaatgg aaaggaactg     60
cctttgcagg tgtggctgaa ccccacggtt ccggtcggag gcggcgaaat cacccgatgt    120
ggctggtgcg tggagggtcg cgatgattta ctgagctcct cttttgctcg acattgaatg    180
tgcattgttc acctcatata agggccagtc gctgctaaat tattcggtag tatttgcgca    240
tctctggatc taccaattag ggcctatcag tcgaaactcc aagctactca tattgcacaa    300
gcctctttca tccccgcatt aaccccctcca ccgacacc atg tcc tcc aag tcg caa    356
                                           Met Ser Ser Lys Ser Gln
                                             1               5 ttg acc tac act gcc cgt gcc agc aag cac ccc aat gct ctg gcc aag      404
Leu Thr Tyr Thr Ala Arg Ala Ser Lys His Pro Asn Ala Leu Ala Lys
         10                  15                  20 cgg ctg ttc gaa att gct gag gcc aag aag acc aat gtg acc gtc tct      452
Arg Leu Phe Glu Ile Ala Glu Ala Lys Lys Thr Asn Val Thr Val Ser
     25                  30                  35 gcc gac gtt acc acc act aag gag cta cta gat ctt gct gac c             495
Ala Asp Val Thr Thr Thr Lys Glu Leu Leu Asp Leu Ala Asp
 40                  45                  50 gtaggccgac cgccattct gcctgtttat gctgcataca aacttattaa cggtgatacc      555 ggactgag gt ctc ggt ccc tac atc gcc gtg atc aaa acc cac atc gat      604
            Arg Leu Gly Pro Tyr Ile Ala Val Ile Lys Thr His Ile Asp
                 55                  60                  65 atc ctc tct gac ttc agc gac gag acc att gag ggc ctc aag gct ctt      652
Ile Leu Ser Asp Phe Ser Asp Glu Thr Ile Glu Gly Leu Lys Ala Leu
         70                  75                  80 gcg cag aag cac aac ttc ctc atc ttc gag gac cgc aaa ttc atc gac      700
Ala Gln Lys His Asn Phe Leu Ile Phe Glu Asp Arg Lys Phe Ile Asp
     85                  90                  95 att ggc aac act gtc cag aag caa tac cac cgt ggt acc ctc cgc atc      748
Ile Gly Asn Thr Val Gln Lys Gln Tyr His Arg Gly Thr Leu Arg Ile
100                 105                 110 tca gaa tgg gcc cat atc atc aac tgc agc atc ctg cct ggc gag ggt      796
Ser Glu Trp Ala His Ile Ile Asn Cys Ser Ile Leu Pro Gly Glu Gly
115                 120                 125                 130 atc gtc gag gct ctc gct cag acg gcg tct gca ccg gac ttc tcc tac      844
Ile Val Glu Ala Leu Ala Gln Thr Ala Ser Ala Pro Asp Phe Ser Tyr
             135                 140                 145 ggc ccc gaa cgt ggt ctg ttg atc ttg gcg gaa atg acc tct aag ggt      892
Gly Pro Glu Arg Gly Leu Leu Ile Leu Ala Glu Met Thr Ser Lys Gly
         150                 155                 160 tcc ttg gcc acc ggc cag tac act act tct tcg gtt gat tat gcc cgg      940
Ser Leu Ala Thr Gly Gln Tyr Thr Thr Ser Ser Val Asp Tyr Ala Arg
     165                 170                 175
```

```
aaa tac aag aac ttc gtc atg gga ttt gtg tcg acc cgc tcg ttg ggt      988
Lys Tyr Lys Asn Phe Val Met Gly Phe Val Ser Thr Arg Ser Leu Gly
180                 185                 190 gag gtg cag tcg gaa gtc agc tct cct tcg gat gag gag gac ttt gtg     1036
Glu Val Gln Ser Glu Val Ser Ser Pro Ser Asp Glu Glu Asp Phe Val
195                 200                 205                 210 gtc ttc acg act ggt gtg aac att tcg tcc aag gga gat aag ctc ggt     1084
Val Phe Thr Thr Gly Val Asn Ile Ser Ser Lys Gly Asp Lys Leu Gly
            215                 220                 225 cag cag tac cag act ccc gca tcg gct atc ggt cgg ggt gct gac ttc     1132
Gln Gln Tyr Gln Thr Pro Ala Ser Ala Ile Gly Arg Gly Ala Asp Phe
        230                 235                 240 att atc gcg ggt cgc ggt atc tac gcc gcg ccg gac ccg gtg cag gct     1180
Ile Ile Ala Gly Arg Gly Ile Tyr Ala Ala Pro Asp Pro Val Gln Ala
            245                 250                 255 gcg caa cag tac cag aag gaa ggt tgg gag gcg tac ctg gcc cgt gtc     1228
Ala Gln Gln Tyr Gln Lys Glu Gly Trp Glu Ala Tyr Leu Ala Arg Val
260                 265                 270 ggc gga aac taatactata aaatgaggaa aaaagttttg atggttatga              1277
Gly Gly Asn
275 atgatataga aatgcaactt gccgctacga tacgcataca aactaatgtc gagcacgggt   1337 agtcagactg cggcatcgga tgtcaaaacg gtattgatcc tgcaggctat tagggtgg    1397 cacgggatta atgcggtacg acgatttgat gcagataagc aggctgcgaa gtacttagtc  1457 ctgtaactct tgcgtagagc aaatggcgac gggtggctga taagggacgg tgataagctt  1517

<210> SEQ ID NO 8
<211> LENGTH: 4108
<212> TYPE: DNA
<213> ORGANISM: Aspergillus niger
<220> FEATURE:
<221> NAME/KEY: CDS
<222> LOCATION: (855)..(3266)
<220> FEATURE:
<221> NAME/KEY: sig_peptide
<222> LOCATION: (855)..(932)
<220> FEATURE:
<221> NAME/KEY: mat_peptide
<222> LOCATION: (933)..(3266)

<400> SEQUENCE: 8
ctgcaggcca tgtatcctgc gaagatgggt gagtggaaga aaatcgtcaa gattgaggcg     60
gagatggcga gggccgcgat gaagaagggt ggctgggcac cggagaagcc agccaccgcc    120
acggcggcgc agatgagtat accgtatgcg gtggcgttgc aggttctgga tggggagatt    180 gtgccgggc agtttgcgcc gggcatgttg aatcggagg agttatggga tgtgattagg     240
ctggtggaat gtcgggaggc caaggagctg ataatacgt gggcgcagag ggtcaagatc     300
acgtttgagg atggggaggt ggtggagaag ttgttgaagg ctccgaaggg agtccatcct    360
ggggtgacga atgaggaggt gttgcagaag tggcgggctg tgacgaaggg ggtaaatttcg   420 gaagagaggc agaagaagat cgaggagatt tgttgaatt tggaagaggt ggaggatgtg    480
gctggtgttt tgggcgagtt gttgagggaa gagacggtga atgtgctgca gtagacggtt   540
accccatttg gacggggatg gcttcatatt tcccaagcga tgtcacgcca tagaaagggc   600
acatttaccc ggtgcctgag cgaaactcta cttcgaagac aatgccaatg tttaactatc   660 ttgtttttaat tgctaaatgc aaacattcca ggttcttcct aatgccggct aaatcattca    720
ggctaaaccc ccgcgatgaa gtcaatcggt cattctccgg cgcatctccg catctccgca    780
aaccgctata aaatctaccc cagattcagt ccccggccac ctttctatcc ccccccccac    840
```

```
agactggctc aacc atg gcg cac tca atg tct cgt ccc gtg gct gcc act    890
              Met Ala His Ser Met Ser Arg Pro Val Ala Ala Thr
                  -25             -20             -15 gcc gct gct ctg ctg gct ctg gct ctt cct caa gct ctt gcc cag gcc    938
Ala Ala Ala Leu Leu Ala Leu Ala Leu Pro Gln Ala Leu Ala Gln Ala
            -10              -5              -1   1 aac acc agc tac gtc gac tac aac atc gaa gcc aac ccg gac ttg tat    986
Asn Thr Ser Tyr Val Asp Tyr Asn Ile Glu Ala Asn Pro Asp Leu Tyr
             5               10              15 cct ttg tgc ata gaa acc atc cca ctg agc ttc ccc gac tgc cag aat   1034
Pro Leu Cys Ile Glu Thr Ile Pro Leu Ser Phe Pro Asp Cys Gln Asn
         20              25              30 ggt ccc ctg cgc agc cat ctc atc tgt gat gaa aca gcc acc ccc tat   1082
Gly Pro Leu Arg Ser His Leu Ile Cys Asp Glu Thr Ala Thr Pro Tyr
 35              40              45              50 gac cga gca gca tcg ctc atc tcg ctc ttc acc ctg gac gag ctg atc   1130
Asp Arg Ala Ala Ser Leu Ile Ser Leu Phe Thr Leu Asp Glu Leu Ile
                 55              60              65 gcc aac acc ggc aac acc ggc ctc ggt gtc tcc cga ctg ggc ctc cct   1178
Ala Asn Thr Gly Asn Thr Gly Leu Gly Val Ser Arg Leu Gly Leu Pro
             70              75              80 gca tac caa gta tgg agt gaa gct ctt cac ggc ctc gac cgt gcc aat   1226
Ala Tyr Gln Val Trp Ser Glu Ala Leu His Gly Leu Asp Arg Ala Asn
         85              90              95 ttc agc gac tca gga gcc tac aat tgg gcc acc tca ttc ccc cag ccc   1274
Phe Ser Asp Ser Gly Ala Tyr Asn Trp Ala Thr Ser Phe Pro Gln Pro
100             105             110 atc ctg acc acc gcg gcc ctc aac cgc acc ctc atc cac caa atc gcc   1322
Ile Leu Thr Thr Ala Ala Leu Asn Arg Thr Leu Ile His Gln Ile Ala
115             120             125             130 tcc atc atc tct acc caa ggc cgc gcc ttc aac aac gcc ggc cgc tac   1370
Ser Ile Ile Ser Thr Gln Gly Arg Ala Phe Asn Asn Ala Gly Arg Tyr
                135             140             145 ggc ctc gac gtc tac gcc ccc aac atc aac acc ttc cgc cac ccc gtc   1418
Gly Leu Asp Val Tyr Ala Pro Asn Ile Asn Thr Phe Arg His Pro Val
             150             155             160 tgg ggt cgc gga caa gaa acc cca gga gag gac gtc tct ctc gcc gcc   1466
Trp Gly Arg Gly Gln Glu Thr Pro Gly Glu Asp Val Ser Leu Ala Ala
         165             170             175 gtc tac gcc tac gaa tac atc acc ggc atc cag ggt ccc gac cca gaa   1514
Val Tyr Ala Tyr Glu Tyr Ile Thr Gly Ile Gln Gly Pro Asp Pro Glu
180             185             190 tca aac ctc aaa ctc gcc gcc acg gcc aag cac tac gcc ggc tat gac   1562
Ser Asn Leu Lys Leu Ala Ala Thr Ala Lys His Tyr Ala Gly Tyr Asp
195             200             205             210 atc gag aac tgg cac aac cac tcc cgc ctg ggc aac gac atg aac atc   1610
Ile Glu Asn Trp His Asn His Ser Arg Leu Gly Asn Asp Met Asn Ile
             215             220             225 acc cag caa gac ctc tcc gaa tac tac acg ccc caa ttc cac gtc gcc   1658
Thr Gln Gln Asp Leu Ser Glu Tyr Tyr Thr Pro Gln Phe His Val Ala
         230             235             240 gcc cgc gac gcc aaa gtc cag agt gtc atg tgc gcc tac aac gcc gtc   1706
Ala Arg Asp Ala Lys Val Gln Ser Val Met Cys Ala Tyr Asn Ala Val
     245             250             255 aac ggc gtc cct gcc tgc gcc gac tcc tac ttc ctc cag acc ctc ctc   1754
Asn Gly Val Pro Ala Cys Ala Asp Ser Tyr Phe Leu Gln Thr Leu Leu
260             265             270 cgc gac acc ttc gga ttt gtc gac cac gga tac gtc tcc agc gac tgc   1802
Arg Asp Thr Phe Gly Phe Val Asp His Gly Tyr Val Ser Ser Asp Cys
275             280             285             290
```

```
gat gcc gcc tat aac atc tac aac ccc cac ggc tat gcc tcc tcc cag      1850
Asp Ala Ala Tyr Asn Ile Tyr Asn Pro His Gly Tyr Ala Ser Ser Gln
                295                 300                 305 gct gcc gct gcc gct gag gcc atc ctc gcc ggc acc gac atc gac tgc      1898
Ala Ala Ala Ala Ala Glu Ala Ile Leu Ala Gly Thr Asp Ile Asp Cys
            310                 315                 320 ggt acc acc tac caa tgg cac ctg aac gag tcc atc gct gcg gga gat      1946
Gly Thr Thr Tyr Gln Trp His Leu Asn Glu Ser Ile Ala Ala Gly Asp
        325                 330                 335 ctc tct cgc gat gat att gag cag ggt gtg att cgt ctc tac acg acc      1994
Leu Ser Arg Asp Asp Ile Glu Gln Gly Val Ile Arg Leu Tyr Thr Thr
    340                 345                 350 ctc gtg cag gcc gga tac ttc gac tcc aac acc aca aag gcg aac aac      2042
Leu Val Gln Ala Gly Tyr Phe Asp Ser Asn Thr Thr Lys Ala Asn Asn
355                 360                 365                 370 ccc tac cgc gac ctc tcc tgg tcc gac gtc ctt gag acg gac gca tgg      2090
Pro Tyr Arg Asp Leu Ser Trp Ser Asp Val Leu Glu Thr Asp Ala Trp
                375                 380                 385 aac atc tcc tac caa gcc gcg acg cag ggc att gtc ctt ctc aag aac      2138
Asn Ile Ser Tyr Gln Ala Ala Thr Gln Gly Ile Val Leu Leu Lys Asn
            390                 395                 400 tcc aac aac gtc ctc ccc ctc acc gag aaa gct tac cca cca tcc aac      2186
Ser Asn Asn Val Leu Pro Leu Thr Glu Lys Ala Tyr Pro Pro Ser Asn
        405                 410                 415 acc acc gtc gcc ctc atc ggt ccc tgg gcc aac gcc acc acc caa ctc      2234
Thr Thr Val Ala Leu Ile Gly Pro Trp Ala Asn Ala Thr Thr Gln Leu
    420                 425                 430 ctg ggc aac tac tac ggc aac gct ccc tac atg atc agc ccc cgc gcc      2282
Leu Gly Asn Tyr Tyr Gly Asn Ala Pro Tyr Met Ile Ser Pro Arg Ala
435                 440                 445                 450 gcc ttc gaa gaa gcc gga tac aaa gtc aac ttc gcc gag ggc acc ggt      2330
Ala Phe Glu Glu Ala Gly Tyr Lys Val Asn Phe Ala Glu Gly Thr Gly
                455                 460                 465 atc tcc tcc aca agc acc tcg ggc ttc gct gcc gcc tta tcc gcc gca      2378
Ile Ser Ser Thr Ser Thr Ser Gly Phe Ala Ala Ala Leu Ser Ala Ala
            470                 475                 480 caa tcc gcc gac gtg ata atc tac gcc ggt ggt atc gac aat acc ctt      2426
Gln Ser Ala Asp Val Ile Ile Tyr Ala Gly Gly Ile Asp Asn Thr Leu
        485                 490                 495 gaa gcg gag gca ctg gat cga gag agt atc gcg tgg ccg ggt aac caa      2474
Glu Ala Glu Ala Leu Asp Arg Glu Ser Ile Ala Trp Pro Gly Asn Gln
    500                 505                 510 ctg gac ttg atc cag aag ctc gcc tcg gcg gcc gga aag aag ccg ctc      2522
Leu Asp Leu Ile Gln Lys Leu Ala Ser Ala Ala Gly Lys Lys Pro Leu
515                 520                 525                 530 atc gtc ctc caa atg ggc ggc gga cag gtc gat tcc tct tcg ctc aag      2570
Ile Val Leu Gln Met Gly Gly Gly Gln Val Asp Ser Ser Ser Leu Lys
                535                 540                 545 aac aac acc aat gtt tct gca ctt ctc tgg ggc gga tac ccc ggc caa      2618
Asn Asn Thr Asn Val Ser Ala Leu Leu Trp Gly Gly Tyr Pro Gly Gln
            550                 555                 560 tct ggc ggc ttc gct ttg cgg gat atc atc acg ggg aag aag aac ccc      2666
Ser Gly Gly Phe Ala Leu Arg Asp Ile Ile Thr Gly Lys Lys Asn Pro
        565                 570                 575 gcg ggt aga cta gtc acg acg cag tac cct gcc agc tac gcg gag gag      2714
Ala Gly Arg Leu Val Thr Thr Gln Tyr Pro Ala Ser Tyr Ala Glu Glu
    580                 585                 590 ttc ccg gcg aca gat atg aac ctt cgt cct gag ggt gat aac cct ggt      2762
Phe Pro Ala Thr Asp Met Asn Leu Arg Pro Glu Gly Asp Asn Pro Gly
595                 600                 605                 610
```

```
cag acg tat aaa tgg tac acc ggc gaa gcc gtg tac gag ttc ggc cac    2810
Gln Thr Tyr Lys Trp Tyr Thr Gly Glu Ala Val Tyr Glu Phe Gly His
            615                 620                 625 ggg tta ttc tac acg acc ttc gcg gaa tcc tcc agc aat acc act aca    2858
Gly Leu Phe Tyr Thr Thr Phe Ala Glu Ser Ser Ser Asn Thr Thr Thr
        630                 635                 640 aag gaa gtt aag ctc aac atc cag gac att ctt tcc cag aca cac gaa    2906
Lys Glu Val Lys Leu Asn Ile Gln Asp Ile Leu Ser Gln Thr His Glu
    645                 650                 655 gac ctg gcg tcg att acc cag ctc cct gtg ctg aac ttc acc gcc aat    2954
Asp Leu Ala Ser Ile Thr Gln Leu Pro Val Leu Asn Phe Thr Ala Asn
660                 665                 670 atc agg aac act gga aag ctg gaa tcg gat tac acc gct atg gta ttc    3002
Ile Arg Asn Thr Gly Lys Leu Glu Ser Asp Tyr Thr Ala Met Val Phe
675                 680                 685                 690 gcc aat acc tct gat gcc ggg ccg gcg ccg tat ccc aag aag tgg ctg    3050
Ala Asn Thr Ser Asp Ala Gly Pro Ala Pro Tyr Pro Lys Lys Trp Leu
                695                 700                 705 gtc ggg tgg gat cgg ctt ggg gag gtg aag gtc ggg gag acg agg gag    3098
Val Gly Trp Asp Arg Leu Gly Glu Val Lys Val Gly Glu Thr Arg Glu
            710                 715                 720 ttg agg gtc ccc gtt gag gtg ggg agc ttt gcg agg gtg aat gag gat    3146
Leu Arg Val Pro Val Glu Val Gly Ser Phe Ala Arg Val Asn Glu Asp
        725                 730                 735 ggc gat tgg gtg gtg ttt ccg gga acg ttt gag ttg gcg ttg aat ttg    3194
Gly Asp Trp Val Val Phe Pro Gly Thr Phe Glu Leu Ala Leu Asn Leu
    740                 745                 750 gag agg aag gtt cgg gtg aag gtt gtt ctt gag ggt gag gag gaa gtc    3242
Glu Arg Lys Val Arg Val Lys Val Val Leu Glu Gly Glu Glu Glu Val
755                 760                 765                 770 gtg ctg aag tgg ccg ggg aag gag tagaaaatac tattctgttg atggctctag   3296
Val Leu Lys Trp Pro Gly Lys Glu
                775 gggatgagag tcagcctatt actggatatg catagtggtg atacgatgta tatagctcta  3356 tgaagtaatt agttcaagtg gaataccccc tttcacacat atagtatgct gttattccga  3416 aatagggatc atttctgatt aatagtagcg gtagcgatgg tcacacacga cttaatgttc  3476 cccattgtac cggaagtaac aattccagtg acctcttaga agaaagacag caagaaaaag  3536 taagaaaggg aaattgatca aaaataagg ccatctacag cctattcaca tttagccgga   3596 tctgcaatac agctacagaa ataaagtttg ttaggctgct tgctagcata gctcctacta  3656 tactaaacca acacaatggg acaataccc aattaaccag ccctcactca acacaagtga   3716 atcctaccga caacatgcat aaaccactgc ttccccaccc agcacccttc ttcacgatca  3776 gatcacggag aattaccaac tactcttcgc ataaaacgta acaacggcc tcgggccagg   3836 atccgtccga ctcaaaagca acaaatccct cgttcgcata ctagccacat gaacctgttg  3896 ctccgagacc tcctcaactg ggtcttcaaa tgccagaag acgctttctt ctcgatatcc    3956 atcggatact cgctggccgc ttagacatat gaacgatgag tctcgtctgc aaaggaaac   4016 aaccgtgttc ccgaatccag tgtcaaagtc gtaggtctgg aatttgaaaa gtgttcgggc  4076 gtttccttgg agggtcggga gtgcgactgc ag                                4108
```

<210> SEQ ID NO 9
<211> LENGTH: 4173
<212> TYPE: DNA
<213> ORGANISM: Aspergillus niger
<220> FEATURE:
<221> NAME/KEY: CDS
<222> LOCATION: (948)..(1173)
<220> FEATURE:
<221> NAME/KEY: CDS
<222> LOCATION: (1238)..(3495)
<220> FEATURE:
<221> NAME/KEY: CDS
<222> LOCATION: (3550)..(3690)

<400> SEQUENCE: 9

| | |
|---|---|
| cccgggcttg gttggtctcc gtctggcttc cccgccttt tcccctgcaa ttctgcatcc | 60 |
| ccaatccttc tttttctttt gcctcgccag gctgtgtctt ttttccccct cccctcctc | 120 |
| cctcgtcagc ttctcttcga cagcatgcgt gagggtctgc taccaactac aatccttgtt | 180 |
| ctcactgtct gatggtctga cccgaccgtg gtgtctgtgg tgtgtgtgtg agagagaaag | 240 |
| gaaagctagt cagtccagtc actctttctc gtgggttctt caccttcccc ggacctgccc | 300 |
| tccgacacta aaagccact tccccccaac tggttagttg ctgctagtct ccttagttca | 360 |
| tggtcggcct gtcgcttct ccggctgaca ttctcctctt ctgctgcctt ctaggtccct | 420 |
| gttttttagt ccctgtttta gttgccccgc agactgaatc ggcaatgccg tggagttgat | 480 |
| cgttccgtgg tttccttgcg accgctcctc tgcttcatca tcttttttcct cctgccctcc | 540 |
| tggtcttgaa tcgcctggcc ctcgtctagg atctgttgcg ccagtgtcgc cttaatctcc | 600 |
| tttcccgcta gcgtagtgcc ctttcacgct tgggccctta cggccctttcc attgccagc | 660 |
| ggtctgaata cctcactttc cccccaacg accggggtct tcatgacccg ctggggtgat | 720 |
| tgttccgccc ggtgaggatg tcaacccct cgattcctca attcaccagt cctttctctc | 780 |
| ccttctcttc cggatcgcac tcgactggca tggcgccgtc tcagactgtc gggttggata | 840 |
| cgctcgccga gggctcgcag tacgtcctgg aacaattgca gctgtcgcga gacgctgcgg | 900 |
| gaaccggtgc cggcgatggc gcgacctcca cttccttgcg aaattcc atg tcg cat | 956 |

Met Ser His
1

| | |
|---|---|
| acg aag gat caa cca ccc ttt gat aat gag aag aac cag agc act ggc | 1004 |
| Thr Lys Asp Gln Pro Pro Phe Asp Asn Glu Lys Asn Gln Ser Thr Gly | |
| 5 10 15 | |
| tcg ggt ttt agg gac gct ctg caa aga gat ccc ctc gtg gag gct cgc | 1052 |
| Ser Gly Phe Arg Asp Ala Leu Gln Arg Asp Pro Leu Val Glu Ala Arg | |
| 20 25 30 35 | |
| tct gcc gtc cgc aaa acc tcg tct tca gct ccg gtt cgc cgc cga atc | 1100 |
| Ser Ala Val Arg Lys Thr Ser Ser Ser Ala Pro Val Arg Arg Arg Ile | |
| 40 45 50 | |
| agc cgt gcg tgt gac cag tgt aac caa ctc cga acg aaa tgc gac ggg | 1148 |
| Ser Arg Ala Cys Asp Gln Cys Asn Gln Leu Arg Thr Lys Cys Asp Gly | |
| 55 60 65 | |
| cag cat ccg tgc gct cat tgc att g gtaggcttcc gctctttctc | 1193 |
| Gln His Pro Cys Ala His Cys Ile | |
| 70 75 | |
| cgatgccggc gatgaggcgg acgcttgact gacctgttct gtag aa ttc gga ctg | 1248 |
| Glu Phe Gly Leu | |
| acc tgc gag tat gcg cga gaa cgc aag aag cgt gga aaa gcg tcg aag | 1296 |
| Thr Cys Glu Tyr Ala Arg Glu Arg Lys Lys Arg Gly Lys Ala Ser Lys | |
| 80 85 90 95 | |
| aag gat ctg gcg gcg gca gct gcg gcg gct acc caa ggg tcg aat ggt | 1344 |
| Lys Asp Leu Ala Ala Ala Ala Ala Ala Ala Thr Gln Gly Ser Asn Gly | |
| 100 105 110 | |
| cat tcc ggg cag gcc aac gcg tcg cta atg ggc gag cga acg tcg gaa | 1392 |
| His Ser Gly Gln Ala Asn Ala Ser Leu Met Gly Glu Arg Thr Ser Glu | |
| 115 120 125 | |
| gac agc cgg cca gga caa gac gtg aac ggc aca tac gac tcg gct ttt | 1440 |

```
                Asp Ser Arg Pro Gly Gln Asp Val Asn Gly Thr Tyr Asp Ser Ala Phe
                        130                 135                 140 gag agc cac cat ctt agc tcg cag cca tcg cat atg cag cat gca agc       1488
Glu Ser His His Leu Ser Ser Gln Pro Ser His Met Gln His Ala Ser
145                 150                 155 act gca ggg ata tcc ggc ctg cac gag tct cag acg gca ccg tcg cat       1536
Thr Ala Gly Ile Ser Gly Leu His Glu Ser Gln Thr Ala Pro Ser His
160                 165                 170                 175 tcg caa tca tcg cta gga acg act atc gat gcg atg cat ttg aat cat       1584
Ser Gln Ser Ser Leu Gly Thr Thr Ile Asp Ala Met His Leu Asn His
                180                 185                 190 ttc aac acg atg aac gat tcc ggt cgc ccg gca atg tcc ata tcc gat       1632
Phe Asn Thr Met Asn Asp Ser Gly Arg Pro Ala Met Ser Ile Ser Asp
                195                 200                 205 ctg cgt tcg cta ccc ccg tcc gtc tta cca ccg caa gga cta agc tcc       1680
Leu Arg Ser Leu Pro Pro Ser Val Leu Pro Pro Gln Gly Leu Ser Ser
                210                 215                 220 ggg tac aac gcg agc gcc ttc gct ttg gtg aac ccg caa gag ccg ggc       1728
Gly Tyr Asn Ala Ser Ala Phe Ala Leu Val Asn Pro Gln Glu Pro Gly
225                 230                 235 tca cca gct aac cag ttt cgc ttg gga agc tca gcg gaa aac cca acc       1776
Ser Pro Ala Asn Gln Phe Arg Leu Gly Ser Ser Ala Glu Asn Pro Thr
240                 245                 250                 255 gca ccg ttt ctt ggt ctc tcg cct cca gga cag tcg cct gga tgg ctc       1824
Ala Pro Phe Leu Gly Leu Ser Pro Pro Gly Gln Ser Pro Gly Trp Leu
                260                 265                 270 cct ctt ccc tcg cca tct cct gcc aac ttt cct tct ttc agc ttg cat       1872
Pro Leu Pro Ser Pro Ser Pro Ala Asn Phe Pro Ser Phe Ser Leu His
                275                 280                 285 ccg ttt tcc agc act tta cga tac cct gtt ttg cag ccg gtc ctg cct       1920
Pro Phe Ser Ser Thr Leu Arg Tyr Pro Val Leu Gln Pro Val Leu Pro
                290                 295                 300 cac atc gcc tcc att att ccg cag tcg cta gcg tgt gac ctt ctg gat       1968
His Ile Ala Ser Ile Ile Pro Gln Ser Leu Ala Cys Asp Leu Leu Asp
305                 310                 315 gtt tac ttc act agt tcc tct tcg tcc cac ctg tct ccc ttg tcc cca       2016
Val Tyr Phe Thr Ser Ser Ser Ser His Leu Ser Pro Leu Ser Pro
320                 325                 330                 335 tac gtg gtg ggc tac atc ttc cgc aag cag tct ttc ctt cac ccg aca       2064
Tyr Val Val Gly Tyr Ile Phe Arg Lys Gln Ser Phe Leu His Pro Thr
                340                 345                 350 aaa ccc cga ata tgc agc ccc ggt ctc ctg gcg agt atg ctc tgg gta       2112
Lys Pro Arg Ile Cys Ser Pro Gly Leu Leu Ala Ser Met Leu Trp Val
                355                 360                 365 gcc gca caa acg agt gaa gct gcg ttt ctg aca tcg ccg ccc tcg gct       2160
Ala Ala Gln Thr Ser Glu Ala Ala Phe Leu Thr Ser Pro Pro Ser Ala
                370                 375                 380 cgg ggg cgt gta tgc cag aaa ctg cta gaa ctg acc att ggt ttg ctc       2208
Arg Gly Arg Val Cys Gln Lys Leu Leu Glu Leu Thr Ile Gly Leu Leu
385                 390                 395 cga ccg ttg gtc cat ggt cct gct acc gga gaa gcg tcg ccc aac tat       2256
Arg Pro Leu Val His Gly Pro Ala Thr Gly Glu Ala Ser Pro Asn Tyr
400                 405                 410                 415 gcg gcg aat atg gtc atc aat ggc gtc gct ctg ggc gga ttt ggg gtc       2304
Ala Ala Asn Met Val Ile Asn Gly Val Ala Leu Gly Gly Phe Gly Val
                420                 425                 430 tcc atg gat cag ctg ggc gcg caa agt agc gcc acc ggc gcc gtg gat       2352
Ser Met Asp Gln Leu Gly Ala Gln Ser Ser Ala Thr Gly Ala Val Asp
                435                 440                 445 gat gta gca act tat gtg cat ctt gcg aca gta gta tcc gcc agc gag       2400
```

-continued

| | | |
|---|---|---|
| Asp Val Ala Thr Tyr Val His Leu Ala Thr Val Val Ser Ala Ser Glu<br>450                        455                        460 | | |
| tac aag gcg gcc agc atg cgc tgg tgg act gcg gcg tgg tct cta gcg<br>Tyr Lys Ala Ala Ser Met Arg Trp Trp Thr Ala Ala Trp Ser Leu Ala<br>465                        470                        475 | 2448 |
| cgt gag ctg aag cta ggc cgt gag ctg cca ccc aat gtt tcc cac gca<br>Arg Glu Leu Lys Leu Gly Arg Glu Leu Pro Pro Asn Val Ser His Ala<br>480                        485                      490                      495 | 2496 |
| cgg caa gat gga gag cga gat ggg gat ggc gag gcg gac aaa cga cat<br>Arg Gln Asp Gly Glu Arg Asp Gly Asp Gly Glu Ala Asp Lys Arg His<br>500                        505                      510 | 2544 |
| cct ccg acc ctc atc acg tca ctg ggt cat gga tcg gga agc tcc ggc<br>Pro Pro Thr Leu Ile Thr Ser Leu Gly His Gly Ser Gly Ser Ser Gly<br>515                        520                        525 | 2592 |
| att aat gtc acc gaa gag gag cgt gag gag cgt cga cgc cta tgg tgg<br>Ile Asn Val Thr Glu Glu Glu Arg Glu Glu Arg Arg Arg Leu Trp Trp<br>530                        535                      540 | 2640 |
| ctc tta tat gcg acc gat cgg cac ctg gcg ctg tgc tac aac cgg ccc<br>Leu Leu Tyr Ala Thr Asp Arg His Leu Ala Leu Cys Tyr Asn Arg Pro<br>545                        550                      555 | 2688 |
| ctc acg ctg ctg gac aag gaa tgt ggc ggg ctg ctg cag ccg atg aac<br>Leu Thr Leu Leu Asp Lys Glu Cys Gly Gly Leu Leu Gln Pro Met Asn<br>560                        565                      570                      575 | 2736 |
| gat gat ctg tgg cag gtc ggc gac ttt gca gcg gct gcc tac cgc cag<br>Asp Asp Leu Trp Gln Val Gly Asp Phe Ala Ala Ala Ala Tyr Arg Gln<br>580                        585                      590 | 2784 |
| gtc gga ccg ccc gtc gag tgt acg ggt cac agc atg tat gga tac ttt<br>Val Gly Pro Pro Val Glu Cys Thr Gly His Ser Met Tyr Gly Tyr Phe<br>595                        600                      605 | 2832 |
| cta ccg ctg atg acg att ctt gga ggg atc gtc gat ctg cac cac gct<br>Leu Pro Leu Met Thr Ile Leu Gly Gly Ile Val Asp Leu His His Ala<br>610                        615                      620 | 2880 |
| gag aat cat ccg cgc ttt ggc ctg gcg ttc cgc aat agc ccg gag tgg<br>Glu Asn His Pro Arg Phe Gly Leu Ala Phe Arg Asn Ser Pro Glu Trp<br>625                        630                      635 | 2928 |
| gag cgt cag gta ctg gac gtt acg cgg cag ctg gac aca tat ggg cgc<br>Glu Arg Gln Val Leu Asp Val Thr Arg Gln Leu Asp Thr Tyr Gly Arg<br>640                        645                      650                      655 | 2976 |
| agc ttg aag gaa ttc gag gcc cgc tac acc agc aac ttg act ctg ggg<br>Ser Leu Lys Glu Phe Glu Ala Arg Tyr Thr Ser Asn Leu Thr Leu Gly<br>660                        665                      670 | 3024 |
| gct acg gat aac gag cct gtc gtc gaa ggt gcc cac ttg gat cac acg<br>Ala Thr Asp Asn Glu Pro Val Val Glu Gly Ala His Leu Asp His Thr<br>675                        680                      685 | 3072 |
| agt cct tcg ggg cgc tcc agc agc acc gtg gga tcg cgg gtg agc gag<br>Ser Pro Ser Gly Arg Ser Ser Ser Thr Val Gly Ser Arg Val Ser Glu<br>690                        695                      700 | 3120 |
| tcc atc gtc cac acg agg atg gtg gtc gcc tac ggg acg cat atc atg<br>Ser Ile Val His Thr Arg Met Val Val Ala Tyr Gly Thr His Ile Met<br>705                        710                      715 | 3168 |
| cac gtc ctg cat att ttg ctc gcg gga aaa tgg gac ccg gtg aat ctg<br>His Val Leu His Ile Leu Leu Ala Gly Lys Trp Asp Pro Val Asn Leu<br>720                        725                      730                      735 | 3216 |
| ttg gaa gat cat gat ctg tgg atc tcc tcg gag tcg ttt gtc tcg gcc<br>Leu Glu Asp His Asp Leu Trp Ile Ser Ser Glu Ser Phe Val Ser Ala<br>740                        745                      750 | 3264 |
| atg agc cat gcg gtc ggt gcc gca gaa gca gcg gca gaa atc ttg gag<br>Met Ser His Ala Val Gly Ala Ala Glu Ala Ala Ala Glu Ile Leu Glu<br>755                        760                      765 | 3312 |
| tac gac ccg gat ctc agc ttc atg ccg ttc ttc ttc ggg att tac cta | 3360 |

```
                Tyr Asp Pro Asp Leu Ser Phe Met Pro Phe Phe Phe Gly Ile Tyr Leu
                        770                 775                 780 cta cag ggc agt ttc ttg ctg cta ctg gcg gcg gac aag ttg cag ggc      3408
Leu Gln Gly Ser Phe Leu Leu Leu Leu Ala Ala Asp Lys Leu Gln Gly
        785                 790                 795 gat gcc agt ccc agt gtc gtg cgg gca tgc gag acg atc gtg cgg gcg      3456
Asp Ala Ser Pro Ser Val Val Arg Ala Cys Glu Thr Ile Val Arg Ala
800                 805                 810                 815 cat gaa gcg tgc gtc gtg acc ttg aac acg gag tac cag gtaggttttc       3505
His Glu Ala Cys Val Val Thr Leu Asn Thr Glu Tyr Gln
                820                 825 ttgtttctct ccctagcttg gcaatagtag ctaacacaat gtag agg aca ttc cgc     3561
                                                 Arg Thr Phe Arg
                                                             830 aag gtc atg cga tcg gcg ctg gca cag gtt cga gga cgc atc cca gag      3609
Lys Val Met Arg Ser Ala Leu Ala Gln Val Arg Gly Arg Ile Pro Glu
            835                 840                 845 gac ttt ggg gag cag cag cag cgc cga cgc gaa gtg ctt gcg cta tac      3657
Asp Phe Gly Glu Gln Gln Gln Arg Arg Arg Glu Val Leu Ala Leu Tyr
        850                 855                 860 cgc tgg agc ggc gat ggc agt ggg ctg gca ctg tagttttgca gtaacacggc    3710
Arg Trp Ser Gly Asp Gly Ser Gly Leu Ala Leu
865                 870                 875 tgatgatgag atgcgattta tggcggtgca ttgaccggtc aatggcttct acattctga     3770 tttgatacta cttttggatt cgctatttca ctccgggctt atgctggctt cattgtcaag    3830
aggggtggca tggcgaatgg aaatatgctt acttcgtgtt gatacggatt cgtacatata    3890
ctttggtgat atatgtggat atttgtggca tgtacactat gcgtgatctt tggacatgat    3950
actttgatac caggtcaatc taattgcgtt cttttcattt gttgcgcaac agccgaggta    4010
tgacgccatg gctgagataa gctgccgata agcattcgca ttccatcctc catcgaagca    4070
ccaaaatctt cttcatataa ccaatccatc aattcaacat tcgtaatgac aatagtataa    4130
tccccaaaat gccctcccta ttacactccc tccgcacttc ccc                      4173

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cacaatgcat cgtataagta acctcgttcg                                     30

<210> SEQ ID NO 11
<211> LENGTH: 875
<212> TYPE: PRT
<213> ORGANISM: Aspergillus niger

<400> SEQUENCE: 11

Met Ser His Thr Lys Asp Gln Pro Pro Phe Asp Asn Glu Lys Asn Gln
1               5                   10                  15

Ser Thr Gly Ser Gly Phe Arg Asp Ala Leu Gln Arg Asp Pro Leu Val
            20                  25                  30

Glu Ala Arg Ser Ala Val Arg Lys Thr Ser Ser Ala Pro Val Arg
        35                  40                  45

Arg Arg Ile Ser Arg Ala Cys Asp Gln Cys Asn Gln Leu Arg Thr Lys
    50                  55                  60
```

```
Cys Asp Gly Gln His Pro Cys Ala His Cys Ile Glu Phe Gly Leu Thr
 65                  70                  75                  80

Cys Glu Tyr Ala Arg Glu Arg Lys Lys Arg Gly Lys Ala Ser Lys Lys
                 85                  90                  95

Asp Leu Ala Ala Ala Ala Ala Ala Thr Gln Gly Ser Asn Gly His
            100                 105                 110

Ser Gly Gln Ala Asn Ala Ser Leu Met Gly Glu Arg Thr Ser Glu Asp
            115                 120                 125

Ser Arg Pro Gly Gln Asp Val Asn Gly Thr Tyr Asp Ser Ala Phe Glu
130                 135                 140

Ser His His Leu Ser Ser Gln Pro Ser His Met Gln His Ala Ser Thr
145                 150                 155                 160

Ala Gly Ile Ser Gly Leu His Glu Ser Gln Thr Ala Pro Ser His Ser
                165                 170                 175

Gln Ser Ser Leu Gly Thr Thr Ile Asp Ala Met His Leu Asn His Phe
                180                 185                 190

Asn Thr Met Asn Asp Ser Gly Arg Pro Ala Met Ser Ile Ser Asp Leu
                195                 200                 205

Arg Ser Leu Pro Pro Ser Val Leu Pro Gln Gly Leu Ser Ser Gly
210                 215                 220

Tyr Asn Ala Ser Ala Phe Ala Leu Val Asn Pro Gln Glu Pro Gly Ser
225                 230                 235                 240

Pro Ala Asn Gln Phe Arg Leu Gly Ser Ser Ala Glu Asn Pro Thr Ala
                245                 250                 255

Pro Phe Leu Gly Leu Ser Pro Pro Gly Gln Ser Pro Gly Trp Leu Pro
                260                 265                 270

Leu Pro Ser Pro Ser Pro Ala Asn Phe Pro Ser Phe Ser Leu His Pro
            275                 280                 285

Phe Ser Ser Thr Leu Arg Tyr Pro Val Leu Gln Pro Val Leu Pro His
            290                 295                 300

Ile Ala Ser Ile Ile Pro Gln Ser Leu Ala Cys Asp Leu Leu Asp Val
305                 310                 315                 320

Tyr Phe Thr Ser Ser Ser Ser His Leu Ser Pro Leu Ser Pro Tyr
                325                 330                 335

Val Val Gly Tyr Ile Phe Arg Lys Gln Ser Phe Leu His Pro Thr Lys
            340                 345                 350

Pro Arg Ile Cys Ser Pro Gly Leu Leu Ala Ser Met Leu Trp Val Ala
            355                 360                 365

Ala Gln Thr Ser Glu Ala Ala Phe Leu Thr Ser Pro Ser Ala Arg
            370                 375                 380

Gly Arg Val Cys Gln Lys Leu Leu Glu Leu Thr Ile Gly Leu Leu Arg
385                 390                 395                 400

Pro Leu Val His Gly Pro Ala Thr Gly Glu Ala Ser Pro Asn Tyr Ala
                405                 410                 415

Ala Asn Met Val Ile Asn Gly Val Ala Leu Gly Gly Phe Gly Val Ser
            420                 425                 430

Met Asp Gln Leu Gly Ala Gln Ser Ser Ala Thr Gly Ala Val Asp Asp
            435                 440                 445

Val Ala Thr Tyr Val His Leu Ala Thr Val Val Ser Ala Ser Glu Tyr
            450                 455                 460

Lys Ala Ala Ser Met Arg Trp Trp Thr Ala Ala Trp Ser Leu Ala Arg
465                 470                 475                 480

Glu Leu Lys Leu Gly Arg Glu Leu Pro Pro Asn Val Ser His Ala Arg
                485                 490                 495
```

```
Gln Asp Gly Glu Arg Asp Gly Asp Gly Glu Ala Asp Lys Arg His Pro
            500                 505                 510

Pro Thr Leu Ile Thr Ser Leu Gly His Gly Ser Gly Ser Ser Gly Ile
        515                 520                 525

Asn Val Thr Glu Glu Arg Glu Glu Arg Arg Arg Leu Trp Trp Leu
    530                 535                 540

Leu Tyr Ala Thr Asp Arg His Leu Ala Leu Cys Tyr Asn Arg Pro Leu
545                 550                 555                 560

Thr Leu Leu Asp Lys Glu Cys Gly Gly Leu Leu Gln Pro Met Asn Asp
                565                 570                 575

Asp Leu Trp Gln Val Gly Asp Phe Ala Ala Ala Tyr Arg Gln Val
            580                 585                 590

Gly Pro Pro Val Glu Cys Thr Gly His Ser Met Tyr Gly Tyr Phe Leu
        595                 600                 605

Pro Leu Met Thr Ile Leu Gly Gly Ile Val Asp Leu His His Ala Glu
    610                 615                 620

Asn His Pro Arg Phe Gly Leu Ala Phe Arg Asn Ser Pro Glu Trp Glu
625                 630                 635                 640

Arg Gln Val Leu Asp Val Thr Arg Gln Leu Asp Thr Tyr Gly Arg Ser
                645                 650                 655

Leu Lys Glu Phe Glu Ala Arg Tyr Thr Ser Asn Leu Thr Leu Gly Ala
            660                 665                 670

Thr Asp Asn Glu Pro Val Val Glu Gly Ala His Leu Asp His Thr Ser
        675                 680                 685

Pro Ser Gly Arg Ser Ser Ser Thr Val Gly Ser Arg Val Ser Glu Ser
    690                 695                 700

Ile Val His Thr Arg Met Val Val Ala Tyr Gly Thr His Ile Met His
705                 710                 715                 720

Val Leu His Ile Leu Leu Ala Gly Lys Trp Asp Pro Val Asn Leu Leu
                725                 730                 735

Glu Asp His Asp Leu Trp Ile Ser Ser Glu Ser Phe Val Ser Ala Met
            740                 745                 750

Ser His Ala Val Gly Ala Ala Glu Ala Ala Glu Ile Leu Glu Tyr
        755                 760                 765

Asp Pro Asp Leu Ser Phe Met Pro Phe Phe Gly Ile Tyr Leu Leu
    770                 775                 780

Gln Gly Ser Phe Leu Leu Leu Ala Ala Asp Lys Leu Gln Gly Asp
785                 790                 795                 800

Ala Ser Pro Ser Val Val Arg Ala Cys Glu Thr Ile Val Arg Ala His
                805                 810                 815

Glu Ala Cys Val Val Thr Leu Asn Thr Glu Tyr Gln Arg Thr Phe Arg
            820                 825                 830

Lys Val Met Arg Ser Ala Leu Ala Gln Val Arg Gly Arg Ile Pro Glu
        835                 840                 845

Asp Phe Gly Glu Gln Gln Gln Arg Arg Arg Glu Val Leu Ala Leu Tyr
    850                 855                 860

Arg Trp Ser Gly Asp Gly Ser Gly Leu Ala Leu
865                 870                 875

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
``` peptide motif

<400> SEQUENCE: 12

Arg Arg Arg Leu Trp Trp
1               5

<210> SEQ ID NO 13
<211> LENGTH: 211
<212> TYPE: PRT
<213> ORGANISM: Aspergillus tubingensis

<400> SEQUENCE: 13

Met Lys Val Thr Ala Ala Phe Ala Gly Leu Leu Val Thr Ala Phe Ala
        -25                 -20                 -15

Ala Pro Ala Pro Glu Pro Asp Leu Val Ser Arg Ser Ala Gly Ile Asn
        -10                  -5              -1   1               5

Tyr Val Gln Asn Tyr Asn Gly Asn Leu Gly Asp Phe Thr Tyr Asp Glu
                 10                  15                  20

Ser Ala Gly Thr Phe Ser Met Tyr Trp Glu Asp Gly Val Ser Ser Asp
             25                  30                  35

Phe Val Val Gly Leu Gly Trp Thr Thr Gly Ser Ser Asn Ala Ile Thr
         40                  45                  50

Tyr Ser Ala Glu Tyr Ser Ala Ser Gly Ser Ala Ser Tyr Leu Ala Val
     55                  60                  65

Tyr Gly Trp Val Asn Tyr Pro Gln Ala Glu Tyr Tyr Ile Val Glu Asp
 70                  75                  80                  85

Tyr Gly Asp Tyr Asn Pro Cys Ser Ser Ala Thr Ser Leu Gly Thr Val
                 90                  95                 100

Tyr Ser Asp Gly Ser Thr Tyr Gln Val Cys Thr Asp Thr Arg Thr Asn
            105                 110                 115

Glu Pro Ser Ile Thr Gly Thr Ser Thr Phe Thr Gln Tyr Phe Ser Val
            120                 125                 130

Arg Glu Ser Thr Arg Thr Ser Gly Thr Val Thr Val Ala Asn His Phe
            135                 140                 145

Asn Phe Trp Ala His His Gly Phe Gly Asn Ser Asp Phe Asn Tyr Gln
150                 155                 160                 165

Val Val Ala Val Glu Ala Trp Ser Gly Ala Gly Ser Ala Ser Val Thr
                170                 175                 180

Ile Ser Ser

<210> SEQ ID NO 14
<211> LENGTH: 605
<212> TYPE: PRT
<213> ORGANISM: Aspergillus niger

<400> SEQUENCE: 14

Met Gln Thr Leu Leu Val Ser Ser Leu Val Val Ser Leu Ala Ala Ala
         -20                 -15                 -10

Leu Pro His Tyr Ile Arg Ser Asn Gly Ile Glu Ala Ser Leu Leu Thr
  -5              -1   1               5                      10

Asp Pro Lys Asp Val Ser Gly Arg Thr Val Asp Tyr Ile Ile Ala Gly
                 15                  20                  25

Gly Gly Leu Thr Gly Leu Thr Thr Ala Ala Arg Leu Thr Glu Asn Pro
             30                  35                  40

Asn Ile Ser Val Leu Val Ile Glu Ser Gly Ser Tyr Glu Ser Asp Arg
         45                  50                  55

Gly Pro Ile Ile Glu Asp Leu Asn Ala Tyr Gly Asp Ile Phe Gly Ser

-continued

```
                60                   65                   70
Ser Val Asp His Ala Tyr Glu Thr Val Glu Leu Ala Thr Asn Asn Gln
75                  80                                      90

Thr Ala Leu Ile Arg Ser Gly Asn Gly Leu Gly Gly Ser Thr Leu Val
                95                  100                 105

Asn Gly Gly Thr Trp Thr Arg Pro His Lys Ala Gln Val Asp Ser Trp
            110                 115                     120

Glu Thr Val Phe Gly Asn Glu Gly Trp Asn Trp Asp Asn Val Ala Ala
            125                 130                 135

Tyr Ser Leu Gln Ala Glu Arg Ala Arg Ala Pro Asn Ala Lys Gln Ile
    140                 145                 150

Ala Ala Gly His Tyr Phe Asn Ala Ser Cys His Gly Val Asn Gly Thr
155                 160                 165                 170

Val His Ala Gly Pro Arg Asp Thr Gly Asp Tyr Ser Pro Ile Val
                175                 180                 185

Lys Ala Leu Met Ser Ala Val Glu Asp Arg Gly Val Pro Thr Lys Lys
            190                 195                 200

Asp Phe Gly Cys Gly Asp Pro His Gly Val Ser Met Phe Pro Asn Thr
            205                 210                 215

Leu His Glu Asp Gln Val Arg Ser Asp Ala Ala Arg Glu Trp Leu Leu
    220                 225                 230

Pro Asn Tyr Gln Arg Pro Asn Leu Gln Val Leu Thr Gly Gln Tyr Val
235                 240                 245                 250

Gly Lys Val Leu Leu Ser Gln Asn Gly Thr Thr Pro Arg Ala Val Gly
                255                 260                 265

Val Glu Phe Gly Thr His Lys Gly Asn Thr His Asn Val Tyr Ala Lys
            270                 275                 280

His Glu Val Leu Leu Ala Ala Gly Ser Ala Val Ser Pro Thr Ile Leu
        285                 290                 295

Glu Tyr Ser Gly Ile Gly Met Lys Ser Ile Leu Glu Pro Leu Gly Ile
    300                 305                 310

Asp Thr Val Val Asp Leu Pro Val Gly Leu Asn Leu Gln Asp Gln Thr
315                 320                 325                 330

Thr Ala Thr Val Arg Ser Arg Ile Thr Ser Ala Gly Ala Gly Gln Gly
                335                 340                 345

Gln Ala Ala Trp Phe Ala Thr Phe Asn Glu Thr Phe Gly Asp Tyr Ser
            350                 355                 360

Glu Lys Ala His Glu Leu Leu Asn Thr Lys Leu Glu Gln Trp Ala Glu
        365                 370                 375

Glu Ala Val Ala Arg Gly Gly Phe His Asn Thr Thr Ala Leu Leu Ile
380                 385                 390

Gln Tyr Glu Asn Tyr Arg Asp Trp Ile Val Asn His Asn Val Ala Tyr
395                 400                 405                 410

Ser Glu Leu Phe Leu Asp Thr Ala Gly Val Ala Ser Phe Asp Val Trp
                415                 420                 425

Asp Leu Leu Pro Phe Thr Arg Gly Tyr Val His Ile Leu Asp Lys Asp
            430                 435                 440

Pro Tyr Leu His His Phe Ala Tyr Asp Pro Gln Tyr Phe Leu Asn Glu
        445                 450                 455

Leu Asp Leu Leu Gly Gln Ala Ala Thr Gln Leu Ala Arg Asn Ile
    460                 465                 470

Ser Asn Ser Gly Ala Met Gln Thr Tyr Phe Ala Gly Glu Thr Ile Pro
475                 480                 485                 490
```

```
Gly Asp Asn Leu Ala Tyr Asp Ala Asp Leu Ser Ala Trp Thr Glu Tyr
                495                 500                 505

Ile Pro Tyr His Phe Arg Pro Asn Tyr His Gly Val Gly Thr Cys Ser
                510                 515                 520

Met Met Pro Lys Glu Met Gly Val Val Asp Asn Ala Ala Arg Val
                525                 530                 535

Tyr Gly Val Gln Gly Leu Arg Val Ile Asp Gly Ser Ile Pro Pro Thr
540                 545                 550

Gln Met Ser Ser His Val Met Thr Val Phe Tyr Ala Met Ala Leu Lys
555                 560                 565                 570

Ile Ser Asp Ala Ile Leu Glu Asp Tyr Ala Ser Met Gln
                575                 580

<210> SEQ ID NO 15
<211> LENGTH: 277
<212> TYPE: PRT
<213> ORGANISM: Aspergillus niger

<400> SEQUENCE: 15

Met Ser Ser Lys Ser Gln Leu Thr Tyr Thr Ala Arg Ala Ser Lys His
1               5                   10                  15

Pro Asn Ala Leu Ala Lys Arg Leu Phe Glu Ile Ala Glu Ala Lys Lys
                20                  25                  30

Thr Asn Val Thr Val Ser Ala Asp Val Thr Thr Thr Lys Glu Leu Leu
            35                  40                  45

Asp Leu Ala Asp Arg Leu Gly Pro Tyr Ile Ala Val Ile Lys Thr His
        50                  55                  60

Ile Asp Ile Leu Ser Asp Phe Ser Asp Glu Thr Ile Glu Gly Leu Lys
65                  70                  75                  80

Ala Leu Ala Gln Lys His Asn Phe Leu Ile Phe Glu Asp Arg Lys Phe
                85                  90                  95

Ile Asp Ile Gly Asn Thr Val Gln Lys Gln Tyr His Arg Gly Thr Leu
                100                 105                 110

Arg Ile Ser Glu Trp Ala His Ile Ile Asn Cys Ser Ile Leu Pro Gly
            115                 120                 125

Glu Gly Ile Val Glu Ala Leu Ala Gln Thr Ala Ser Ala Pro Asp Phe
        130                 135                 140

Ser Tyr Gly Pro Glu Arg Gly Leu Leu Ile Leu Ala Glu Met Thr Ser
145                 150                 155                 160

Lys Gly Ser Leu Ala Thr Gly Gln Tyr Thr Thr Ser Ser Val Asp Tyr
                165                 170                 175

Ala Arg Lys Tyr Lys Asn Phe Val Met Gly Phe Val Ser Thr Arg Ser
                180                 185                 190

Leu Gly Glu Val Gln Ser Glu Val Ser Ser Pro Ser Asp Glu Glu Asp
            195                 200                 205

Phe Val Val Phe Thr Thr Gly Val Asn Ile Ser Ser Lys Gly Asp Lys
        210                 215                 220

Leu Gly Gln Gln Tyr Gln Thr Pro Ala Ser Ala Ile Gly Arg Gly Ala
225                 230                 235                 240
```

-continued

```
Asp Phe Ile Ile Ala Gly Arg Gly Ile Tyr Ala Ala Pro Asp Pro Val
                245                 250                 255

Gln Ala Ala Gln Gln Tyr Gln Lys Glu Gly Trp Glu Ala Tyr Leu Ala
            260                 265                 270

Arg Val Gly Gly Asn
        275

<210> SEQ ID NO 16
<211> LENGTH: 804
<212> TYPE: PRT
<213> ORGANISM: Aspergillus niger

<400> SEQUENCE: 16

Met Ala His Ser Met Ser Arg Pro Val Ala Ala Thr Ala Ala Leu
    -25                 -20                 -15

Leu Ala Leu Ala Leu Pro Gln Ala Leu Ala Gln Ala Asn Thr Ser Tyr
-10              -5                  -1   1               5

Val Asp Tyr Asn Ile Glu Ala Asn Pro Asp Leu Tyr Pro Leu Cys Ile
                10                  15                  20

Glu Thr Ile Pro Leu Ser Phe Pro Asp Cys Gln Asn Gly Pro Leu Arg
            25                  30                  35

Ser His Leu Ile Cys Asp Glu Thr Ala Thr Pro Tyr Asp Arg Ala Ala
        40                  45                  50

Ser Leu Ile Ser Leu Phe Thr Leu Asp Glu Leu Ile Ala Asn Thr Gly
55                  60                  65                  70

Asn Thr Gly Leu Gly Val Ser Arg Leu Gly Leu Pro Ala Tyr Gln Val
                75                  80                  85

Trp Ser Glu Ala Leu His Gly Leu Asp Arg Ala Asn Phe Ser Asp Ser
            90                  95                  100

Gly Ala Tyr Asn Trp Ala Thr Ser Phe Pro Gln Pro Ile Leu Thr Thr
        105                 110                 115

Ala Ala Leu Asn Arg Thr Leu Ile His Gln Ile Ala Ser Ile Ile Ser
    120                 125                 130

Thr Gln Gly Arg Ala Phe Asn Asn Ala Gly Arg Tyr Gly Leu Asp Val
135                 140                 145                 150

Tyr Ala Pro Asn Ile Asn Thr Phe Arg His Pro Val Trp Gly Arg Gly
                155                 160                 165

Gln Glu Thr Pro Gly Glu Asp Val Ser Leu Ala Ala Val Tyr Ala Tyr
            170                 175                 180

Glu Tyr Ile Thr Gly Ile Gln Gly Pro Asp Pro Glu Ser Asn Leu Lys
        185                 190                 195

Leu Ala Ala Thr Ala Lys His Tyr Ala Gly Tyr Asp Ile Glu Asn Trp
    200                 205                 210

His Asn His Ser Arg Leu Gly Asn Asp Met Asn Ile Thr Gln Gln Asp
215                 220                 225                 230

Leu Ser Glu Tyr Tyr Thr Pro Gln Phe His Val Ala Ala Arg Asp Ala
                235                 240                 245

Lys Val Gln Ser Val Met Cys Ala Tyr Asn Ala Val Asn Gly Val Pro
            250                 255                 260

Ala Cys Ala Asp Ser Tyr Phe Leu Gln Thr Leu Leu Arg Asp Thr Phe
        265                 270                 275

Gly Phe Val Asp His Gly Tyr Val Ser Ser Asp Cys Asp Ala Ala Tyr
    280                 285                 290

Asn Ile Tyr Asn Pro His Gly Tyr Ala Ser Ser Gln Ala Ala Ala Ala
295                 300                 305                 310
```

```
Ala Glu Ala Ile Leu Ala Gly Thr Asp Ile Asp Cys Gly Thr Thr Tyr
            315                 320                 325

Gln Trp His Leu Asn Glu Ser Ile Ala Ala Gly Asp Leu Ser Arg Asp
            330                 335                 340

Asp Ile Glu Gln Gly Val Ile Arg Leu Tyr Thr Thr Leu Val Gln Ala
            345                 350                 355

Gly Tyr Phe Asp Ser Asn Thr Thr Lys Ala Asn Asn Pro Tyr Arg Asp
    360                 365                 370

Leu Ser Trp Ser Asp Val Leu Glu Thr Asp Ala Trp Asn Ile Ser Tyr
375                 380                 385                 390

Gln Ala Ala Thr Gln Gly Ile Val Leu Leu Lys Asn Ser Asn Asn Val
                395                 400                 405

Leu Pro Leu Thr Glu Lys Ala Tyr Pro Pro Ser Asn Thr Thr Val Ala
            410                 415                 420

Leu Ile Gly Pro Trp Ala Asn Ala Thr Thr Gln Leu Leu Gly Asn Tyr
                425                 430                 435

Tyr Gly Asn Ala Pro Tyr Met Ile Ser Pro Arg Ala Ala Phe Glu Glu
    440                 445                 450

Ala Gly Tyr Lys Val Asn Phe Ala Glu Gly Thr Gly Ile Ser Ser Thr
455                 460                 465                 470

Ser Thr Ser Gly Phe Ala Ala Ala Leu Ser Ala Ala Gln Ser Ala Asp
                475                 480                 485

Val Ile Ile Tyr Ala Gly Gly Ile Asp Asn Thr Leu Glu Ala Glu Ala
            490                 495                 500

Leu Asp Arg Glu Ser Ile Ala Trp Pro Gly Asn Gln Leu Asp Leu Ile
            505                 510                 515

Gln Lys Leu Ala Ser Ala Ala Gly Lys Lys Pro Leu Ile Val Leu Gln
            520                 525                 530

Met Gly Gly Gly Gln Val Asp Ser Ser Ser Leu Lys Asn Asn Thr Asn
535                 540                 545                 550

Val Ser Ala Leu Leu Trp Gly Gly Tyr Pro Gly Gln Ser Gly Gly Phe
                555                 560                 565

Ala Leu Arg Asp Ile Ile Thr Gly Lys Lys Asn Pro Ala Gly Arg Leu
            570                 575                 580

Val Thr Thr Gln Tyr Pro Ala Ser Tyr Ala Glu Glu Phe Pro Ala Thr
            585                 590                 595

Asp Met Asn Leu Arg Pro Glu Gly Asp Asn Pro Gly Gln Thr Tyr Lys
    600                 605                 610

Trp Tyr Thr Gly Glu Ala Val Tyr Glu Phe Gly His Gly Leu Phe Tyr
615                 620                 625                 630

Thr Thr Phe Ala Glu Ser Ser Asn Thr Thr Thr Lys Glu Val Lys
                635                 640                 645

Leu Asn Ile Gln Asp Ile Leu Ser Gln Thr His Glu Asp Leu Ala Ser
            650                 655                 660

Ile Thr Gln Leu Pro Val Leu Asn Phe Thr Ala Asn Ile Arg Asn Thr
                665                 670                 675

Gly Lys Leu Glu Ser Asp Tyr Thr Ala Met Val Phe Ala Asn Thr Ser
    680                 685                 690

Asp Ala Gly Pro Ala Pro Tyr Pro Lys Lys Trp Leu Val Gly Trp Asp
695                 700                 705                 710

Arg Leu Gly Glu Val Lys Val Gly Glu Thr Arg Glu Leu Arg Val Pro
            715                 720                 725

Val Glu Val Gly Ser Phe Ala Arg Val Asn Glu Asp Gly Asp Trp Val
            730                 735                 740
```

```
Val Phe Pro Gly Thr Phe Glu Leu Ala Leu Asn Leu Glu Arg Lys Val
            745                 750                 755
Arg Val Lys Val Val Leu Glu Gly Glu Glu Val Val Leu Lys Trp
    760                 765                 770
Pro Gly Lys Glu
775
```